US010610521B2

(12) United States Patent
Hsieh et al.

(10) Patent No.: US 10,610,521 B2
(45) Date of Patent: Apr. 7, 2020

(54) BIOMARKERS FOR RESPONSE TO RAPAMYCIN ANALOGS

(71) Applicant: MEMORIAL SLOAN-KETTERING CANCER CENTER, New York, NY (US)

(72) Inventors: James J. Hsieh, Englewood Cliffs, NJ (US); Michael Berger, New York, NY (US); Robert Motzer, Ridgewood, NJ (US); Martin H. Voss, New York, NY (US); A Ari Hakimi, New Rochelle, NY (US); Can Pham, New York, NY (US); Emily Cheng, Englewood Cliffs, NJ (US); Angela Rose Brannon, Cambridge, MA (US); Jianing Xu, Bronx, NY (US)

(73) Assignee: MEMORIAL SLOAN KETTERING CANCER CENTER, New York, NY (US)

(*) Notice: Subject to any disclaimer, the term of this patent is extended or adjusted under 35 U.S.C. 154(b) by 267 days.

(21) Appl. No.: 14/853,468

(22) Filed: Sep. 14, 2015

(65) Prior Publication Data
US 2016/0067229 A1 Mar. 10, 2016

Related U.S. Application Data

(63) Continuation of application No. PCT/US2014/028867, filed on Mar. 14, 2014.

(60) Provisional application No. 61/798,020, filed on Mar. 15, 2013, provisional application No. 61/852,109, filed on Mar. 15, 2013.

(51) Int. Cl.
A61K 31/44 (2006.01)
C40B 20/00 (2006.01)
C40B 40/06 (2006.01)
C40B 40/10 (2006.01)
A61K 31/436 (2006.01)
C12Q 1/6886 (2018.01)
C12Q 1/6806 (2018.01)

(52) U.S. Cl.
CPC .......... A61K 31/436 (2013.01); C12Q 1/6806 (2013.01); C12Q 1/6886 (2013.01); C12Q 2600/106 (2013.01); C12Q 2600/156 (2013.01)

(58) Field of Classification Search
None
See application file for complete search history.

(56) References Cited

U.S. PATENT DOCUMENTS 6,326,483 B1  12/2001 Kwiatkowski et al.
2005/0070567 A1  3/2005 Guan
2012/0157340 A1  6/2012 Cesano et al.
2012/0196870 A1  8/2012 Arbiser
2013/0196982 A1* 8/2013 Lynch ................. C07D 239/42 514/230.5
2014/0045881 A1* 2/2014 Vogelstein ........... C12Q 1/6886 514/291

FOREIGN PATENT DOCUMENTS

GB    2488028 A2 *  8/2012
WO   WO 2006/122053 A2   11/2006
WO   WO 2013/116735 A1   8/2013

OTHER PUBLICATIONS

Hegele Arteriosclerosis, Thrombosis, and Vascular Biology 2002 (22) 1058-1061.*
Pennisi Science 1998 (281) 1787.*
Lucentini The Scientist 2004, pp. 20.*
Ginsburg et al. Trends in Biotechnology 2001 (19) 491-496.*
Amato et al., "A Phase 2 Study With a Daily Regimen of the Oral mTOR Inhibitor RAD001 (Everolimus) in Patients With Metastatic Clear Cell Renal Cell Cancer," Cancer 115:2438-2446 (2009).
Atkins et al., "Randomized Phase II Study of Multiple Dose Levels of CCI-779, a Novel Mammalian Target of Rapamycin Kinase Inhibitor, in Patients With Advanced Refractory Renal Cell Carcinoma," J Clin Oncol 22(5):909-918 (2004).

(Continued)

Primary Examiner — Jeffrey S Lundgren
Assistant Examiner — Michael J Schmitt
(74) Attorney, Agent, or Firm — Baker Botts L.L.P.

(57) ABSTRACT

The present invention relates to the use of one or more biomarkers to evaluate the likelihood that a rapamycin analog would produce an anti-cancer effect in a subject. It is based, at least in part, on the results of experiments employing an integrated next-generation sequencing approach to interrogate spatially separated tumor specimens from the same individuals to decipher intra-tumor and intertumor heterogeneity and determine the oncogenomic basis of exceptional therapeutic benefit to rapalogs in kidney cancer patients. These experiments implicated loss of function mutations in TSC1 and/or TSC2 and/or gain-of-function of mTOR in therapeutic responsiveness to rapamycin analogs. Accordingly, in non-limiting embodiments, the present invention provides for assay methods and kits for determining the presence of loss of function mutations in TSC1 and/or TSC2 and/or gain-of-function of mTOR, and methods of using such determinations in selecting a therapeutic regimen for a cancer patient and in methods of treating cancer patients. In particular non-limiting embodiments, a plurality of tumor sites are evaluated and the composite effect of the genetic background on mTOR function is assessed.

Figure 1:
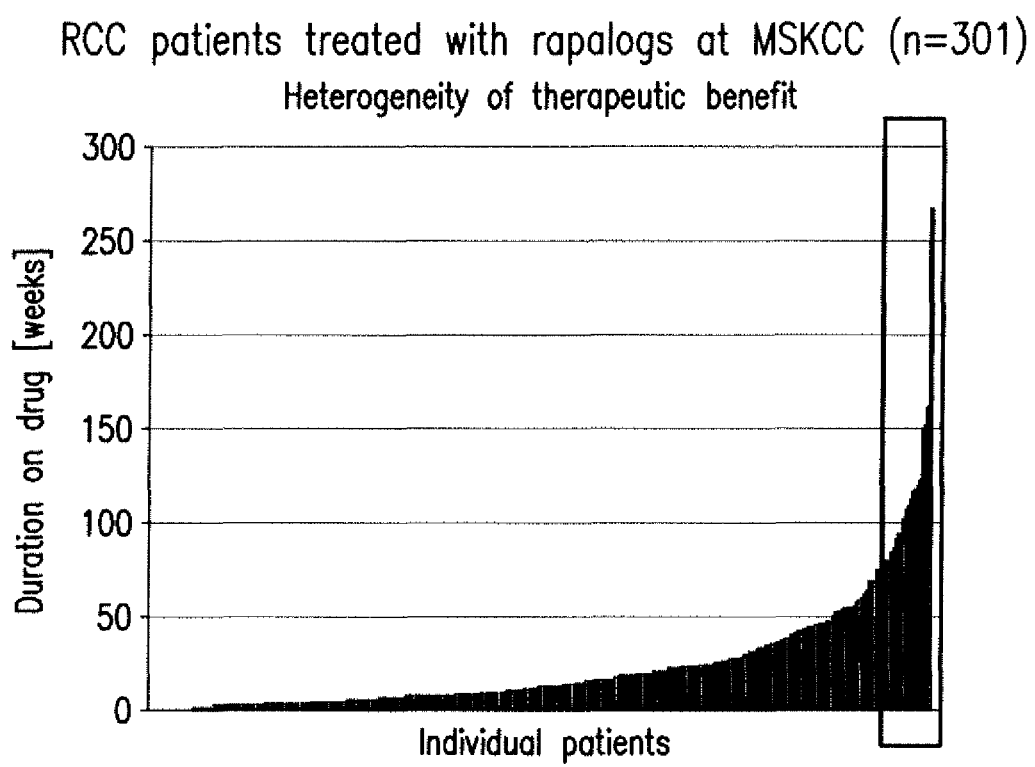

17 Claims, 41 Drawing Sheets
Specification includes a Sequence Listing.

(56) References Cited

OTHER PUBLICATIONS

Brugarolas, J., "Renal-Cell Carcinoma—Molecular Pathways and Therapies," N. Engl. J. Med. 356(2):185-187 (2007).
Cho et al., "Potential Histologic and Molecular Predictors of Response to Temsirolimus in Patients with Advanced Renal Cell Carcinoma," Clinical Genitourinary Cancer, 5(6):379-385 (2007).
Dazert et al., "mTOR signaling in disease," Current Opinion in Cell Biology 23:744-755 (2011).
DePristo et al., "A framework for variation discovery and genotyping using next-generation DNA sequencing data," Nat Genet 43(5):491-498 (2011).
Dutcher et al., "Effect of temsirolimus versus interferon-α on outcome of patients with advanced renal cell carcinoma of different tumor histologies," Med Oncol 26:202-209 (2009).
Gerlinger et al., "Intratumor Heterogeneity and Branched Evolution Revealed by Multiregion Sequencing," N Engl J Med 366(10):883-892 (2012).
Gnirke et al., "Solution hybrid selection with ultra-long oligonucleotides for massively parallel targeted sequencing," Nat Biotechnology 27(2):182-189 (2009).
Hanahan et al., "Hallmarks of Cancer: The Next Generation," Cell 144:646-674 (2011).
Hudes et al., "Temsirolimus, Interferon Alfa, or Both for Advanced Renal-Cell Carcinoma," N Engl. J. Med. 356(22):2271-2281 (2007).
International Search Report dated Nov. 5, 2014 in International Application No. PCT/US14/28867.
Iyer et al., "Genome Sequencing Identifies A Basis For Everolimus Sensitivity," Science, 338(6104):221 (2012).
Kaelin, W.G., Jr., "The von Hippel-Lindau tumour suppressor protein: 02 sensing and cancer," Nature Reviews. Cancer 8:865-873 (2008).
Kaelin, W.G., Jr., "Treatment of Kidney Cancer: Insights Provided by the VHL Tumor-Suppressor Protein," Cancer 115(10 suppl):2262-2272 (2009).
Kobayashi et al., "A germ-line Tsc1 mutation causes tumor development and embryonic lethality that are similar, but not identical to, those caused by Tsc2 mutation in mice," *PNAS*. Jul. 17, 2001, 98(15):8762-8767.
Krueger et al., "Everolimus for Subependymal Giant-Cell Astrocytomas in Tuberous Sclerosis," N Engl. J. Med. 363:1801-1811 (2010).
Kucejova et al., "Interplay Between pVHL and mTORC1 Pathways in Clear-Cell Renal Cell Carcinoma," *Molecular Cancer Research*, 9(9):1255-1265, Jul. 28, 2011.
Kwiatkowski, DJ., "Animal models of Lymphangioleiomyomatosis (LAM) and Tuberous Sclerosis Complex (TSC)," Lymphatic Research and Biology 8:51-57 (2010).
Laplante et al., "mTOR Signaling in Growth Control and Disease," Cell 149:274-293 (2012).
Li et al., "Fast and accurate short read alignment with Burrows-Wheeler transform," Bioinformatics 25(14):1754-1760 (2009).
Li et al., "The Sequence Alignment/Map format and SAMtools," Bioinformatics 25(16):2078-2079 (2009).
Linehan et al., "The genetic basis of kidney cancer: a metabolic disease," Nat. Rev. Urol. 7:277-285 (2010).
Longo, D.L., "Tumor Heterogeneity and Personalized Medicine," N Engl J Med 366(10): 956-957 (2012).
McKenna et al., "The Genome Analysis Toolkit: a MapReduce framework for analyzing next-generation DNA sequencing data," Genome Research 20:1297-1303 (2010).
Molina et al., "Long-term response with everolimus for metastatic renal cell carcinoma refractory to sunitinib," Med Oncol 28:1527-1529 (2011).
Molina et al., "Clinical Practice Guidelines for the Treatment of Metastatic Renal Cell Carcinoma: Today and Tomorrow," The Oncologist 16(suppl 2):45-50 (2011).
Motzer et al., "Efficacy of everolimus in advanced renal cell carcinoma: a double-blind, randomised, placebo-controlled phase III trial," Lancet 372:449-456 (2008).
Nowell, P.C., "The Clonal Evolution of Tumor Cell Populations," Science, New Series 194(4260):23-28 (1976).
Paez et al., "*EGFR* Mutations in Lung Cancer: Correlation with Clinical Response to Gefitinib Therapy," Science 304:1497-1500 (2004).
Qin et al., "Angiomyolipoma Have Common Mutations in TSC2 but No Other Common Genetic Events," PLoS One 6(9):e24919 (2011).
Robinson et al., "Integrative genomics viewer," Nature Biotechnology 29(1):24-26 (2011).
Sawyers, C.L., "The cancer biomarker problem," Nature 452:548-552 (2008).
Supplementary Partial European Search Report dated Oct. 21, 2016 in Application No. EP 14763457.
Urano et al., "Point mutations in TOR confer Rheb-independent growth in fission yeast and nutrient-independent mammalian TOR signaling in mammalian cells," PNAS 104(9):3514-3519 (2007).
Vivanco et al., "The phosphatidylinositol 3-Kinase AKT Pathway in Human Cancer," Nature Reviews. Cancer 2:489-501 (2002).
Vogelstein et al., "Cancer genes and the pathways they control," Nature Med 10(8):789-799 (2004).
Wagle et al., "High-throughput Detection of Actionable Genomic Alterations in Clinical Tumor Samples by Targeted, Massively Parallel Sequencing," Cancer Discovery 2(1):83-93 (2012).
Wander et al., "Next-Generation mTOR Inhibitors in Clinical Oncology: How Pathway Complexity Informs Therapeutic Strategy" *The Journal of Clinical Investigation*. 121(4):1231-1241 (2011).
Yap et al., "Intratumor Heterogeneity: Seeing the Wood for the Trees," Science Translational Medicine 4:(127): 127ps10 (2012).

\* cited by examiner

| Patient | Sex | Age | Histologic subtype | Rapalog | Duration treatment with rapalog (weeks) | # of metastatic sites | Duration prior treatment with sunitinib | Mutation identified |
|---|---|---|---|---|---|---|---|---|
| 1 | F | 58 | clear | temsirolimus | 117 | ≥3 | 60 | TSC1 |
| 2 | F | 73 | unclassified | temsirolimus | 147 | 1 | 13 | TSC1 |
| 3 | M | 66 | clear | everolimus | 87 | ≥3 | 21 | mTOR |
| 4 | M | 16 | unclassified | everolimus | 139 | 1 | 82 | TSC2 |
| 5 | F | 60 | clear | temsirolimus | 121 | ≥3 | 47 | NA |
| 6 | F | 50 | unclassified | temsirolimus | 126 | ≥3 | 9 | NA |

FIG. 2A

| Patient | Sex | Age | Histologic subtype | Rapalog | Duration treatment with rapalog (weeks) | # of metastatic sites | Duration prior treatment with sunitinib | Mutation identified |
|---|---|---|---|---|---|---|---|---|
| 7 | papillary | 1 | ≥3 | T | 1 | <1 | 17 (sorafenib) | |
| 8 | clear | 1 | ≥3 | E | 2 | 2 | 2 (sunitinib) | |
| 9 | chromophobe | 1 | 2 | T | 2 | 3 | 6 (sunitinib+bev) | |
| 11 | chromophobe | 1 | 2 | E | 1 | 1 | 5 (sunitinib) | |

FIG. 2B

|   | Histologic subtype | mTORi (months) | Relevant Mutations | Relevant CNA | Functional effect on mTOR pathway |
|---|---|---|---|---|---|
| 1 | clear | T (27) | TSC1 Frameshift | Het del Chr 9 | LOF TSC1 |
| 2 | unclassified | T (34) | TSC1 Frameshift | Het del Chr 9 | LOF TSC1 |
| 3 | clear | E (20) | mTOR Missense | – | GOF mTOR |
| 4 | unclassified | E (36+) | – | Hom del TSC2 | LOF TSC2 |
| 5 | clear | T (28) | – | – | – |
| 6 | unclassified | T (33+) | – | – | – | mTORi: mTOR inhibitor
CNA: copy number alteration
E: everolimus
T: temsirolimus
Hom del: homozygous deletion Chr: chromosome
LOF: loss of function
GOF: gain of function
Ampl: amplification
Het del: heterozygous deletion

FIG. 4

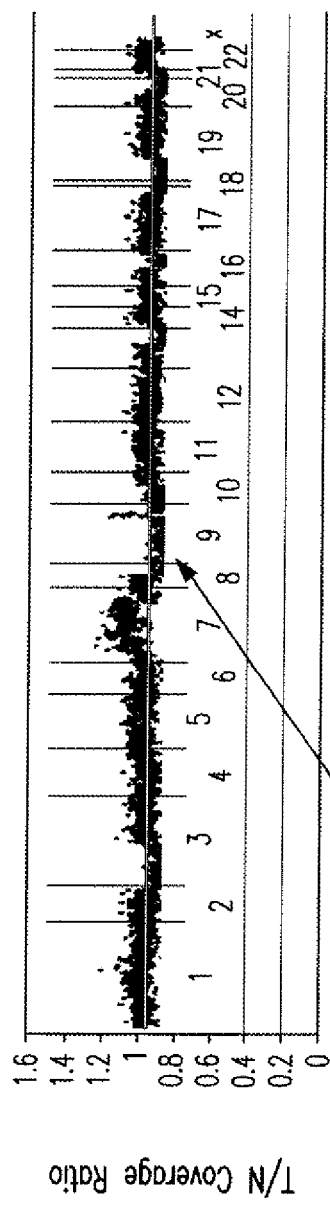
FIG. 5A
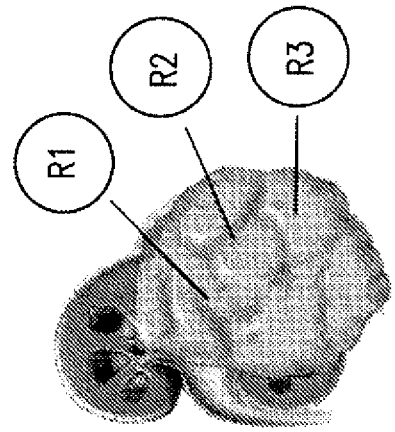
FIG. 5B
| Chr | Gene | Protein | R1 | R2 | R3 |
|---|---|---|---|---|---|
| 3 | VHL | p.E94* | 0.22 | 0.25 | 0.28 |
| 3 | PBRM1 | p.E991D | 0.24 | 0.22 | 0.26 |
| 4 | PHOX2B | p.G20V | 0.13 | 0.02 | 0 |
| 4 | NFKB1 | p.L611P | 0.16 | 0.17 | 0.18 |
| 4 | NFKB1 | p.A623V | 0.17 | 0.16 | 0.19 |
| 9 | TSC1 | p.P311fs | 0.22 | 0.22 | 0 |
| 9 | TSC1 | p.Q527* | 0 | 0 | 0.20 |
FIG. 5C

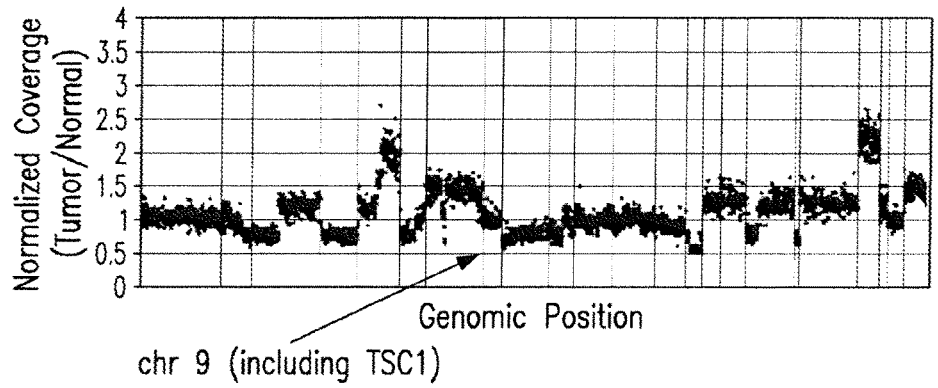
FIG. 6A
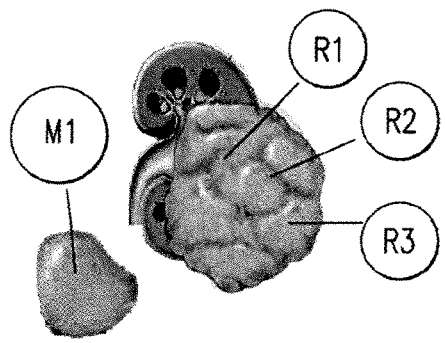
FIG. 6B
| Chr | Gene | Protein | R1 | R2 | R3 | M1 |
|---|---|---|---|---|---|---|
| 3 | VHL | p.H115N | 0.61 | 0.50 | 0.30 | 0.23 |
| 17 | TP53 | p.R273H | 0.59 | 0.52 | 0.29 | 0.25 |
| 1 | JAK1 | p.R110fs | 0.24 | 0.22 | 0.26 | 0.23 |
| 9 | TSC1 | p.I580fs | 0.60 | 0.44 | 0.29 | 0.25 |
| 15 | IGF1R | p.S847fs | 0.37 | 0.35 | 0.32 | 0.24 |
| 2 | ERBB4 | p.T360S | 0 | 0 | 0 | 0.11 |
| 9 | GNAQ | p.T96S | 0.03 | 0.09 | 0.09 | 0.06 |
FIG. 6C

| Chr | Gene | Protein | R1 | R2 | R3 | R4 |
|---|---|---|---|---|---|---|
| 1 | MTOR | p.Q2223K | 0.15 | 0.20 | 0.04 | 0 |
| 3 | BAP1 | p.G220_splice | 0.15 | 0.26 | 0.03 | 0.01 |
| 3 | VHL | p.G212 | 0.12 | 0.25 | 0.29 | 0.34 |
| 7 | MLL3 | p.V2060A | 0.14 | 0.22 | 0.28 | 0.28 |
| 3 | BAP1 | p.Q85_splice | 0 | 0 | 0.28 | 0.37 |
| 9 | NTRK2 | p.I511M | 0 | 0 | 0.08 | 0 |
| 9 | TSC1 | p.Q781* | 0 | 0 | 0.24 | 0.35 |
| 19 | PIK3R2 | p.G3V | 0 | 0 | 0.09 | 0 |

Summary  long-term responders

| Pt | mTORi | | Mutations | CNA | Functional effect |
|---|---|---|---|---|---|
| 1 | T (27) | R1 | TSC1 frameshift (P311fs) | Heterozygous del of TSC1 | Functional loss of TSC1 |
| | | R2 | TSC1 frameshift (P311fs) | Heterozygous del of TSC1 | Functional loss of TSC1 |
| | | R3 | TSC1 nonsense (Q527*) | Heterozygous del of TSC1 | Functional loss of TSC1 |
| 2 | T (34) | R1 | TSC1 frameshift (I580fs) | Heterozygous del of TSC1 | Functional loss of TSC1 |
| | | R2 | TSC1 frameshift (I580fs) | Heterozygous del of TSC1 | Functional loss of TSC1 |
| | | R3 | TSC1 frameshift (I580fs) | Heterozygous del of TSC1 | Functional loss of TSC1 |
| | | M1 | TSC1 frameshift (I580fs) | Heterozygous del of TSC1 | Functional loss of TSC1 |
| 3 | E (20) | R1 | mTOR missense (Q2223K) | – | Functional gain of mTOR |
| | | R2 | mTOR missense (Q2223K) | – | Functional gain of mTOR |
| | | R3 | mTOR missense (Q2223K) | – | Functional gain of mTOR |
| | | R4 | TSC1 nonsense (Q781*) | Heterozygous del of TSC1 | Functional loss of TSC1 |
| 4 | E (36+) | T1 | – | Heterozygous del of TSC2 | Functional loss of TSC2 |
| | | T2 | TSC2 nonsense (p.Q794*) | Heterozygous del of TSC2 | Functional loss of TSC2 |
| 5 | T (28) | T1 | – | – | – |
| | | M1 | – | – | – |
| 6 | E (33+) | T1 | – | – | – | mTORi: mTOR inhibitor        T: temsirolimus         del: deletion
CNA: copy number alteration  E: everolimus

FIG. 10

| Pt | mTORi | Mutations | CNA | Functional effect |
|---|---|---|---|---|
| 7 | T (1) | – | – | – |
| 8 | E (2) | mTOR missense (E919V) | – | – |
| 9 | T (2) | TSC2 frameshift (1475F) | Ampl MAP2K1 | – |
| 10 | E (1) | PTEN missense (F200l) | – | – | mTORi: mTOR inhibitor
CNA: copy number alteration

T: temsirolimus
E: everolimus ampl: amplification

FIG. 11

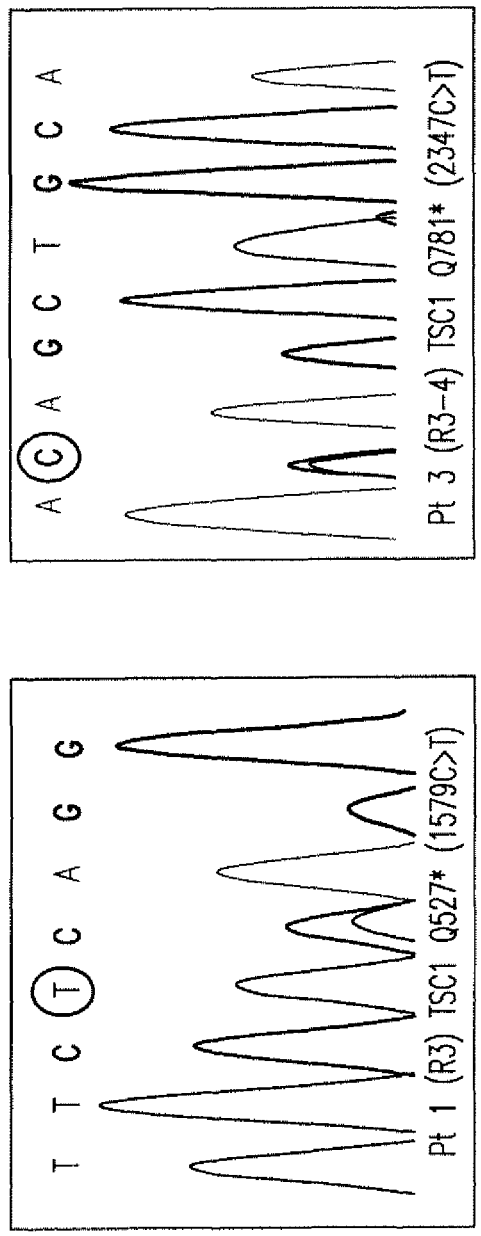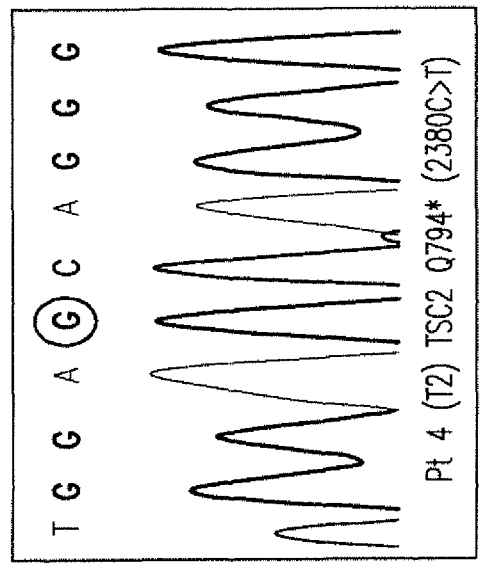
FIG. 21

SEQUENCE LISTING

<160> NUMBER OF SEQ ID NOS: 32

<210> SEQ ID NO 1
<211> LENGTH: 601
<212> TYPE: PRT
<213> ORGANISM: Homo sapiens

<400> SEQUENCE: 1

```
Leu Leu Gly Glu Arg Ala Ala Lys Cys Arg Ala Tyr Ala Lys Ala Leu
1               5                   10                  15

His Tyr Lys Glu Leu Glu Phe Gln Lys Gly Pro Thr Pro Ala Ile Leu
            20                  25                  30

Glu Ser Leu Ile Ser Ile Asn Asn Lys Leu Gln Gln Pro Glu Ala Ala
        35                  40                  45

Ala Gly Val Leu Glu Tyr Ala Met Lys His Phe Gly Glu Leu Glu Ile
    50                  55                  60

Gln Ala Thr Trp Tyr Glu Lys Leu His Glu Trp Glu Asp Ala Leu Val
65                  70                  75                  80

Ala Tyr Asp Lys Lys Met Asp Thr Asn Lys Asp Asp Pro Glu Leu Met
                85                  90                  95

Leu Gly Arg Met Arg Cys Leu Glu Ala Leu Gly Glu Trp Gly Gln Leu
            100                 105                 110

His Gln Gln Cys Cys Glu Lys Trp Thr Leu Val Asn Asp Glu Thr Gln
        115                 120                 125

Ala Lys Met Ala Arg Met Ala Ala Ala Ala Trp Gly Leu Gly Gln
    130                 135                 140

Trp Asp Ser Met Glu Glu Tyr Thr Cys Met Ile Pro Arg Asp Thr His
145                 150                 155                 160

Asp Gly Ala Phe Tyr Arg Ala Val Leu Ala Leu His Gln Asp Leu Phe
                165                 170                 175

Ser Leu Ala Gln Gln Cys Ile Asp Lys Ala Arg Asp Leu Leu Asp Ala
            180                 185                 190

Glu Leu Thr Ala Met Ala Gly Glu Ser Tyr Ser Arg Ala Tyr Gly Ala
        195                 200                 205

Met Val Ser Cys His Met Leu Ser Glu Leu Glu Glu Val Ile Gln Tyr
    210                 215                 220

Lys Leu Val Pro Glu Arg Arg Glu Ile Ile Arg Gln Ile Trp Trp Glu
225                 230                 235                 240

Arg Leu Gln Gly Cys Gln Arg Ile Val Glu Asp Trp Gln Lys Ile Leu
                245                 250                 255

Met Val Arg Ser Leu Val Val Ser Pro His Glu Asp Met Arg Thr Trp
            260                 265                 270

Leu Lys Tyr Ala Ser Leu Cys Gly Lys Ser Gly Arg Leu Ala Leu Ala
        275                 280                 285

His Lys Thr Leu Val Leu Leu Gly Val Asp Pro Ser Arg Gln Leu
    290                 295                 300

Asp His Pro Leu Pro Thr Val His Pro Gln Val Thr Tyr Ala Tyr Met
305                 310                 315                 320

Lys Asn Met Trp Lys Ser Ala Arg Lys Ile Asp Ala Phe Gln His Met
                325                 330                 335

Gln His Phe Val Gln Thr Met Gln Gln Gln Ala Gln His Ala Ile Ala
            340                 345                 350

Thr Glu Asp Gln Gln His Lys Gln Glu Leu His Lys Leu Met Ala Arg
        355                 360                 365
```

-continued

```
Cys Phe Leu Lys Leu Gly Glu Trp Gln Leu Asn Leu Gln Gly Ile Asn
    370                 375                 380

Glu Ser Thr Ile Pro Lys Val Leu Gln Tyr Tyr Ser Ala Ala Thr Glu
385                 390                 395                 400

His Asp Arg Ser Trp Tyr Lys Ala Trp His Ala Trp Ala Val Met Asn
                405                 410                 415

Phe Glu Ala Val Leu His Tyr Lys His Gln Asn Gln Ala Arg Asp Glu
                420                 425                 430

Lys Lys Lys Leu Arg His Ala Ser Gly Ala Asn Ile Thr Asn Ala Thr
                435                 440                 445

Thr Ala Ala Thr Thr Ala Ala Thr Ala Thr Thr Thr Ala Ser Thr Glu
    450                 455                 460

Gly Ser Asn Ser Glu Ser Glu Ala Glu Ser Thr Glu Asn Ser Pro Thr
465                 470                 475                 480

Pro Ser Pro Leu Gln Lys Lys Val Thr Glu Asp Leu Ser Lys Thr Leu
                485                 490                 495

Leu Met Tyr Thr Val Pro Ala Val Gln Gly Phe Phe Arg Ser Ile Ser
                500                 505                 510

Leu Ser Arg Gly Asn Asn Leu Gln Asp Thr Leu Arg Val Leu Thr Leu
    515                 520                 525

Trp Phe Asp Tyr Gly His Trp Pro Asp Val Asn Glu Ala Leu Val Glu
530                 535                 540

Gly Val Lys Ala Ile Gln Ile Asp Thr Trp Leu Gln Val Ile Pro Gln
545                 550                 555                 560

Leu Ile Ala Arg Ile Asp Thr Pro Arg Pro Leu Val Gly Arg Leu Ile
                565                 570                 575

His Gln Leu Leu Thr Asp Ile Gly Arg Tyr His Pro Gln Ala Leu Ile
                580                 585                 590

Tyr Pro Leu Thr Val Ala Ser Lys Ser
    595                 600

<210> SEQ ID NO 2
<211> LENGTH: 101
<212> TYPE: PRT
<213> ORGANISM: Homo sapiens

<400> SEQUENCE: 2

Lys Glu Leu Glu Phe Gln Lys Gly Pro Thr Pro Ala Ile Leu Glu Ser
1               5                   10                  15

Leu Ile Ser Ile Asn Asn Lys Leu Gln Gln Pro Glu Ala Ala Ala Gly
            20                  25                  30

Val Leu Glu Tyr Ala Met Lys His Phe Gly Glu Leu Glu Ile Gln Ala
        35                  40                  45

Thr Trp Tyr Glu Lys Leu His Glu Trp Glu Asp Ala Leu Val Ala Tyr
    50                  55                  60

Asp Lys Lys Met Asp Thr Asn Lys Asp Asp Pro Glu Leu Met Leu Gly
65                  70                  75                  80

Arg Met Arg Cys Leu Glu Ala Leu Gly Glu Trp Gly Gln Leu His Gln
                85                  90                  95

Gln Cys Cys Glu Lys
            100

<210> SEQ ID NO 3
<211> LENGTH: 133
<212> TYPE: PRT
<213> ORGANISM: Homo sapiens
```

<400> SEQUENCE: 3

```
Glu Ser Glu Ala Glu Ser Thr Glu Asn Ser Pro Thr Pro Ser Pro Leu
1               5                   10                  15

Gln Lys Lys Val Thr Glu Asp Leu Ser Lys Thr Leu Leu Met Tyr Thr
            20                  25                  30

Val Pro Ala Val Gln Gly Phe Phe Arg Ser Ile Ser Leu Ser Arg Gly
        35                  40                  45

Asn Asn Leu Gln Asp Thr Leu Arg Val Leu Thr Leu Trp Phe Asp Tyr
    50                  55                  60

Gly His Trp Pro Asp Val Asn Glu Ala Leu Val Glu Gly Val Lys Ala
65                  70                  75                  80

Ile Gln Ile Asp Thr Trp Leu Gln Val Ile Pro Gln Leu Ile Ala Arg
                85                  90                  95

Ile Asp Thr Pro Arg Pro Leu Val Gly Arg Leu Ile His Gln Leu Leu
            100                 105                 110

Thr Asp Ile Gly Arg Tyr His Pro Gln Ala Leu Ile Tyr Pro Leu Thr
        115                 120                 125

Val Ala Ser Lys Ser
    130
```

<210> SEQ ID NO 4
<211> LENGTH: 335
<212> TYPE: PRT
<213> ORGANISM: Homo sapiens

<400> SEQUENCE: 4

```
Phe Val Phe Leu Leu Lys Gly His Glu Asp Leu Arg Gln Asp Glu Arg
1               5                   10                  15

Val Met Gln Leu Phe Gly Leu Val Asn Thr Leu Leu Ala Asn Asp Pro
            20                  25                  30

Thr Ser Leu Arg Lys Asn Leu Ser Ile Gln Arg Tyr Ala Val Ile Pro
        35                  40                  45

Leu Ser Thr Asn Ser Gly Leu Ile Gly Trp Val Pro His Cys Asp Thr
    50                  55                  60

Leu His Ala Leu Ile Arg Asp Tyr Arg Glu Lys Lys Ile Leu Leu
65                  70                  75                  80

Asn Ile Glu His Arg Ile Met Leu Arg Met Ala Pro Asp Tyr Asp His
                85                  90                  95

Leu Thr Leu Met Gln Lys Val Glu Val Phe Glu His Ala Val Asn Asn
            100                 105                 110

Thr Ala Gly Asp Asp Leu Ala Lys Leu Leu Trp Leu Lys Ser Pro Ser
        115                 120                 125

Ser Glu Val Trp Phe Asp Arg Arg Thr Asn Tyr Thr Arg Ser Leu Ala
    130                 135                 140

Val Met Ser Met Val Gly Tyr Ile Leu Gly Leu Gly Asp Arg His Pro
145                 150                 155                 160

Ser Asn Leu Met Leu Asp Arg Leu Ser Gly Lys Ile Leu His Ile Asp
                165                 170                 175

Phe Gly Asp Cys Phe Glu Val Ala Met Thr Arg Glu Lys Phe Pro Glu
            180                 185                 190

Lys Ile Pro Phe Arg Leu Thr Arg Met Leu Thr Asn Ala Met Glu Val
        195                 200                 205

Thr Gly Leu Asp Gly Asn Tyr Arg Ile Thr Cys His Thr Val Met Glu
    210                 215                 220
```

-continued

```
Val Leu Arg Glu His Lys Asp Ser Val Met Ala Val Leu Glu Ala Phe
225                 230                 235                 240

Val Tyr Asp Pro Leu Leu Asn Trp Arg Leu Met Asp Thr Asn Thr Lys
                245                 250                 255

Gly Asn Lys Arg Ser Arg Thr Arg Thr Asp Ser Tyr Ser Ala Gly Gln
            260                 265                 270

Ser Val Glu Ile Leu Asp Gly Val Glu Leu Gly Glu Pro Ala His Lys
        275                 280                 285

Lys Thr Gly Thr Thr Val Pro Glu Ser Ile His Ser Phe Ile Gly Asp
    290                 295                 300

Gly Leu Val Lys Pro Glu Ala Leu Asn Lys Lys Ala Ile Gln Ile Ile
305                 310                 315                 320

Asn Arg Val Arg Asp Lys Leu Thr Gly Arg Asp Phe Ser His Asp
                325                 330                 335
```

<210> SEQ ID NO 5
<211> LENGTH: 51
<212> TYPE: PRT
<213> ORGANISM: Homo sapiens

<400> SEQUENCE: 5

```
Gln Leu Phe Gly Leu Val Asn Thr Leu Leu Ala Asn Asp Pro Thr Ser
1               5                   10                  15

Leu Arg Lys Asn Leu Ser Ile Gln Arg Tyr Ala Val Ile Pro Leu Ser
            20                  25                  30

Thr Asn Ser Gly Leu Ile Gly Trp Val Pro His Cys Asp Thr Leu His
        35                  40                  45

Ala Leu Ile
    50
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagccctaca ggaattaccc tactttgc                                       28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcagcctgt cagtatccaa gtcaagtc                                       28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ccagctgttt ggccccaacc tggatgac                                      28
```

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gcggccggag tgtcagaata tgccatgaaa c                                  31
```

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
cacgagtggg aggatcccct tgtggcctat g                                  31
```

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gtgggaggat gcccctgtgg cctatgacaa g                                  31
```

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
gggccgcatg cgcttcctcg aggccttggg                                    30
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gcagtgatga acttcaaagc tgtgctacac                                    30
```

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
ctgccgtcca gggcatcttc cgttccatct c                                  31
```

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gccgtccagg gcttgttccg ttccatctcc                                    30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgccgtcca gggcgtcttc cgttccatct c                                  31

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccccaggcc ctcttctacc cactgacag                                     29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catctaccca ctgaaagtgg cttctaagtc                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacagcaaca ccctgctcca gcaggccatg                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccaatgaccc aacatttctt cggaaaaacc                                    30

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catctcttcg gaaaaacttc agcatccaga g                                    31

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggaaaaacct cagcatcaag agatacgctg tc                                   32

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gagatacgct gtcaccccTT tatcgacc                                        28

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgctgtcatc cctgtatcga ccaactcgg                                       29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gttctttagc ggtcatatca atggttggg                                       29

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cacagtgatg gaggcgctgc gagagcac                                        28

```
<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctgaactgg aggccgatgg acacaaatac c                                31

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gattattaac agggttccag ataagctcac tgg                              33

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 aagggtaga ag                                                      12

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtgaagatac tg                                                     12

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tggagcaggg                                                        10

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tcactgctga a                                                      11
```

US 10,610,521 B2

BIOMARKERS FOR RESPONSE TO RAPAMYCIN ANALOGS

PRIORITY CLAIM

This application is a continuation of International Patent Application No. PCT/US2014/028867 filed Mar. 14, 2014 and claims priority to U.S. Provisional Application Nos. 61/798,020 and 61/852,109, both filed Mar. 15, 2013, the contents of all three of which are hereby incorporated by reference herein in their entireties.

1. INTRODUCTION

The present invention relates to biomarkers which may be used to evaluate the likelihood that a rapamycin analog would produce an anti-cancer effect in a subject. As such, these biomarkers may be used in methods of treating cancer patients.

2. BACKGROUND OF THE INVENTION

Targeted therapies, including vascular endothelial growth factor receptor (VEGFR) inhibitors such as sunitinib (first line therapy), and mTOR inhibitors such as temsirolimus and everolimus (second line therapy), are standard of care in treating advanced renal cell carcinoma (RCC; 1-4). Temsirolimus and everolimus are rapamycin analogs (rapalogs) that inhibit the mammalian target of rapamycin complex 1 (mTORC1)5-7. International phase III trials led to their approval for treating kidney cancer, yet only demonstrated modest clinical benefit with median progression free survival (PFS) of 4.9-5.5 months (8-11).

However, extended periods of freedom from disease progression with rapalogs have been reported in isolated patients among whom some were refractory to first line antiangiogenic agents (10,12,13). These clinical data raise a testable hypothesis that genomic alterations may dictate clinical response.

Hyperactive PI3K/AKT/mTOR signaling, through its effects on protein synthesis, cell survival, and metabolism, has long been implicated in promoting tumor growth. The serine-threonine kinase mTOR exerts its actions as the enzymatic component of two structurally and functionally distinct multi-protein complexes, mTORC1 and mTORC2 (6,7). Therapeutic inhibition of mTORC1 is the mechanism of action for rapalogs. Components of the PI3K/mTOR pathway can either act as activators (PI3K, AKT, and Rheb) or repressors (PTEN, TSC1, and TSC2) of the mTORC1 signaling (14). Functional loss of TSC1 and TSC2 was shown in preclinical models to sensitize tumors to rapalogs (15), and everolimus has been approved for treating subependymal giant-cell astrocytomas and angiomyolipoma in patients with Tuberous Sclerosis Complex (16,17). Recent reports have also implicated TSC1 as a tumor suppressor in RCC and bladder cancer patients (18,19). However, the recent elucidation of intra-tumor heterogeneity of kidney cancer challenges the predictability of genomic biomarkers derived from single biopsies (20).

3. SUMMARY OF THE INVENTION

The present invention relates to the use of one or more biomarkers to evaluate the likelihood that a rapamycin analog would produce an anti-cancer effect in a subject. It is based, at least in part, on the results of experiments employing an integrated next-generation sequencing approach to interrogate spatially separated tumor specimens from the same individuals to decipher intra-tumor and intertumor heterogeneity and determine the oncogenomic basis of exceptional therapeutic benefit to rapalogs in kidney cancer patients. These experiments implicated loss of function mutations in TSC1 and/or TSC2 and/or gain-of-function of mTOR in therapeutic responsiveness to rapamycin analogs.

Accordingly, in non-limiting embodiments, the present invention provides for assay methods and kits for determining the presence of loss of function mutations in TSC1 and/or TSC2 and/or gain-of-function of mTOR, and methods of using such determinations in selecting a therapeutic regimen for a cancer patient and in methods of treating cancer patients.

In particular non-limiting embodiments, a plurality of tumor sites are evaluated and the composite effect of the genetic background on mTOR function is assessed.

4. BRIEF DESCRIPTION OF THE DRAWINGS

FIG. 1. Heterogeneity of therapeutic benefit of renal carcinoma patients treated with rapalog (n301). Duration of rapalog treatment (in weeks) for individual patients are shown. Box marks patients deemed to have received substantial therapeutic benefit.

FIG. 2A-B, Characteristics of clinical "outlier" patients (A) from among the group receiving substantial therapeutic benefit ("Long-term Responders") or (B) from among those who did not substantially benefit from treatment ("Poor Responders").

Figure 3A:
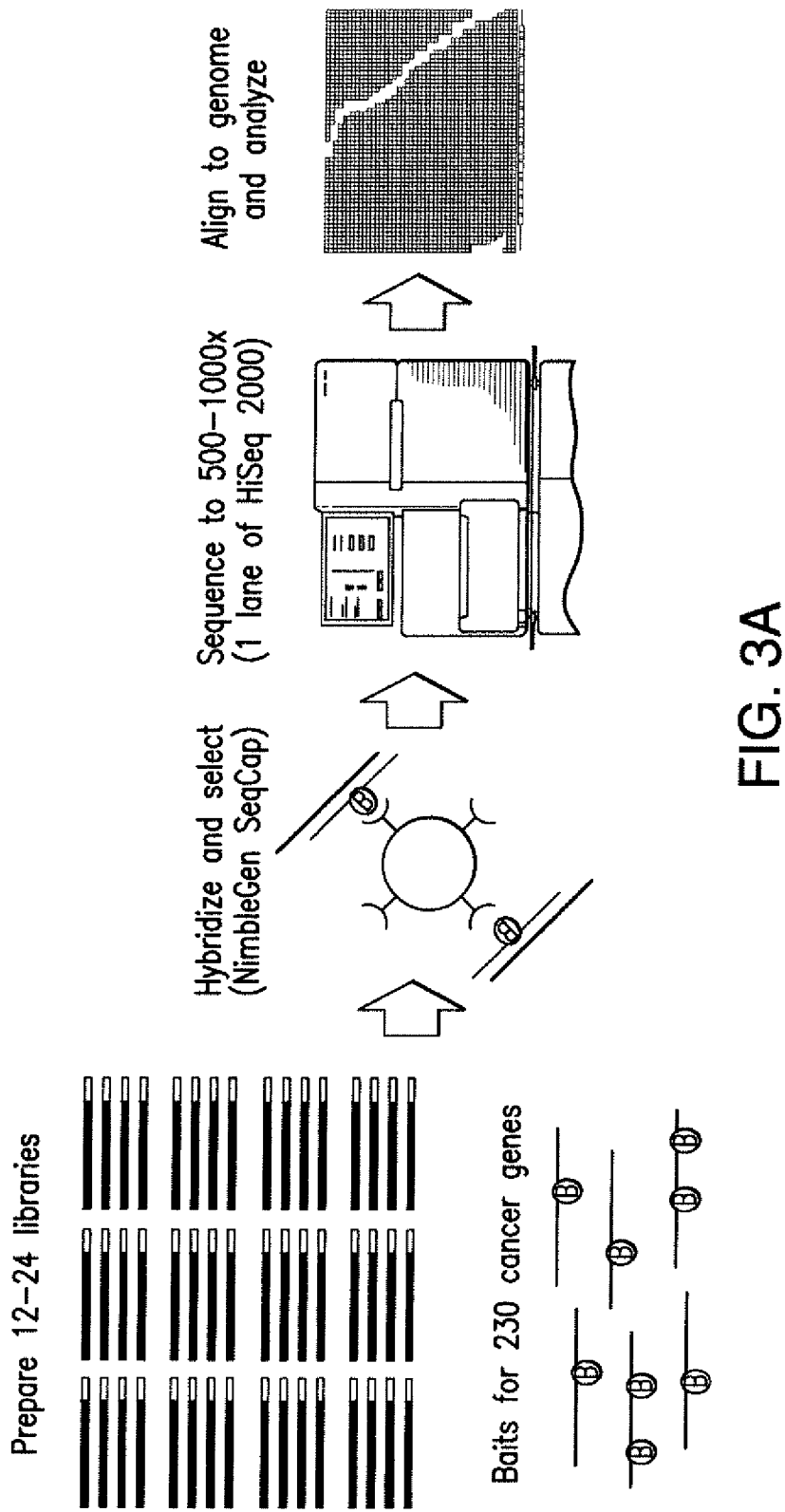
Figure 3B:
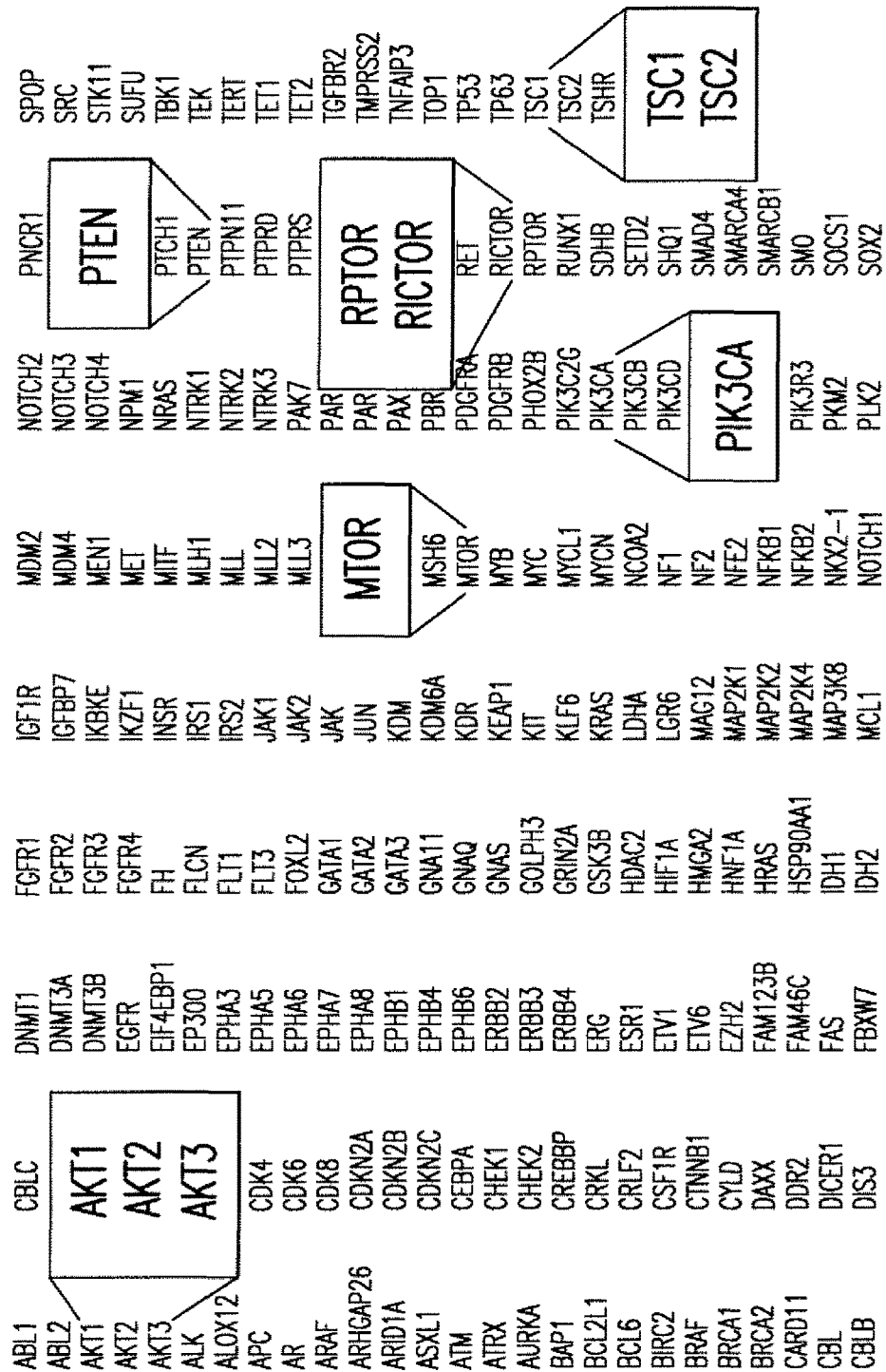

FIG. 3A-B. (A) Integrated Mutation Profiling of Actionable Cancer Targets ("IMPACT") analysis. Image adapted from Wagle, Berger et al., 2012, Cancer Discovery 2:82-93, reference 36. (B) Genes included in IMPACT panel. Genes of interest to mTOR pathway are enlarged and in bold.

FIG. 4. Summary of results for responders.

FIG. 5A-C. Results for patient 1, diagnosed with clear cell RCC and showing long-term response to temsirolimus. (A) Normalized coverage (tumor/normal) across the genome. (B) Schematic showing tumor sampling sites. (C) Genetic results.

FIG. 6A-C. Results for patient 2, diagnosed with unclassified RCC and showing long-term response to temsirolimus. (A) Normalized coverage (tumor/normal) across the genome (B) Schematic showing tumor sampling sites. (C) Genetic results.

Figures 7A, 7B:
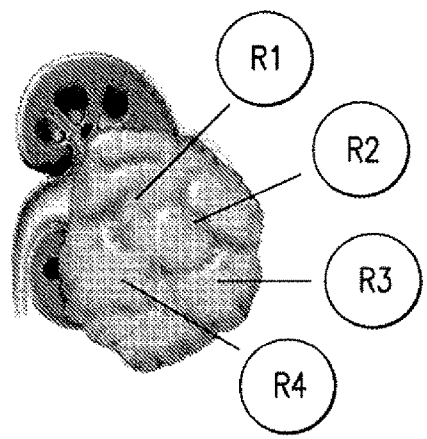

FIG. 7A-B. Results for patient 3, diagnosed with clear cell RCC and showing long-term response to everolimus. (A) Schematic showing tumor sampling sites. (B) Genetic results.

FIG. 8A-D. Results for patient 3 (see above). (A) Normalized coverage (tumor/normal) across the genome for tumor site 1. (B) Immunoblots of S6K (T389) showing phosphorylation of S6K, downstream of mTOR. (C) Genetic results. (D) Map of mTOR gene showing exons and functional domains.

FIG. 9A-D. Results for patient 4, diagnosed with unclassified RCC and showing long-term response to everolimus. (A) Schematic showing tumor sites in kidneys. (B) Normalized coverage (tumor/normal) across the genome for tumor site 1—no mutations found, but homozygous loss of TSC2. (C) Normalized coverage (tumor/normal) across the genome for tumor site 2, (D) Genetic results.

FIG. 10. Summary of results of long-term responders.

FIG. 11. Summary of results of poor responders.

FIG. 12A-F. Genomic alterations along the core mTORC1 pathway are identified in patients with exceptional rapalog response using the IMPACT assays. (A, B) Integrated Genomics Viewer (IGV) snapshots of region 1 (R1) of the primary tumors and matched adjacent normal tissues illustrate the P311fs*4 and the I580fs*7 frameshift mutations of TSC1 in patients #1 (a) and #2 (b), respectively. Number of reads carrying the mutation is noted. (C) A magnified copy number plot of tumor 1 (T1) in patient #4 illustrates the homozygous loss of chromosome 16p where TSC2 resides. (D) IGV snapshots of R1 and adjacent normal in patient #3 illustrate the mTOR Q2223K missense kinase domain mutation. (E) Copy number plots of patients #1 to #6 with notations on pertinent chromosomal alterations. TSC1, TSC2, and mTOR reside on chromosome bands 9q34, 16p13, and 1p36, respectively. (F) A diagram of the central mTORC1 signaling pathway illustrates mutations identified in the core components from rapalog (everolimus and temsirolimus) responders.

FIG. 13A-F. The Q2223K mutation of mTOR causes hyperactivation of mTORC1. (A) The mTOR Q2223K mutant induces more phosphorylation of endogenous S6K at threonine 389 (T389) than wild-type mTOR. HEK293T cells, transfected with the indicated FlagmTOR constructs for 24 hours, were serum-deprived overnight and then exposed to 1% serum-containing medium for 1 hour. Cellular lysates were subjected to immunoblot analysis using the indicated antibodies. Levels of Flag-mTOR and β-actin indicate equivalent transfection and protein loading, respectively. n.s. denotes non-specific bands. (B) Immunoblots of S6K (T389) and 86 (Serine 235/236; S235/236) phosphorylation demonstrate the hyperactivity of Q2223K mTORC1 over a range of serum concentrations. HEK293T cells, transfected with the indicated Flag-mTOR constructs for 24 hours, were washed with serum free medium, exposed to medium containing the indicated serum concentrations for 1 hour, and analyzed by immunoblots using the indicated antibodies. (C) The hyperactivity of Q2223K mTORC1 can be inhibited by rapamycin. The Q2223K mutant is as sensitive as wild-type mTORC1 to rapamycin as determined by the phosphorylation of S6K (T389). Experiments were performed as in (B), except with addition of the indicated concentrations (nM) of rapamycin in medium containing 10% serum in the final hour prior to harvest. (D,E) Cells in (D) and (E) were treated similarly to (b) and (c), respectively, except with the co-transfection of Myc-tagged S6K. (F) Structural simulation of the mTOR kinase active site, based on the solved PI3K kinase domain, illustrates the position of glutamine 2,223. Q2223 shown in yellow sticks is localized on a loop in close proximity to the ATP binding site (shown as colored lines—gray: carbon; red: oxygen; blue: nitrogen; orange: phosphorus). The kinase activation and catalytic loops are colored red and green, respectively.

Figure 14A:
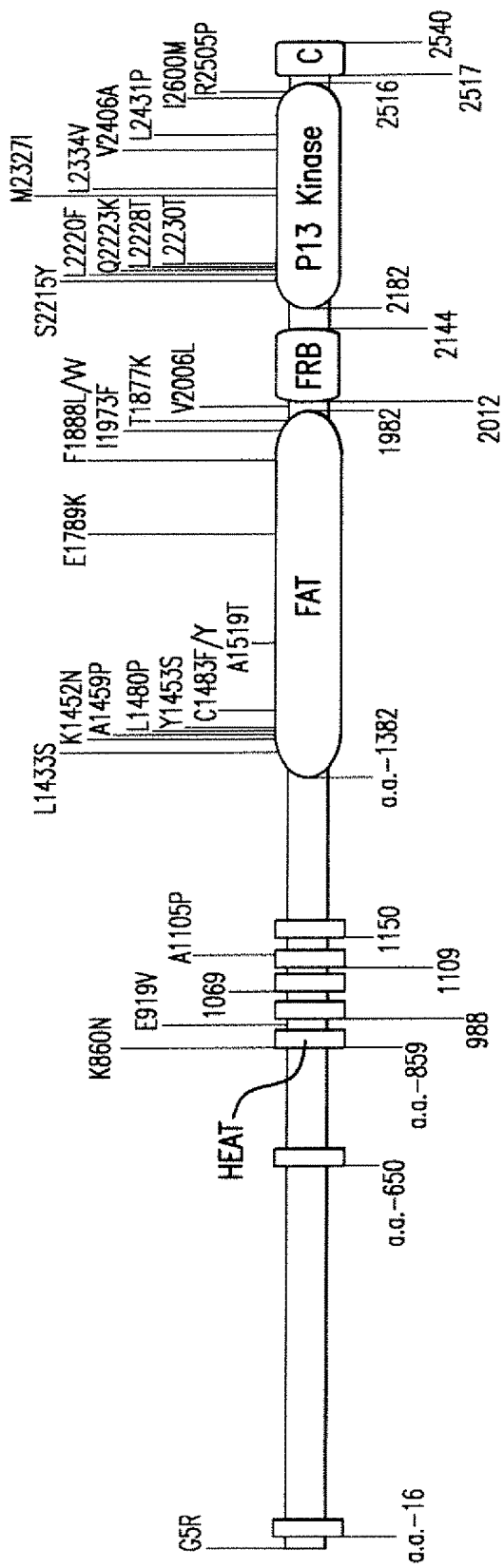
Figure 14B:
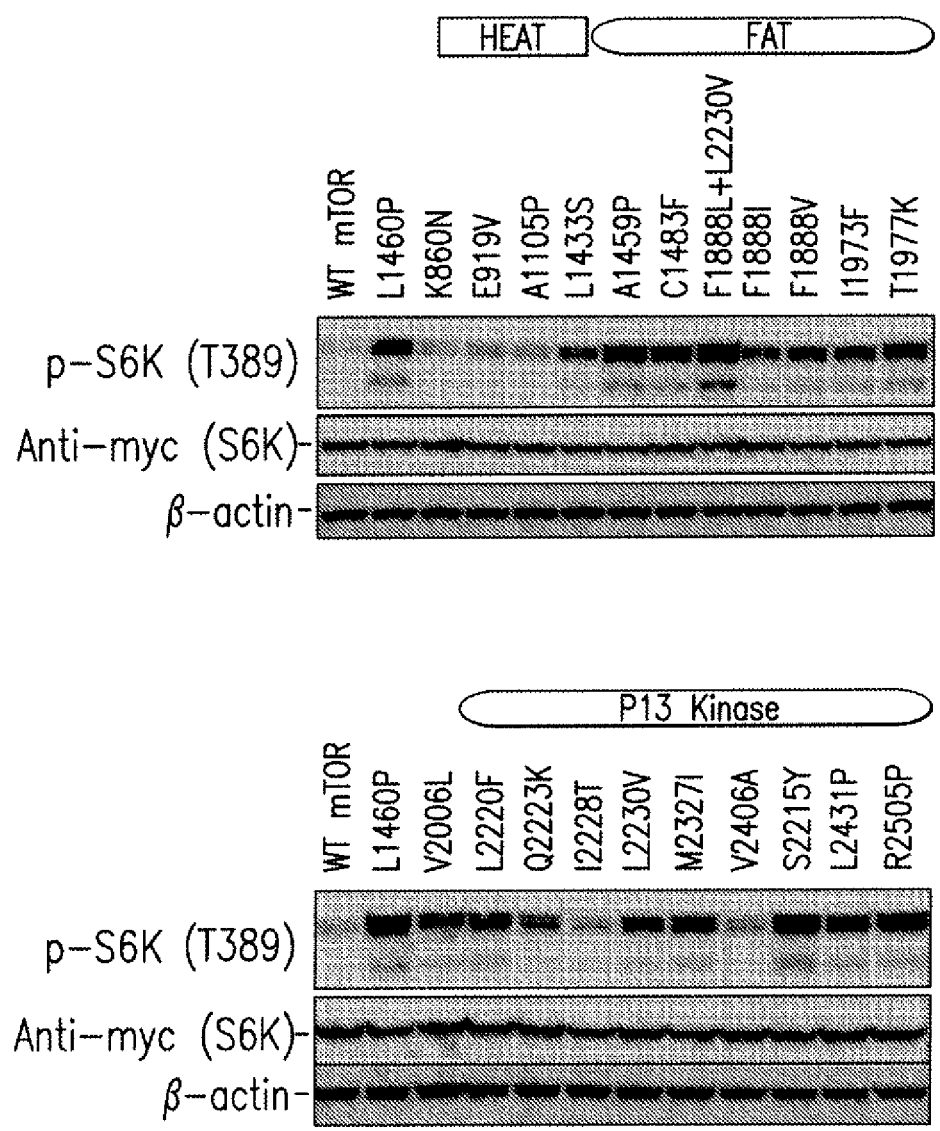
Figure 14C:
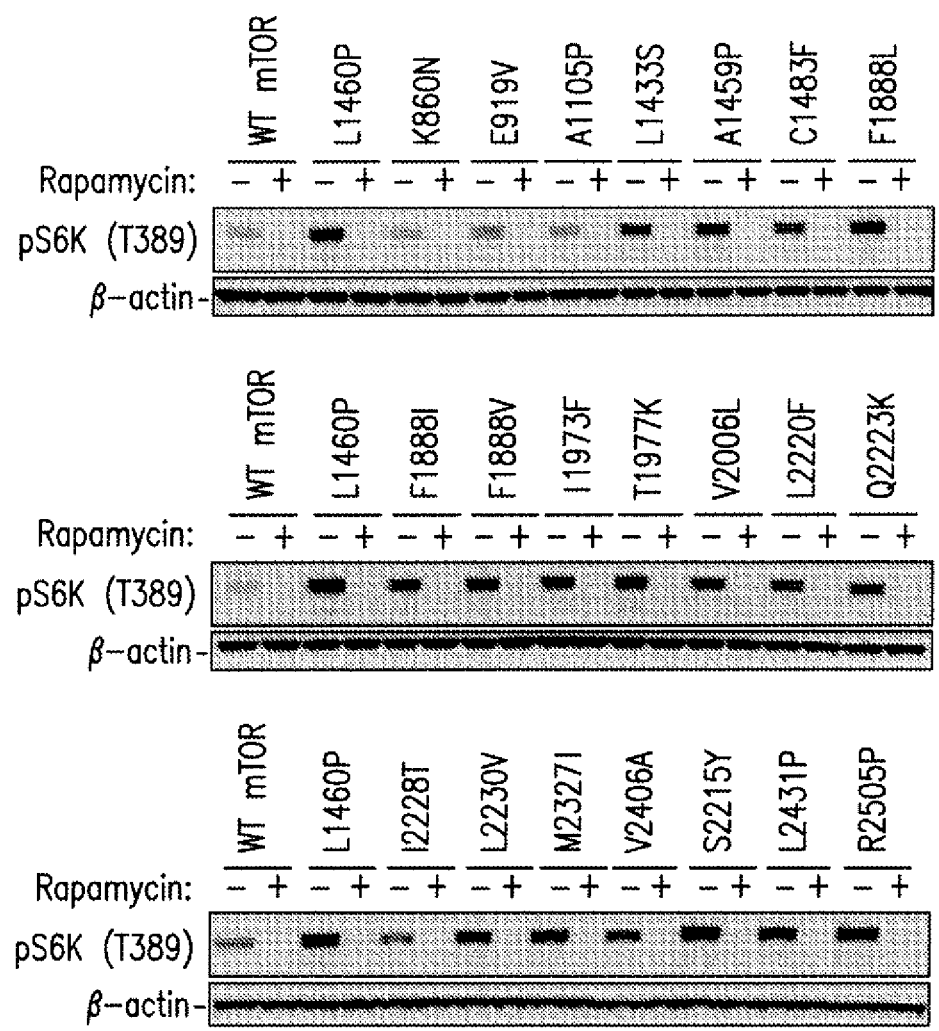

FIG. 14A-C. Clustered mTOR activating mutations in kidney cancer in MSKCC, COSMIC, and KIRC TCGA datasets. (A) Schematics depict the highly similar localizations between human mTOR mutations identified in kidney cancer and yeast Tort gain-of-function mutations identified in a genetic screen. (B) 293T cells were co-transfected with Myc-S6K and the indicated Flag-mTOR constructs, and 24 hours later, washed with serum free medium, and then exposed to serum (10%) containing medium for 1 hour prior to harvest. Cellular lysates were analyzed with the indicated antibodies. The T389 phosphorylation of S6K was quantified. Corresponding regions of the mTOR protein are shown above the respective blots. (C) Cells were transfected and treated as described in (B), in the absence (−) or presence (+) of 50 nM of rapamycin during the last hour prior to harvest for immunoblot analyses.

FIG. 15A-D. Pertinent genetic findings discovered on patients #1 to #4 (A-D) are illustrated as braided cancer rivers to model both genetic divergence and pathway convergence during cancer evolutions in given patients. T, R, and M denote primary tumor, region, and metastasis, respectively.

Figure 16:
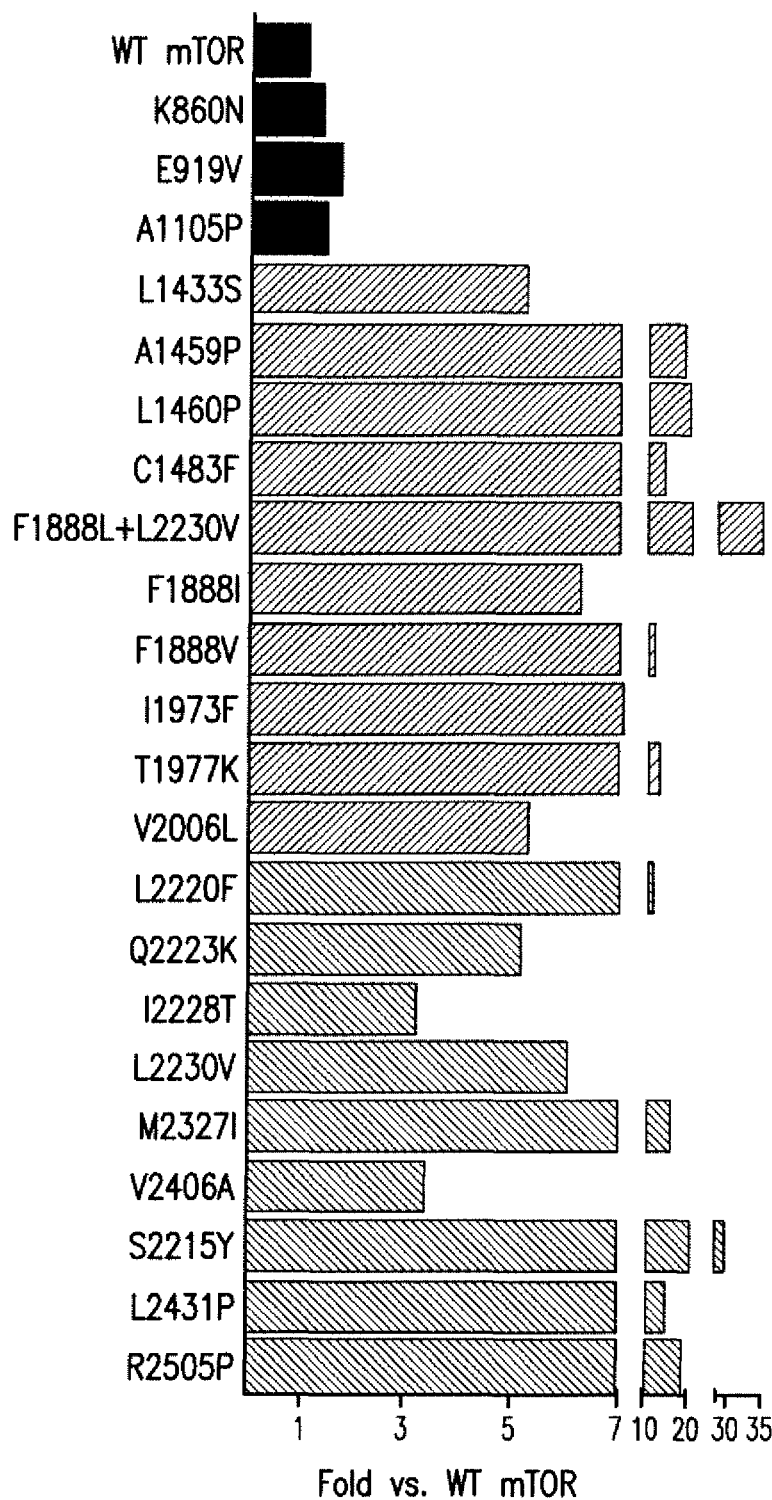

FIG. 16. Bar graph depicts the relative activity of mTORC1, comparing individual mTOR mutants to Wild-type mTOR, based on S6K (T389) phosphorylation.

Figure 17:
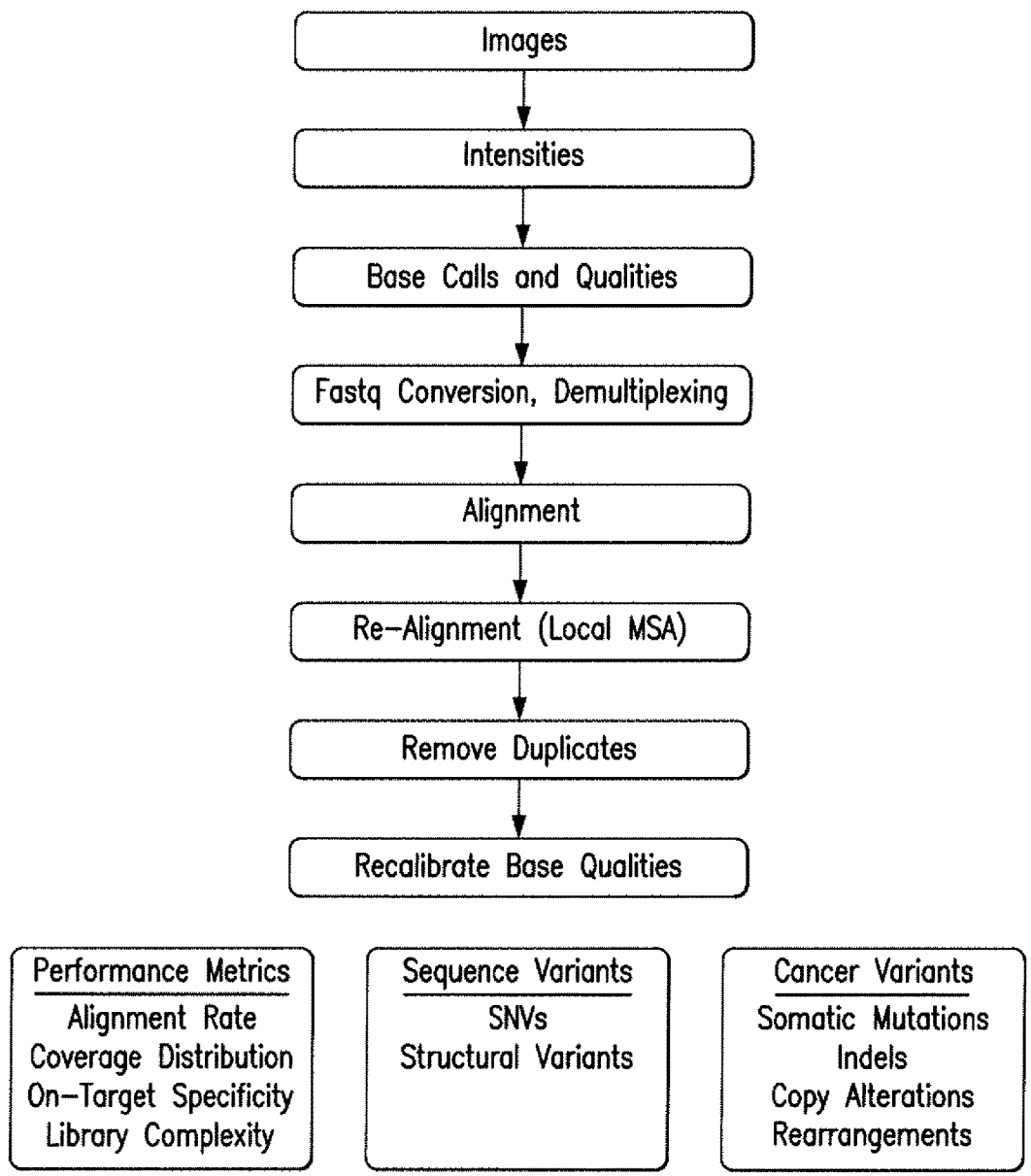

FIG. 17. Flow chart depicts the IMPACT assay mutation identification and filtering algorithm.

Figure 18:
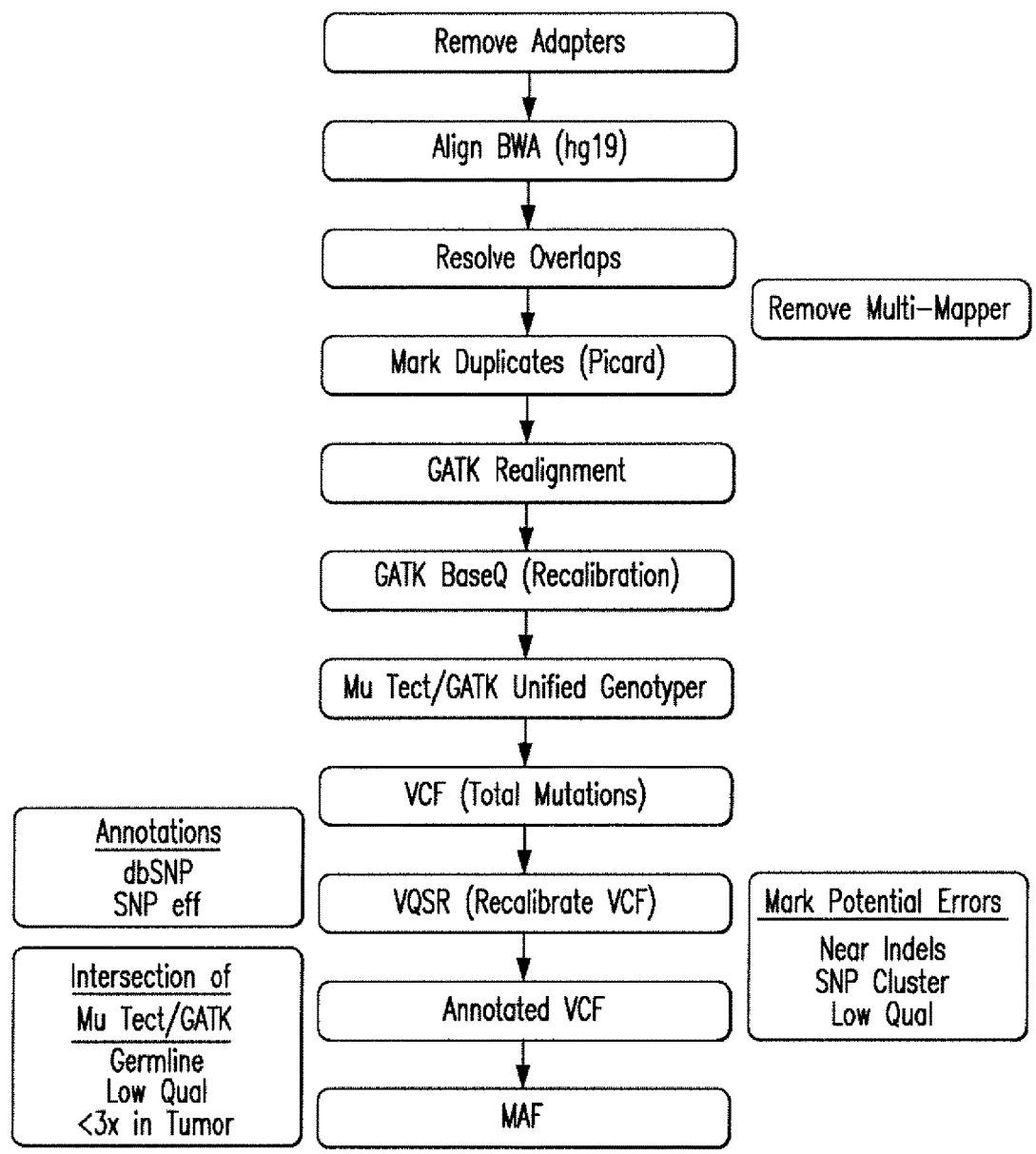

FIG. 18. Flow chart depicts the WEC assay mutation identification and filtering algorithm.

Figure 19:
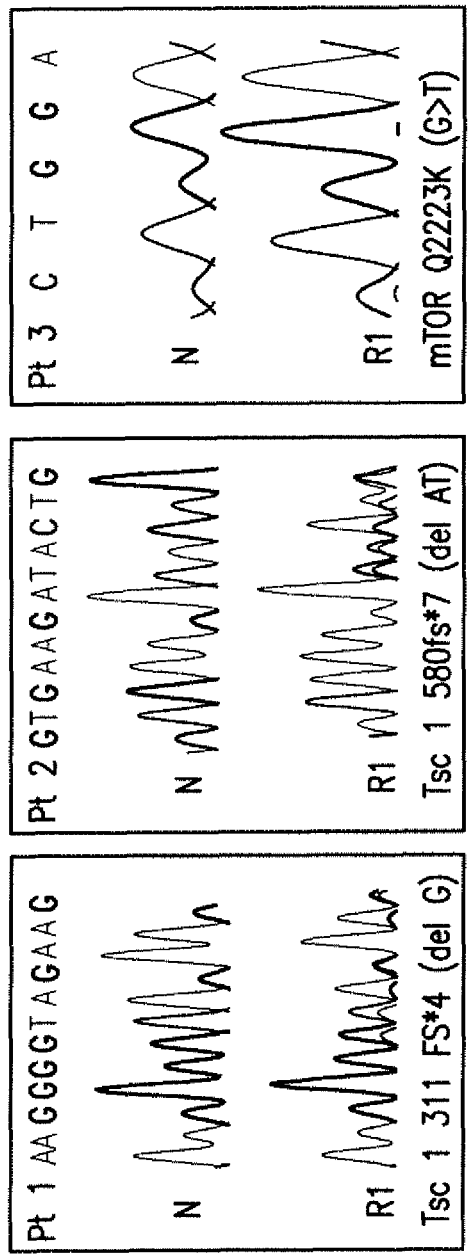

FIG. 19. Sanger validations of mutations in mTORC1 pathway indentified by IMPACT.

Figure 20:
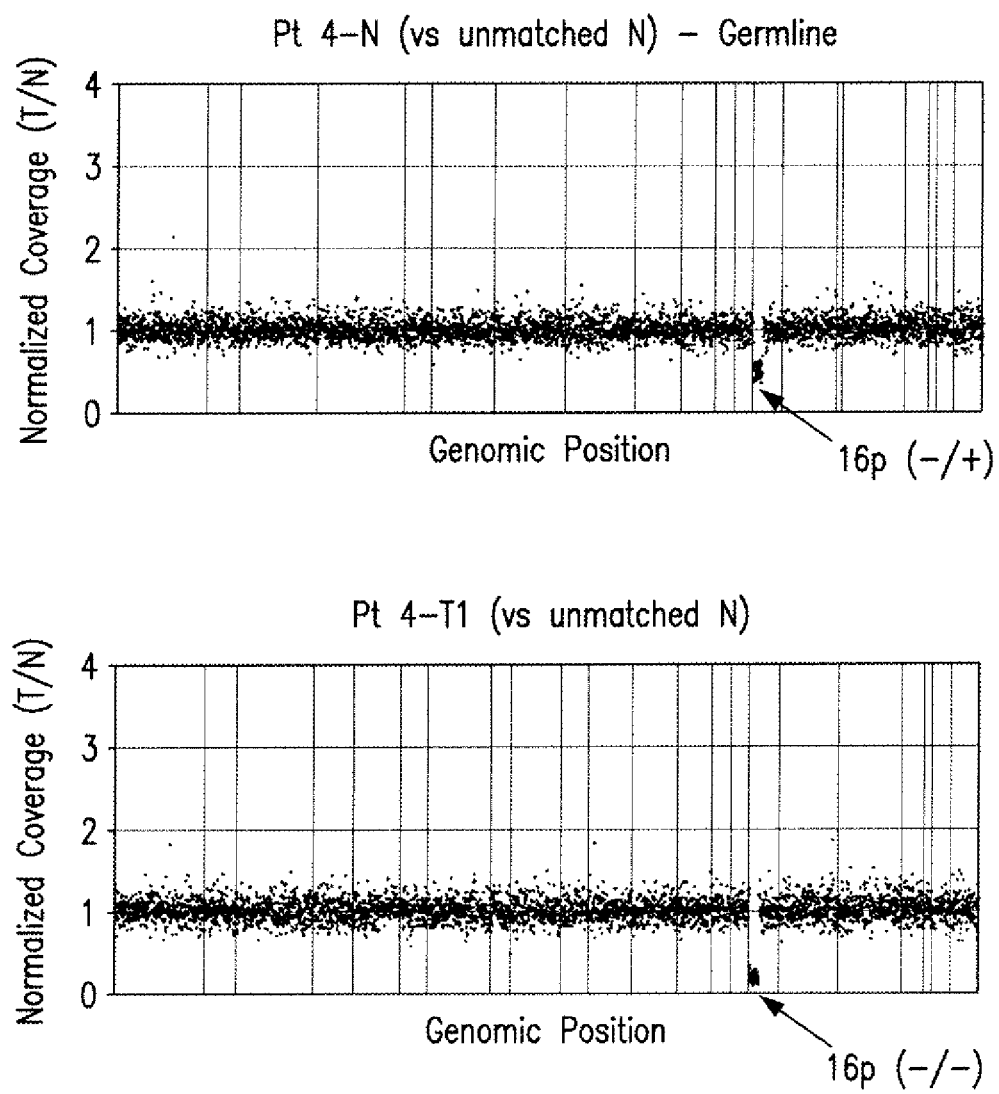

FIG. 20. Copy number plots for patient #4 showing inherited one copy loss of TSC2 in the germline DNA and the current somatic loss (homozygous deletion) in the tumor.

FIG. 21. Sanger validations of additional mutations in the mTORC1 pathway identified by IMPACT assays in patients #1, #3, and #4. Nucleotide changes are circled in red.

Figure 22:
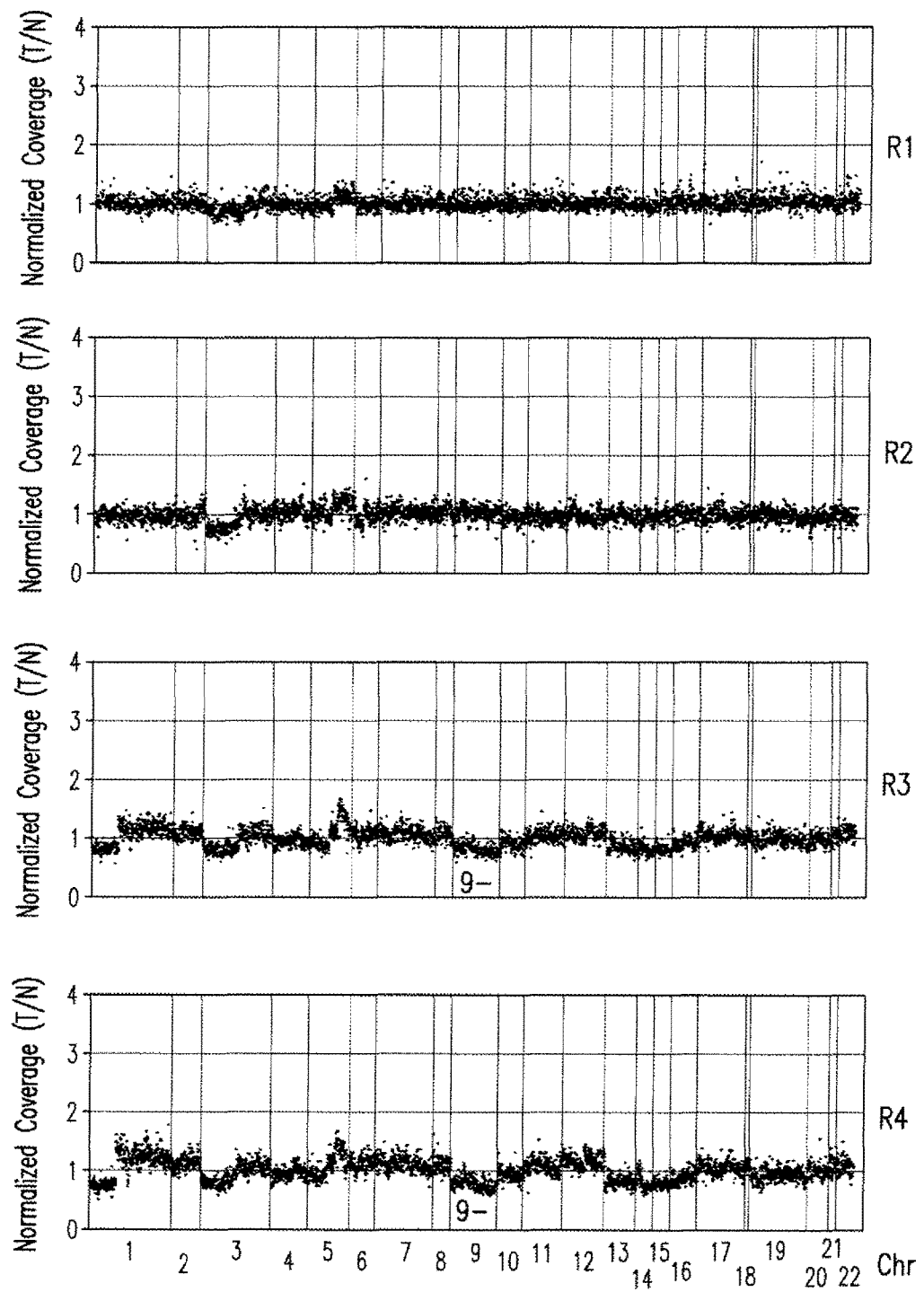

FIG. 22. Copy number plots for multiple tumor regions in patient #3 showing the loss of chromosome 9 only in tumor regions (R3, R4) carrying the TSC1 nonsense mutation.

Figure 23:
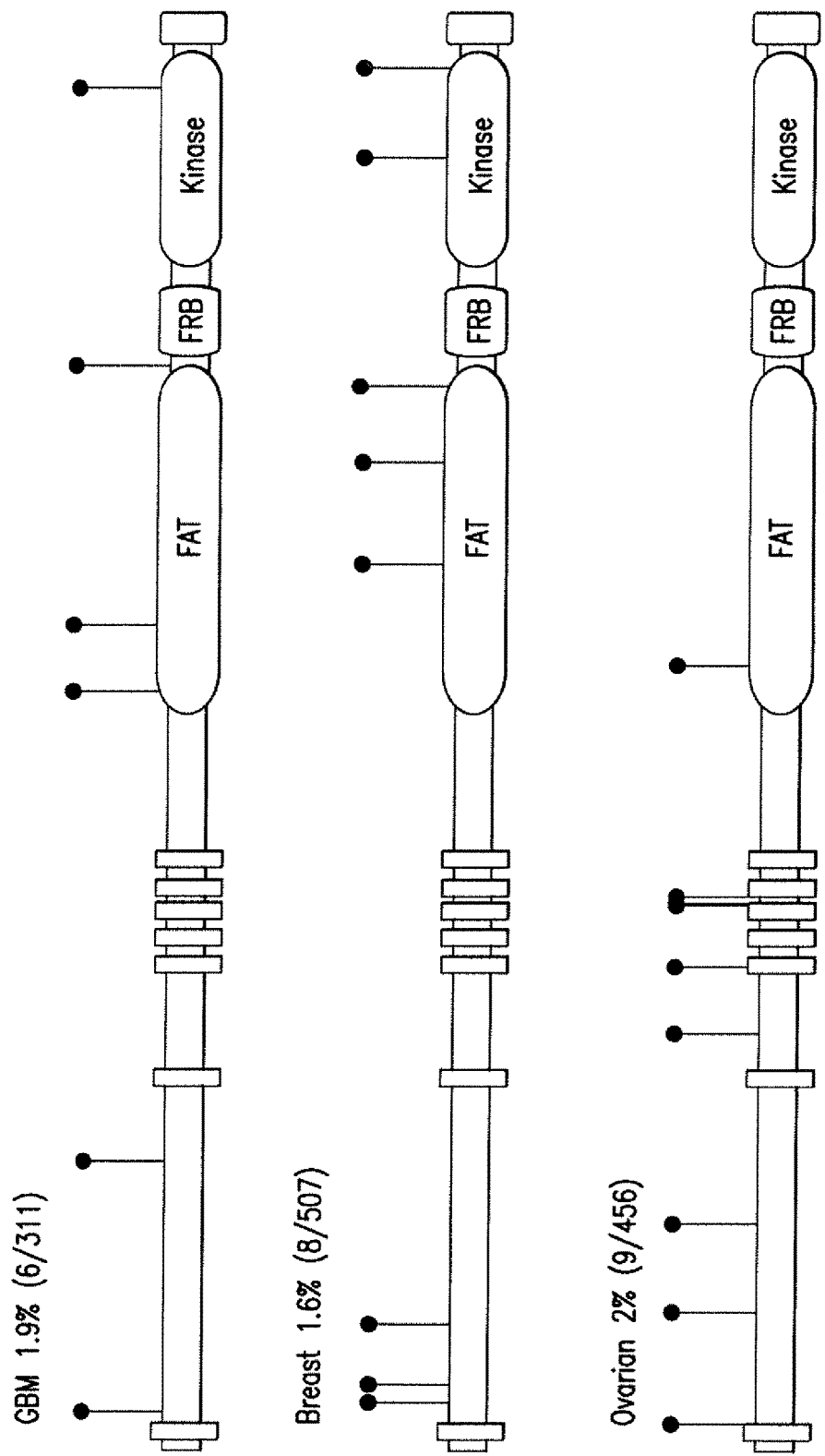
Figure 23:
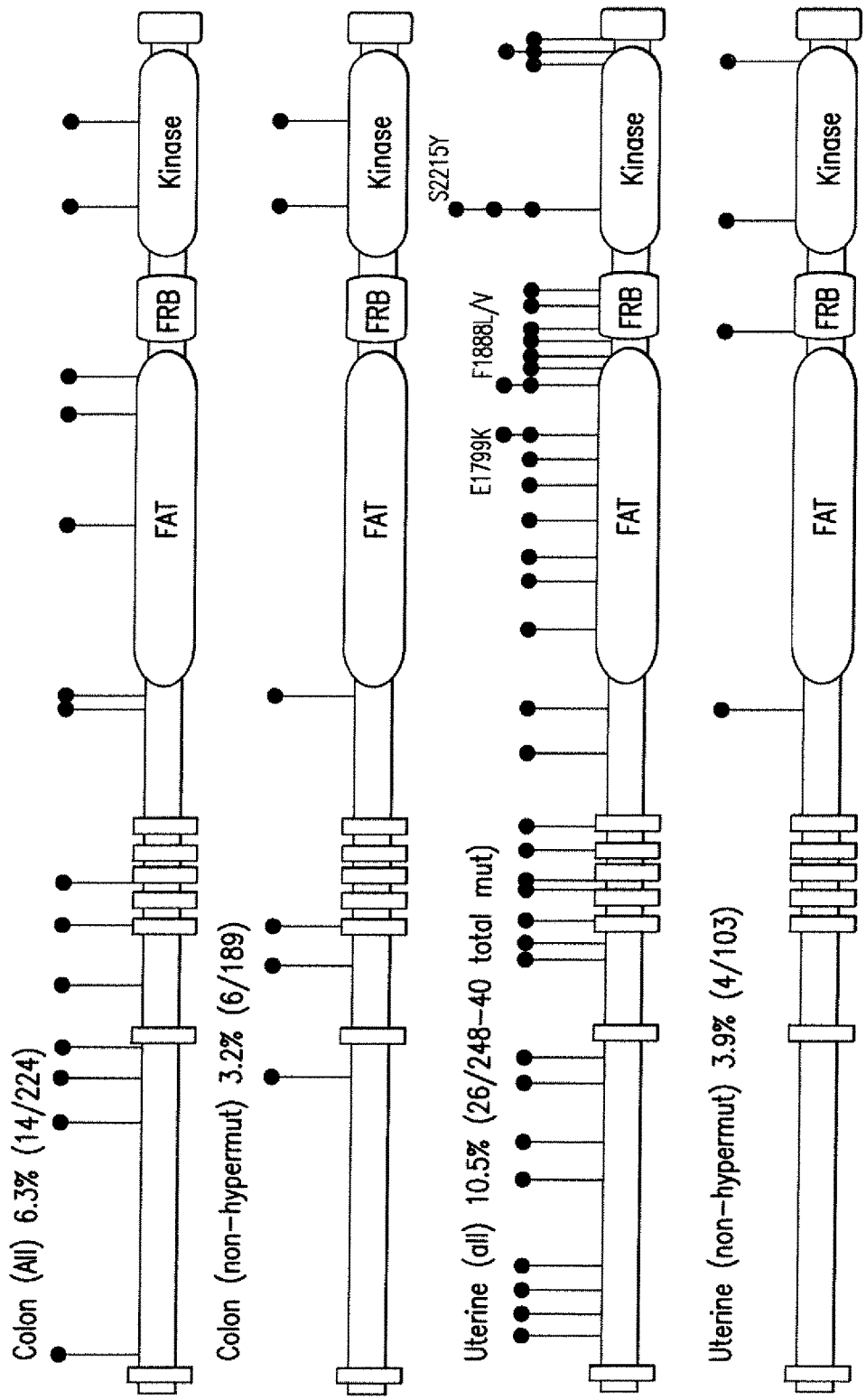

FIG. 23. Gene maps of mTOR mutations across published TCGA cancer studies.

Figure 24:
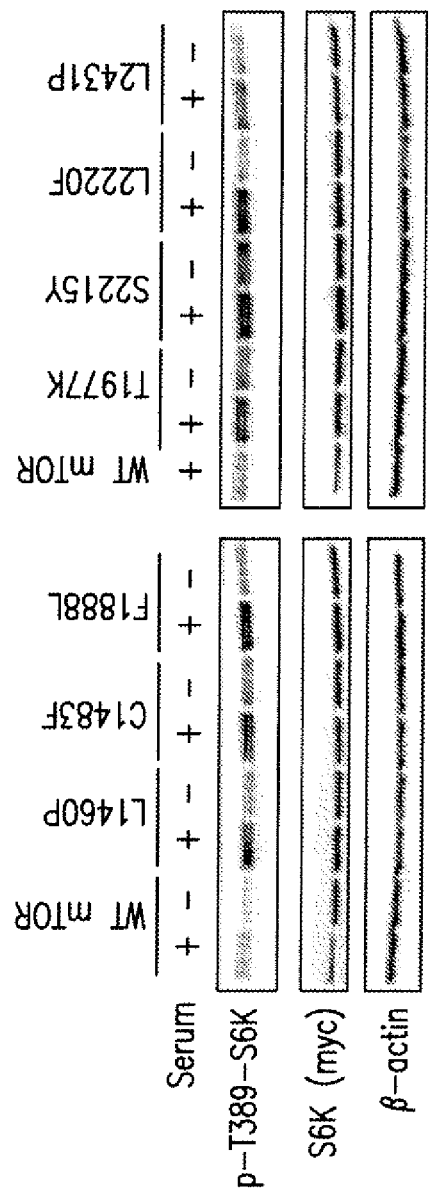

FIG. 24. mTOR mutants associated with therapeutic response to rapalogs are more resistant to serum than wild-type mTOR. Hela cells, transfected with the indicated Flag-mTOR constructs, were cultured either without serum (−) or in the presence of 10% serum (+) for 1 hour. Cellular lysates were then subjected to immunoblot analysis using the indicated antibodies.

Figure 25:
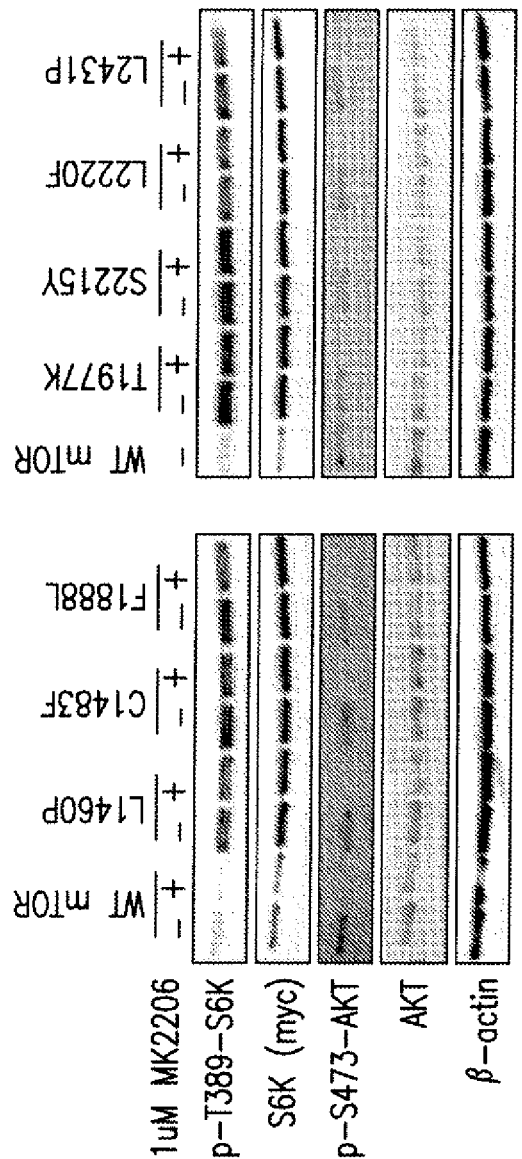

FIG. 25. mTOR mutants associated with therapeutic response to rapalogs are more resistant to AKT inhibitor than wild-type mTOR. Hela cells, transfected with the indicated FlagmTOR constructs, were cultured in medium with (+) or without (−) 1 μM MK2206, an AKT inhibitor for 2 hours. Cellular lysates were then subjected to immunoblot analysis using the indicated antibodies.

Figure 26:
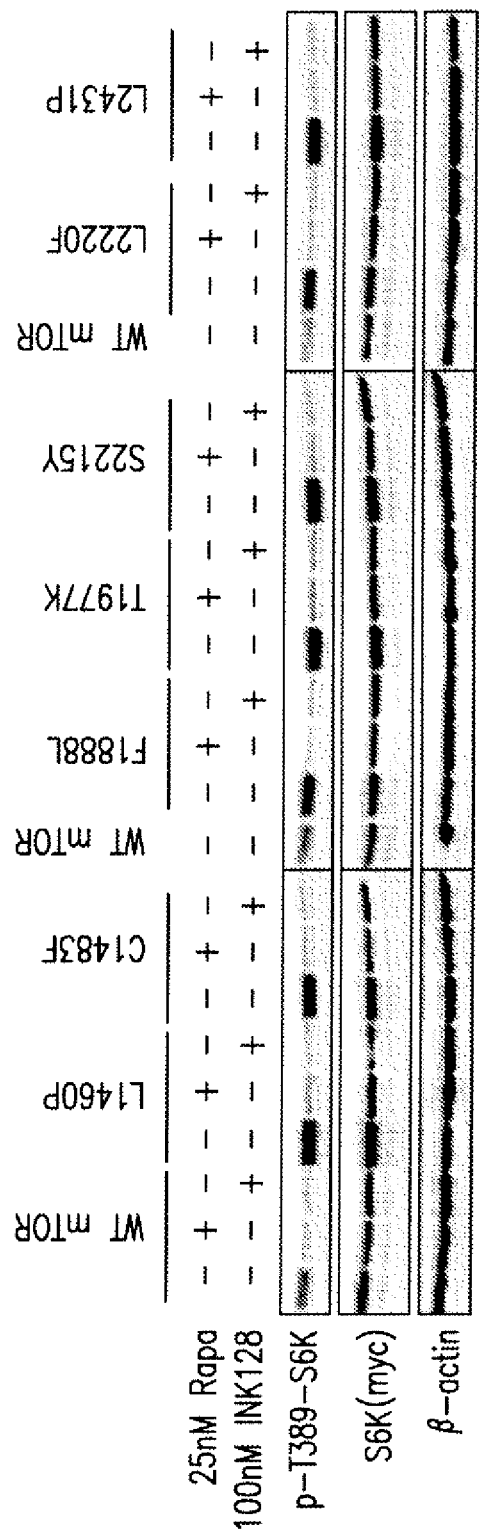

FIG. 26. mTOR mutants associated with therapeutic response to rapalogs are sensitive to rapamycin or to INK128, an ATP-competitive inhibitor of mTORC1 and mTORC2. Hela cells, transfected with the indicated Flag-mTOR constructs, were cultured in medium with (+) or without (−) 25 nM rapamycin or 100 nM INK128 for 2 hours. Cellular lysates were then subjected to immunoblot analysis using the indicated antibodies.

FIG. 27A-D, F1881L/L2230 double mutation has a synergistic effect at increasing mTOR activity. (A) Phosphorylation of S6K in the presence of single F1881L and L2230V mutations. (B) Phosphorylation of S6K where both mutations are present (other single mutants shown for comparison). (C) Phosphorylation of S6K in cells bearing the double mutant, relative to wild-type control, when serum starved for 1, 3, 6 or 20 hours. (D) Phosphorylation of S6K in cells bearing the double mutant in serum-free medium relative to wild-type and single mutants, compared with cells grown in PBS.

5. DETAILED DESCRIPTION OF THE INVENTION

The detailed description of the invention is divided into the following subsections for clarity and not by way of limitation:

(i) biomarkers and methods of measurement;
(ii) TSC biomarkers;
(iii) mTOR biomarkers;
(iv) cancer targets;
(v) rapamycin analogs;
(vi) methods of use; and
(vii) kits.

5.1 Biomarkers and Methods of Measurement

Biomarkers, as that term is used herein, includes nucleic acid, protein, and/or chromosomal markers (i) disclosed below and/or (ii) that are related to the activity level of mTOR, of which rapamycin analogs are inhibitors, in a subject. In certain non-limiting embodiments, a biomarker is an allelic variant or mutation of the version of the gene or protein present in a given population.

A subject may be a human or a non-human subject. Non-limiting examples of non-human subjects include non-human primates, dogs, cats, mice, rats, guinea pigs, rabbits, fowl, pigs, horses, cows, goats, sheep, etc.

A biomarker may be a nucleic acid. Methods of detecting a biomarker which is a nucleic acid include but are not limited to polymerase chain reaction, in situ hybridization (for example but not limited to Fluorescent In Situ Hybridization ("FISH")), gel electrophoresis, sequencing and sequence analysis, and microarray analysis.

A biomarker may be a protein. Methods of detecting a biomarker which is a protein include but are not limited to mass spectrometry techniques, 1-D or 2-D gel-based analysis systems, chromatography, enzyme linked immunosorbent assays (ELISAs), radioimmunoassays (RIA), enzyme immunoassays (EIA), Western Blotting, immunoprecipitation, and immunohistochemistry. Antibody arrays or protein chips may also be employed.

A biomarker may be a chromosome or a chromosome fragment. Methods of detecting a biomarker which is a chromosome or a chromosome fragment include but are not limited to karyotyping and fluorescent in situ hybridization (FISH).

In certain non-limiting embodiments of the invention, a biomarker may be assessed for its effect on mTOR function. For example, the activity of mTOR may be evaluated in a cell, which may or may not be a cancer cell, containing the biomarker. As one non-limiting example, as illustrated in the working examples below, mTOR activity is reflected by phosphorylation of S6K at T389. The level of mTOR function in a cell or cells containing the biomarker may be compared to the level of mTOR function in the absence of the biomarker.

In certain non-limiting embodiments of the invention, a biomarker may be assessed for its effect on TSC1 and/or TSC2 function. For example, the activity of TSC1 and/or TSC2 may be evaluated in a cell containing the TSC1 or TSC2 biomarker. In a certain non-limiting embodiment, the activity of TSC1 and/or TSC2 may be evaluated by evaluating mTOR function, where the activity of TSC1 and/or TSC2 is/are inversely proportional to the activity of mTOR. The level of TSC1 and/or TSC2 function in a cell or cells containing the TSC1 or TCS2 biomarker may be compared to the level of TSC1 and/or TSC2 function in a cell or cells having a different type of TSC1 or TSC2.

A healthy control level of mTOR function (healthy control activity) may be established using a non-cancer cell or cells from a healthy control subject.

A healthy control level of TSC1 and/or TSC2 function (healthy control activity) may be established using a non-cancer cell or cells from a healthy control subject.

5.2 TSC Biomarkers

Tuberous sclerosis 1 protein is denoted TSC1 herein.
Tuberous sclerosis 2 protein is denoted TSC2 herein.

In a specific non-limiting embodiment, a reference TSC1 molecule is a human TSC1 nucleic acid molecule which has the nucleic acid sequence as set forth in NCBI database accession no. NM_000368 or a TSC1 protein molecule which has the amino acid sequence as set forth in NCBI database accession no. NP_000359. The functional activity of a TSC1 protein having the foregoing amino acid sequence is referred to as a human TSC1 reference control activity.

In a specific non-limiting embodiment, a reference TSC2 molecule is a human TSC2 nucleic acid molecule which has the nucleic acid sequence as set forth in NCBI database accession no. NM_000548 or a TSC2 protein molecule which has the amino acid sequence as set forth in NCBI database accession no. NP_000539. The functional activity of a TSC2 protein having the foregoing amino acid sequence is referred to as a human TSC2 reference control activity.

Reference TSC1 and/or TSC2 nucleic acids and proteins for non-human species are known or can be determined according to methods known in the art, for example where the reference sequence is the allele represented in the majority of a population.

Where comparisons to a reference control activity are referred to herein, the biomarker is assessed relative to the reference control activity within the same species. For example, a human TSC1 biomarker activity is compared with a human TSC1 reference control activity.

A TSC1 biomarker is a biomarker which manifests as reduced TSC1 function relative to a TSC1 reference control activity or a TSC1 healthy control activity and/or increased mTOR function relative to a mTOR reference control activity or a mTOR healthy control activity.

A TSC2 biomarker is a biomarker which manifests as reduced TSC2 function relative to a TSC2 reference control activity and/or increased mTOR function relative to a mTOR reference control activity.

In certain non-limiting embodiments a TSC1 or TSC2 biomarker is a nucleic acid bearing an insertion, deletion, or substitution relative to a reference TSC1 or TSC2 gene, or a protein encoded by said nucleic acid. Said insertion, deletion, or substitution may result in a nonsense mutation, a frameshift mutation, a missense mutation, or a termination relative to protein expression.

In certain non-limiting embodiments a TSC1 or TSC2 biomarker is a protein bearing an insertion, deletion, or substitution relative to a reference TSC1 or TSC2 protein.

In certain non-limiting embodiments a TSC1 or TSC2 biomarker is a chromosome bearing a deletion, substitution, duplication or inversion which includes the TSC1 or TSC2 locus.

In one specific non-limiting embodiment, a TSC1 biomarker for a human subject is the P311fs*4 frameshift mutation.

In one specific non-limiting embodiment, a TSC1 biomarker for a human subject is the I580fs*7 frameshift mutation.

In one specific non-limiting embodiment, a TSC1 biomarker for a human subject is the Q527* nonsense mutation.

In one specific non-limiting embodiment, a TSC1 biomarker for a human subject is the Q781* nonsense mutation.

In one specific non-limiting embodiment, a TSC1 biomarker for a human subject is the S334* nonsense mutation.

In one specific non-limiting embodiment, a TSC2 biomarker for a human subject is the Q794* nonsense mutation.

In one specific non-limiting embodiment, a TSC2 biomarker for a human subject is the R611W missense mutation.

In one specific non-limiting embodiment, a TSC2 biomarker for a human subject is the S1498N missense mutation.

In one specific non-limiting embodiment, a TSC1 biomarker for a human subject is a chromosomal abnormality involving chromosome position 9q34.

For example, the chromosomal abnormality may be an insertion, deletion, duplication, inversion, etc. of one or both chromosome(s) including or in immediate proximity to position 904.

In one specific non-limiting embodiment, a TSC2 biomarker for a human subject is a chromosomal abnormality involving chromosome position 16p13. For example, the chromosomal abnormality may be an insertion, deletion, duplication, inversion, etc. of one or both chromosome(s) including or in immediate proximity to position 16p13.

5.3 mTOR Mutations

Mammalian target of rapamycin is denoted mTOR herein and is also known as FRAP (FKBP12-rapamcyin-associated protein), RAFT1 (rapamycin and FKBP12 target), RAPT 1 (rapamycin target 1), or SEP (sirolimus effector protein).

In a specific non-limiting embodiment, a reference mTOR molecule is a human mTOR nucleic acid molecule which has the nucleic acid sequence as set forth in NCBI database accession no. NM_004958 or a mTOR protein molecule which has the amino acid sequence as set forth in NCBI database accession no. NP_004949. The functional activity of a mTOR protein having the foregoing amino acid sequence is referred to as a human mTOR reference control activity Reference mTOR nucleic acids and proteins for non-human species are known or can be determined according to methods known in the art, for example where the reference sequence is the allele represented in the majority of a population.

A mTOR biomarker is a biomarker which manifests as increased mTOR function and/or activity relative to a mTOR reference control activity or a mTOR healthy control activity. In certain non-limiting embodiments, an increase in mTOR function and/or activity is manifested as (i.e., indicated by) an increase in phosphporylation of S6K, for example at residue T389, relative to reference (e.g., wild type) mTOR. In certain non-limiting embodiments, an increase in mTOR function and/or activity is manifested as increased growth in serum-depleted medium (for example, medium containing less than or equal to 2 percent serum, medium containing less than or equal to 1 percent serum or serum-free medium) relative to reference (e.g. wild type) mTOR. In certain non-limiting embodiments, an increase in mTOR function and/or activity is manifested as increased resistance to AKT inhibition relative to reference (e.g., wild type) mTOR. In certain non-limiting embodiments, an increase in mTOR function and/or activity is manifested as the ability to be inhibited by (that is to say, sensitivity to) rapamycin and/or INK128.

In certain non-limiting embodiments, a mTOR biomarker may be associated with one or more, or two or more, or three or more, or four or more, of the following indicators of increased activity: an increase in phosphporylation of S6K, for example at residue T389, relative to wild type mTOR; increased growth in serum-depleted medium relative to wild type mTOR; increased resistance to AKT inhibition relative to wild type mTOR: and/or the ability to be inhibited by (that is to say, sensitivity to) rapamycin and/or INK128.

A mTOR protein comprising one or more of the biomarkers disclosed herein may further comprise additional variations from the wild-type sequence.

In certain non-limiting embodiments a mTOR biomarker is a nucleic acid hearing one or more mutation, which may be an insertion, deletion, or substitution relative to the reference mTOR gene, or a protein encoded by said nucleic acid. Said insertion, deletion, or substitution may result in a nonsense mutation, a frameshift mutation, a missense mutation, or a termination relative to protein expression.

In certain non-limiting embodiments a mTOR biomarker is a protein bearing one or more mutation, which may be an insertion, deletion, or substitution relative to the mTOR reference protein.

In certain non-limiting embodiments a mTOR biomarker is a chromosome bearing one or more mutation, which may be an insertion, deletion, substitution, duplication or inversion which includes the mTOR gene.

In the following description of mTOR biomarkers, amino acid numbering is based on the amino acid sequence set forth as NCBI Accession No. NP_004949.

In one specific non-limiting embodiment, a mTOR biomarker for a human subject is a Q2223 mutation.

In one specific non-limiting embodiment, a mTOR biomarker for a human subject is a 82505 mutation.

In one specific non-limiting embodiment, a mTOR biomarker for a human subject is a L2431 mutation.

In one specific non-limiting embodiment, a mTOR biomarker for a human subject is a 52215 mutation.

In one specific non-limiting embodiment, a mTOR biomarker for a human subject is a V2406 mutation.

In one specific non-limiting embodiment, a mTOR biomarker for a human subject is a M2327 mutation.

In one specific non-limiting embodiment, a mTOR biomarker for a human subject is a L2230 mutation.

In one specific non-limiting embodiment, a mTOR biomarker for a human subject is a I2228 mutation.

In one specific non-limiting embodiment, a mTOR biomarker for a human subject is a L2220 mutation.

In one specific non-limiting embodiment, a mTOR biomarker for a human subject is a V2006 mutation.

In one specific non-limiting embodiment, a mTOR biomarker for a human subject is a T1977 mutation.

In one specific non-limiting embodiment, a mTOR biomarker for a human subject is a 11973 mutation.

In one specific non-limiting embodiment, a mTOR biomarker for a human subject is a F1888 mutation.

In one specific non-limiting embodiment, a mTOR biomarker for a human subject is a F1888 mutation.

In one specific non-limiting embodiment, a mTOR biomarker for a human subject is a F1888 mutation.

In one specific non-limiting embodiment, a mTOR biomarker for a human subject is a F1888 mutation in combination with a L2230 mutation.

In one specific non-limiting embodiment, a mTOR biomarker for a human subject is a C1483 mutation.

In one specific non-limiting embodiment, a mTOR biomarker for a human subject is a L1460 mutation.

In one specific non-limiting embodiment, a mTOR biomarker for a human subject is a A1459 mutation.

In one specific non-limiting embodiment, a mTOR biomarker for a human subject is a L1433 mutation.

In one specific non-limiting embodiment, a mTOR biomarker for a human subject is a A1105 mutation.

In one specific non-limiting embodiment, a mTOR biomarker for a human subject is a E919 mutation.

In one specific non-limiting embodiment, a mTOR biomarker for a human subject is a K860 mutation.

In one specific non-limiting embodiment, a mTOR biomarker for a human subject is a 12500 mutation.

In one specific non-limiting embodiment, a mTOR biomarker for a human subject is a K1452 mutation.

In one specific non-limiting embodiment, a mTOR biomarker for a human subject is a Y1463 mutation.]

In one specific non-limiting embodiment, a mTOR biomarker for a human subject is the Q2223K frameshift mutation.

In one specific non-limiting embodiment, a mTOR biomarker for a human subject is the R2505P mutation.

In one specific non-limiting embodiment, a mTOR biomarker for a human subject is the L2431P mutation.

In one specific non-limiting embodiment, a mTOR biomarker for a human subject is the S2215F mutation.

In one specific non-limiting embodiment, a mTOR biomarker for a human subject is the V2406A mutation.

In one specific non-limiting embodiment, a mTOR biomarker for a human subject is the M2327I mutation.

In one specific non-limiting embodiment, a mTOR biomarker for a human subject is the L2230V mutation.

In one specific non-limiting embodiment, a mTOR biomarker for a human subject is the I2228T mutation.

In one specific non-limiting embodiment, a mTOR biomarker for a human subject is the L2220F mutation.

In one specific non-limiting embodiment, a mTOR biomarker for a human subject is the V2006L mutation.

In one specific non-limiting embodiment, a mTOR biomarker for a human subject is the T1977K mutation.

In one specific non-limiting embodiment, a mTOR biomarker for a human subject is the I1973F mutation.

In one specific non-limiting embodiment, a mTOR biomarker for a human subject is the F1888V mutation.

In one specific non-limiting embodiment, a mTOR biomarker for a human subject is the F1888I mutation.

In one specific non-limiting embodiment, a mTOR biomarker for a human subject is the F1888L mutation.

In one specific non-limiting embodiment, a mTOR biomarker for a human subject is the F1888L mutation in combination with the L2230V mutation.

In one specific non-limiting embodiment, a mTOR biomarker for a human subject is the C1483F or the C1483Y mutation.

In one specific non-limiting embodiment, a mTOR biomarker for a human subject is the L1460P mutation.

In one specific non-limiting embodiment, a mTOR biomarker for a human subject is the A1459P mutation.

In one specific non-limiting embodiment, a mTOR biomarker for a human subject is the L1433S mutation.

In one specific non-limiting embodiment, a mTOR biomarker for a human subject is the A1105P mutation.

In one specific non-limiting embodiment, a mTOR biomarker for a human subject is the E919V mutation.

In one specific non-limiting embodiment, a mTOR biomarker for a human subject is the K860N mutation. A mTOR biomarker of the invention may comprise more than one of the above-listed mutations.

In certain non-limiting embodiments, a mTOR biomarker involves a mutation in a FAT or KINASE domain of mTOR.

In certain non-limiting embodiments, a mTOR biomarker is one or more mutation in the FAT domain of mTOR, for example, which increases mTOR activity. In certain non-limiting embodiments, the mutation in the FAT domain is a mutation of one or more residue of amino acid residues 1382-1982 of the amino acid sequence set forth in NCBI Accession No. NP_004949. In certain non-limiting embodiments, the mutated sequence is at least 95 or at least 98 or at least 99 or at least 99.5 percent homologous to the wild-type sequence (as determined, for example, by standard software such as BLAST or FASTA). In certain non-limiting embodiments, the mutation in the FAT domain is a mutation of one or more residue of amino acid residues of the following amino acid sequence which represents residues 1382-1982:

```
                                             (SEQ ID NO: 1)
LLGERAAKC RAYAKALHYK ELEFQKGPTP AILESLISIN

NKLQQPEAAA GVLEYAMKHF GELEIQATWY EKLHEWEDAL

VAYDKKMDTN KDDPELMLGR MRCLEALGEW GQLHQQCCEK

WTLVNDETQA KMARMAAAAA WGLGQWDSME EYTCMIPRDT

HDGAFYRAVL ALHQDLFSLA QQCIDKARDL LDAELTAMAG

ESYSRAYGAM VSCHMLSELE EVIQYKLVPE RREIIRQIWW

ERLQGCQRIV EDWQKILMVR SLVVSPHEDM RTWLKYASLC

GKSGRLALAH KTLVLLLGVD PSRQLDHPLP TVHPQVTYAY

MKNMWKSARK IDAFQHMQHF VQTMQQQAQH AIATEDQQHK

QELHKLMARC FLKLGEWQLN LQGINESTIP KVLQYYSAAT

EHDRSWYKAW HAWAVMNFEA VLHYKHQNQA RDEKKKLRHA

SGANITNATT AATTAATATT TASTEGSNSE SEAESTENSP

TPSPLQKKVT EDLSKTLLMY TVPAVQGFFR SISLSRGNNL

QDTLRVLTLW FDYGHWPDVN EALVEGVKAI QIDTWLQVIP

QLIARIDTPR PLVGRLIHQL LTDIGRYHPQ ALIYPLTVAS KS.
```

In certain non-limiting embodiments, the mutation in the FAT domain is a mutation of one or more residue of amino acid residues 1400-1500 of the amino acid sequence set forth in NCBI Accession No. NP_004949. In certain non-limiting embodiments, the mutation in the FAT domain is a mutation of one or more residue of amino acid residues of the following amino acid sequence which represents residues 1400-1500:

```
                                             (SEQ ID NO: 2)
K ELEFQKGPTP AILESLISIN NKLQQPEAAA GVLEYAMKHF

GELEIQATWY EKLHEWEDAL VAYDKKMDTN KDDPELMLGR

MRCLEALGEW GQLHQQCCEK,
```

In certain non-limiting embodiments, the mutation in the FAT domain is a mutation of one or more residue of amino acid residues 1850-1982 of the amino acid sequence set forth in NCBI Accession No, NP_004949. In certain non-limiting embodiments, the mutation in the FAT domain is a mutation of one or more residue of amino acid residues of the following amino acid sequence which represents residues 1850-1982:

```
                                            (SEQ ID NO: 3)
E SEAESTENSP TPSPLQKKVT EDLSKTLLMY TVPAVQGFFR

SISLSRGNNL QDTLRVLTLW FDYGHWPDVN EALVEGVKAI

QIDTWLQVIP QLIARIDTPR PLVGRLIHQL LTDTGRYHPQ

ALIYPLTVAS KS.
```

In certain non-limiting embodiments, the mutation in the FAT domain is a mutation of L1433, a mutation of A1459, a mutation of L1460, a mutation of C1483, a mutation of F1888, a mutation of 11973, a mutation of T1977, or a combination thereof. In certain non-limiting embodiments, the mutation is one or more of L1433S, A1459P, L1460P, C1483F, C1483Y, F1888L, I or V, I1973F, or T1977K.

In certain non-limiting embodiments, a mTOR biomarker is one or more mutation in the PI3 kinase domain of mTOR, for example, which increases mTOR activity. In certain non-limiting embodiments, the mutation in the PI3 kinase domain is a mutation of one or more residue of amino acid residues 2182-2516 of the amino acid sequence set forth in NCBI Accession No. NP_004949. In certain non-limiting embodiments, the mutated sequence is at least 95 or at least 98 or at least 99 or at least 99.5 percent homologous to the wild-type sequence (as determined, for example, by standard software such as BLAST or FASTA). In certain non-limiting embodiments, the mutation in the PI3 kinase domain is a mutation of one or more residue of amino acid residues of the following amino acid sequence which represents residues 2182-2516:

```
                                            (SEQ ID NO: 4)
FVFLLKGHE DLRQDERVMQ LFGLVNTLLA NDPTSLRKNL

SIQRYAVIPL STNSGLIGWV PHCDTLHALI RDYREKKKIL

LNIEHRIMLR MAPDYDHLTL MQKVEVFEHA VNNTAGDDLA

KLLWLKSPSS EVWFDRRTNY TRSLAVMSMV GYILGLGDRH

PSNLMLDRLS GKILHIDFGD CFEVAMTREK FPEKIPFRLT

RMLTNAMEVT GLDGNYRITC HTVMEVLREH KDSVMAVLEA

FVYDPLLNWR LMDTNTKGNK RSRTRTDSYS AGQSVEILDG

VELGEPAHKK TGTTVPESIH SFIGDGLVKP EALNKKAIQI

INRVRDKLTG RDFSHD.
```

In certain non-limiting embodiments, the mutation in the PI3 kinase domain is a mutation of one or more residue of amino acid residues 2200-2250 of the amino acid sequence set forth in NCBI Accession No. NP*004949. In certain non-limiting embodiments, the mutation in the FAT domain is a mutation of one or more residue of amino acid residues of the following amino acid sequence which represents residues 2200-2250:

```
                                            (SEQ ID NO: 5)
Q LFGLVNTLLA NDPTSLRKNL SIQRYAVIPL STNSGLIGWV

PHCDTLHALI.
```

In certain non-limiting embodiments, the mutation in the PI3 kinase domain is a mutation of L2230, L2220, Q2223, M2327, V2406, 52215, L2431, 82505, or a combination thereof. In certain non-limiting embodiments, the mutation in the PI3 kinase domain is a mutation of L2230, L2220, Q2223, 52215, or a combination thereof. In certain non-limiting embodiments, the mutation is one or more of L2230V, L2220F, Q2223K, M2327I, V2406A, S2215F, L2431P, or R2505P.

Specific non-limiting examples of biomarkers are set forth in FIG. 14B and FIG. 16 herein.

In one specific non-limiting embodiment, a mTOR biomarker for a human subject is a chromosomal abnormality involving chromosome position 1p36. For example, the chromosomal abnormality may be one or more insertion, deletion, duplication, inversion, etc. of one or both chromosome(s) including or in immediate proximity to position 1p36.

In further non-limiting embodiments, a mTOR biomarker is a molecule other than the mTOR gene or protein which increases the activity of mTOR. Non-limiting examples of such mTOR biomarkers include Rheb, Raptor, Deptor, PRAS40, AMPK, REDD1/2, LKB1 and variants or mutations thereof relative to reference sequences. In specific non-limiting embodiments, Deptor, AMPK, LKB1, PRAS40, RED1/2 nucleic acid or protein comprising one or more insertion, deletion, or substitution, which may result in a frameshift, nonsense or missense mutation which decrease the functionality of the subject protein and increase function of mTOR may serve as a mTOR biomarker.

5.4 Cancer Targets

Non-limiting examples of cancers that may be subject to the present invention include renal cell carcinoma (RCC), supependymal giant cell astrocytoma, supependymal giant cell astrocytoma associated with tuberous sclerosis, hormone receptor positive HER-2 negative breast cancer, Hodgkin's lymphoma, non-Hodgkin's lymphoma, endometrial cancer, mantle-cell lymphoma, melanoma, and progressive neuroendocrine tumors of pancreatic origin.

5.5 Rapamycin Analogs

Non-limiting examples of rapamycin analogs include sirolimus and its analogs/derivatives including everolimus, temsirolimus, deforolimus, and zotarolimus.

5.6 Non-Rapamycin mTOR Inhibitors

In certain non-limiting embodiments, cancers that are found to express mTOR biomarkers, where the activity of mTOR is increased relative to wild-type, may be treated with non-rapamycin mTOR inhibitors. Non-limiting examples of such mTOR inhibitors include INK128, AZD8055, AZD2014 and analogs having a morpholino pyrazolopyrimidine scaffold; and mTOR/PI3 kinase dual inhibitors such as, but not limited to, NVP-BEZ235, BGT226, SF1126, PKI-587. The present invention, in non-limiting embodiments, provides for producing an anti-cancer effect in a cancer cell expressing a mTOR biomarker that increases mTOR activity by exposing said cell to an effective amount of a non-rapamycin mTOR activity, and provides for methods of treatment of a subject having a cancer in which said cancer cells are present.

5.7 Methods of Use

In certain non-limiting embodiments, the present invention provides for a method of determining whether an anti-cancer effect is likely to be produced in a cancer by a rapamycin analog, comprising determining whether cells of the cancer contain a biomarker selected from a TSC1 biomarker, a TSC2 biomarker, a mTOR biomarker, and a combination thereof, where if the TSC1, TSC2, and/or mTOR biomarker is present, it is more likely that a rapamycin analog would have an anti-cancer effect on the cancer.

TSC1 biomarkers, TCS2 biomarkers, and mTOR biomarkers are described in the sections above. Cancers suitable for treatment are described above. Rapamycin analogs are described above.

In certain non-limiting embodiments, the present invention provides for a method of producing an anti-cancer effect in a cancer, comprising determining whether cells of the cancer contain a biomarker selected from a TSC1 biomarker, a TSC2 biomarker, a mTOR biomarker, and a combination thereof, and, where a TSC1 biomarker, a TSC2 biomarker, and/or a mTOR biomarker is present, administering a therapeutically effective amount of a rapamycin analog to produce an anti-cancer effect.

An anti-cancer effect means one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, and/or a reduction in tumor metastasis.

In certain non-limiting embodiments, the present invention provides for a method of treating a subject suffering from a cancer, comprising determining whether cells of the cancer contain a biomarker selected from a TSC1 biomarker, a TSC2 biomarker, a mTOR biomarker, and a combination thereof, and, where a TSC1 biomarker, a TCS2 biomarker, and/or a mTOR biomarker is present, treating the subject with a therapeutically effective amount of a rapamycin analog. In certain non-limiting embodiments, where cells of the cancer do not contain a TSC1, TSC2 or mTOR biomarker, the subject is not treated with a rapamycin analog but treatment with another modality, for example an alternative chemotherapeutic agent, biologic anticancer agent, or radiation therapy, is administered.

A therapeutically effective amount is an amount that is able to achieve one or more of an anticancer effect, prolongation of survival, and/or prolongation of period until relapse.

In certain non-limiting embodiments, the present invention provides for a method of determining whether an anti-cancer effect is likely to be produced in a cancer by a rapamycin analog, comprising obtaining a sample of the cancer, and determining, in the sample, whether cells of the cancer contain a biomarker selected from a TSC1 biomarker, a TSC2 biomarker, a mTOR biomarker, and a combination thereof, where if the TSC1, TSC2, and/or mTOR biomarker is present, it is more likely that a rapamycin analog would have an anti-cancer effect on the cancer. Methods for determining the presence of a biomarker are set forth in section 5.1 above.

In certain non-limiting embodiments, the present invention provides for a method of treating a subject suffering from a cancer, comprising obtaining a plurality of samples from different locations of cancer in the subject, determining, in each sample, whether cells of the cancer contain a biomarker selected from a TSC1 biomarker, a TSC2 biomarker, a mTOR biomarker, and a combination thereof, and, where a TSC1 biomarker, a TCS2 biomarker, and/or a mTOR biomarker is present in a sample or a plurality of the samples or in all of the samples, treating the subject with a therapeutically effective amount of a rapamycin analog. In certain non-limiting embodiments, a TSC1 biomarker, a TSC2 biomarker, and/or a mTOR biomarker is present in all the samples. As exemplified below, the TSC1, TCS2, and/or mTOR biomarkers in multiple samples need not be the same. In certain non-limiting embodiments, the different locations of cancer giving rise to the samples are part of the same tumor mass. In certain non-limiting embodiments, the different locations of cancer giving rise to the samples are not all part of the same tumor mass (for example, one or more may arise from a tumor at a separate body location, such as a metastasis). In a certain, non-limiting embodiment, where one or more of the samples does not contain a TSC1, TSC2 or mTOR biomarker, the subject is not treated with a rapamycin analog but treatment with another modality, for example an alternative chemotherapeutic agent, biologic anticancer agent, or radiation therapy, is administered.

5.7 Kits

In non-limiting embodiments, the present invention provides for a kit for determining whether an anti-cancer effect is likely to be produced in a cancer by a rapamycin analog, comprising a means for detecting a biomarker selected from a TSC1 biomarker, a TSC2 biomarker, a mTOR biomarker, and a combination thereof. TSC1 biomarkers, TSC2 biomarkers, and mTOR biomarkers are set forth in the preceding sections.

Types of kits include, but are not limited to, packaged probe and primer sets (e.g. TaqMan probe/primer sets), arrays/microarrays, biomarker-specific antibodies and beads, which further contain one or more probes, primers, or other detection reagents for detecting one or more biomarkers of the present invention.

In a specific, non-limiting embodiment, a kit may comprise a pair of oligonucleotide primers, suitable for polymerase chain reaction (PCR) or nucleic acid sequencing, for detecting the biomarker(s) to be identified. A pair of primers may comprise nucleotide sequences complementary to a biomarker set forth above, and be of sufficient length to selectively hybridize with said biomarker. Alternatively, the complementary nucleotides may selectively hybridize to a specific region in close enough proximity 5' and/or 3' to the biomarker position to perform PCR and/or sequencing. Multiple biomarker-specific primers may be included in the kit to simultaneously assay large number of biomarkers. The kit may also comprise one or more polymerases, reverse transcriptase, and nucleotide bases, wherein the nucleotide bases can be further detectably labeled.

In non-limiting embodiments, a primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In a further non-limiting embodiment, the oligonucleotide primers may be immobilized on a solid surface or support, for example, on a nucleic acid microarray, wherein the position of each oligonucleotide primer bound to the solid surface or support is known and identifiable.

In a specific, non-limiting embodiment, a kit may comprise at least one nucleic acid probe, suitable for in situ hybridization or fluorescent in situ hybridization, for detecting the biomarker(s) to be identified. Such kits will generally comprise one or more oligonucleotide probes that have specificity for various biomarkers. Means for testing multiple biomarkers may optionally be comprised in a single kit.

In other non-limiting embodiments, a kit may comprise at least one antibody for immunodetection of the biomarker(s) to be identified. Antibodies, both polyclonal and monoclonal, specific for a biomarker, may be prepared using conventional immunization techniques, as will be generally known to those of skill in the art. The immunodetection reagents of the kit may include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels (3H, 35S, 32P, 14C, 131I) or enzymes (alkaline phosphatase, horseradish peroxidase).

In a further non-limiting embodiment, the biomarker-specific antibody may be provided bound to a solid support, such as a column matrix, an array, or well of a microtiter plate. Alternatively, the support may be provided as a separate element of the kit.

In one specific non-limiting embodiment, a kit may comprise a pair of primers, a probe, microarray, or antibody suitable for detecting the TSC1 Q781* nonsense mutation biomarker.

In one specific non-limiting embodiment, a kit may comprise a pair of primers, a probe, microarray, or antibody suitable for detecting the TSC1 P311fs*4 frameshift mutation biomarker.

In one specific non-limiting embodiment, a kit may comprise a pair of primers, a probe, microarray, or antibody suitable for detecting the TSC1 I580fs*7 frameshift biomarker.

In one specific non-limiting embodiment, a kit may comprise a pair of primers, a probe, microarray, or antibody suitable for detecting the TSC1 Q527* nonsense biomarker.

In one specific non-limiting embodiment, a kit may comprise a pair of primers, a probe, microarray, or antibody suitable for detecting the TSC1 S334* nonsense biomarker.

In one specific non-limiting embodiment, a kit may comprise a pair of primers, a probe, microarray, or antibody suitable for detecting the TSC2 Q794* nonsense mutation biomarker.

In one specific non-limiting embodiment, a kit may comprise a pair of primers, a probe, microarray, or antibody suitable for detecting the TSC2 R611W missense mutation biomarker.

In one specific non-limiting embodiment, a kit may comprise a pair of primers, a probe, microarray, or antibody suitable for detecting the TSC2 S1498N missense mutation biomarker.

In one specific non-limiting embodiment, a kit may comprise a pair of primers, a probe, microarray, or antibody suitable for detecting the mTOR Q2223K frameshift mutation biomarker.

In one specific non-limiting embodiment, a kit may comprise a pair of primers, a probe, microarray, or antibody suitable for detecting the mTOR R2505P mutation biomarker.

In one specific non-limiting embodiment, a kit may comprise a pair of primers, a probe, microarray, or antibody suitable for detecting the mTOR L243 IP mutation biomarker.

In one specific non-limiting embodiment, a kit may comprise a pair of primers, a probe, microarray, or antibody suitable for detecting the mTOR S2215F mutation biomarker.

In one specific non-limiting embodiment, a kit may comprise a pair of primers, a probe, microarray, or antibody suitable for detecting the mTOR V2406A mutation biomarker.

In one specific non-limiting embodiment, a kit may comprise a pair of primers, a probe, microarray, or antibody suitable for detecting the mTOR M2327L mutation biomarker.

In one specific non-limiting embodiment, a kit may comprise a pair of primers, a probe, microarray, or antibody suitable for detecting the mTOR L2230V mutation biomarker.

In one specific non-limiting embodiment, a kit may comprise a pair of primers, a probe, microarray, or antibody suitable for detecting the mTOR I2228T mutation biomarker.

In one specific non-limiting embodiment, a kit may comprise a pair of primers, a probe, microarray, or antibody suitable for detecting the mTOR L2220F mutation biomarker.

In one specific non-limiting embodiment, a kit may comprise a pair of primers, a probe, microarray, or antibody suitable for detecting the mTOR V2006L mutation biomarker.

In one specific non-limiting embodiment, a kit may comprise a pair of primers, a probe, microarray, or antibody suitable for detecting the mTOR T1977K mutation biomarker.

In one specific non-limiting embodiment, a kit may comprise a pair of primers, a probe, microarray, or antibody suitable for detecting the mTOR I1973F mutation biomarker.

In one specific non-limiting embodiment, a kit may comprise a pair of primers, a probe, microarray, or antibody suitable for detecting the mTOR F1888V, I, and/or L mutation biomarker.

In one specific non-limiting embodiment, a kit may comprise a pair of primers, a probe, microarray, or antibody suitable for detecting the mTOR F1888L and L2230V mutation biomarkers.

In one specific non-limiting embodiment, a kit may comprise a pair of primers, a probe, microarray, or antibody suitable for detecting the mTOR C1483F and/or C1483Y mutation biomarker.

In one specific non-limiting embodiment, a kit may comprise a pair of primers, a probe, microarray, or antibody suitable for detecting the mTOR L1460P mutation biomarker.

In one specific non-limiting embodiment, a kit may comprise a pair of primers, a probe, microarray, or antibody suitable for detecting the mTOR A1459P mutation biomarker.

In one specific non-limiting embodiment, a kit may comprise a pair of primers, a probe, microarray, or antibody suitable for detecting the mTOR L1433S mutation biomarker.

In one specific non-limiting embodiment, a kit may comprise a pair of primers, a probe, microarray, or antibody suitable for detecting the mTOR A1105P mutation biomarker.

In one specific non-limiting embodiment, a kit may comprise a pair of primers, a probe, microarray, or antibody suitable for detecting the mTOR E919V mutation biomarker.

In one specific non-limiting embodiment, a kit may comprise a pair of primers, a probe, microarray, or antibody suitable for detecting the mTOR K860N mutation biomarker.

In one specific non-limiting embodiment, a kit may comprise a pair of primers, a probe, microarray, or antibody suitable for detecting one or more of the mTOR mutations shown in FIG. 16.

In certain non-limiting embodiments, where the measurement means in the kit employs an array, the set of biomarkers set forth above may constitute at least 10 percent or at least 20 percent or at least 30 percent or at least 40 percent or at least 50 percent or at least 60 percent or at least 70 percent or at least 80 percent of the species of markers represented on the microarray.

In certain non-limiting embodiments, a biomarker detection kit may comprise one or more detection reagents and other components (e.g. a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction to detect a bio marker.

A kit may further contain means for comparing the biomarker with a standard, and can include instructions for using the kit to detect the biomarker of interest. Specifically, the instructions describes that the presence of a biomarker, set forth herein, is indicative of an increased possibility of an anti-cancer effect in a cancer by a rapamycin analog.

6. EXAMPLE: NEXT GENERATION SEQUENCING REVEALS GENOMIC DETERMINANTS OF LONG-TERM RESPONSE TO MTOR INHIBITORS IN PATIENTS WITH ADVANCED RENAL CELL CARCINOMA

As shown in FIG. 1, among patients treated with rapamycin analogs (rapalogs) only a relatively small subset of patients receive sufficient therapeutic benefit to support long-term use. This group of "long-term responder" patients was selected for further study in hopes of identifying characteristics which could be used to prospectively assess the likelihood of beneficial therapeutic response. FIGS. 2A and B show, respectively, characteristics of long-term responders and patients who did not substantially benefit from treatment ("poor responders"). DNA from both long-term responders and poor responders was then subjected to Integrated Mutation Profiling of Actionable Cancer Targets ("IMPACT") analysis, which employs bait for 230 cancer genes panel (FIG. 3A, and see 36). Genes of interest to mTOR pathway are enlarged and in bold in FIG. 3B.

FIG. 4 presents a summary of results for responders. Three tumor sites (FIG. 5B) were analyzed for patient 1, who was diagnosed with clear cell RCC and had a long-term response to temsirolimus. As shown in FIGS. 5A and C, patient 1 had a single copy of Chromosome 9 and different mutations of TSC1 at different tumor sites (P311fs and Q527). Three tumor sites and one metastasis (FIG. 6B) were analyzed for patient 2, who was diagnosed with unclassified RCC and had a long-term response to temsirolimus. As shown in FIGS. 6A and C, patient 2 had a I580fs mutation in TSC1.

Figure 8A:
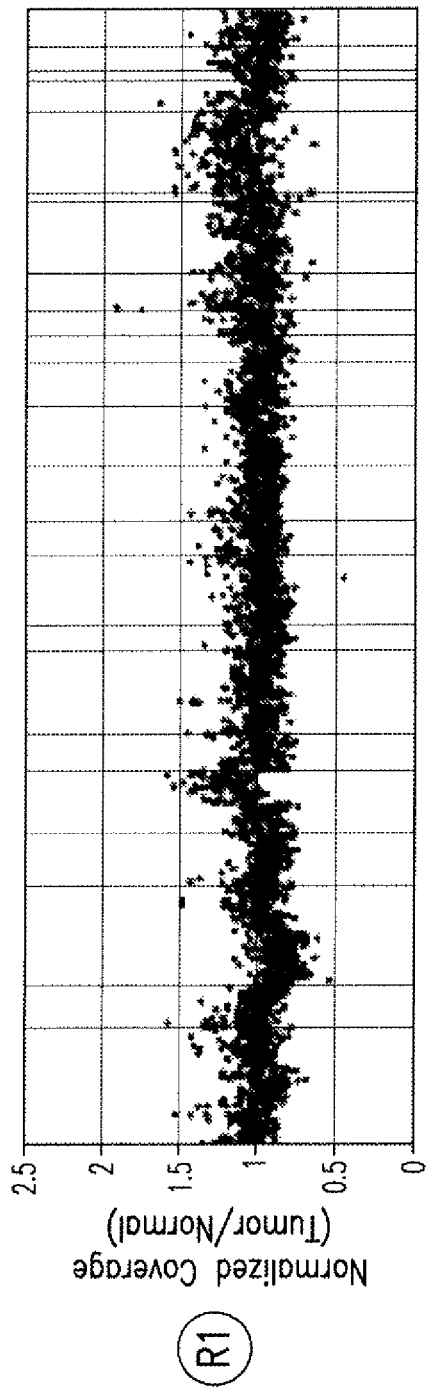
Figure 8B:
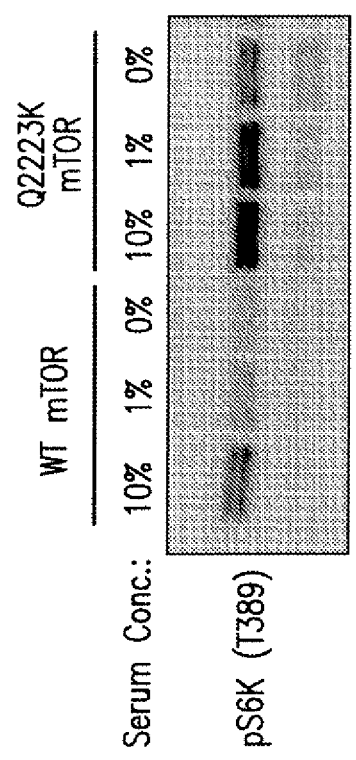
Figures 8C, 8D:
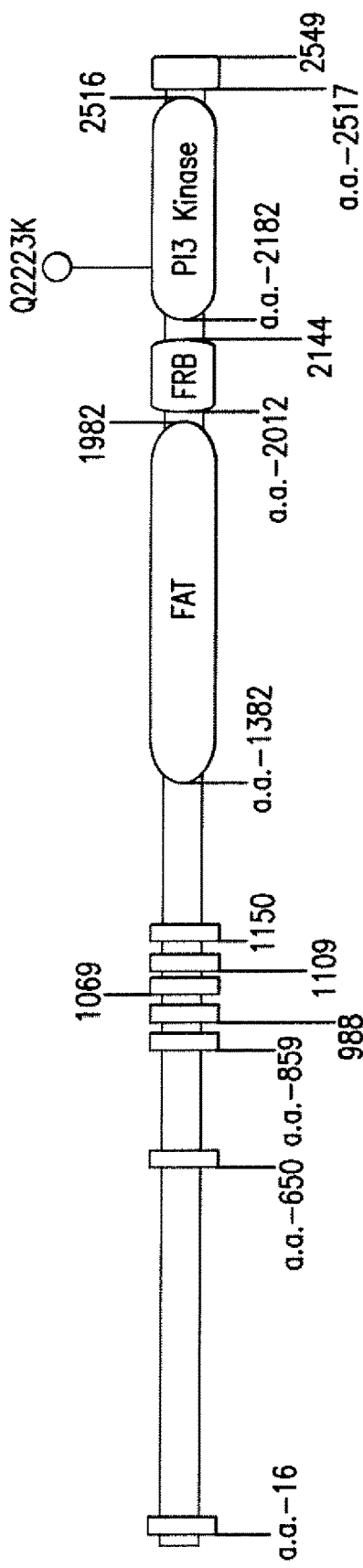

Patient 3, diagnosed with clear cell RCC and having a long-term response to everolimus, was found to have a Q781 mutation in TSC1 at two tumor sites of four assayed. Interestingly, the other two sites, while lacking the TSC1 mutation, had a Q2223K mutation in mTOR (FIG. 7A-B. Further study showed that the Q2223K mutation in mTOR resulted in gain-of-function (FIG. 8B). This mutation maps in the PI3K domain of mTOR (FIG. 8D).

Figure 9A:
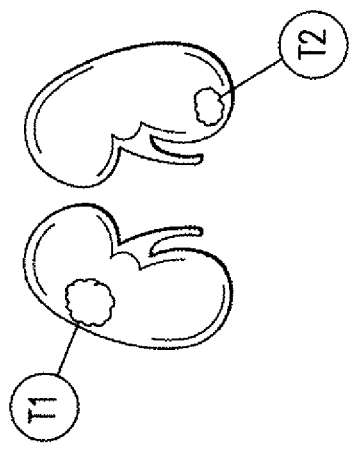
Figure 9B:
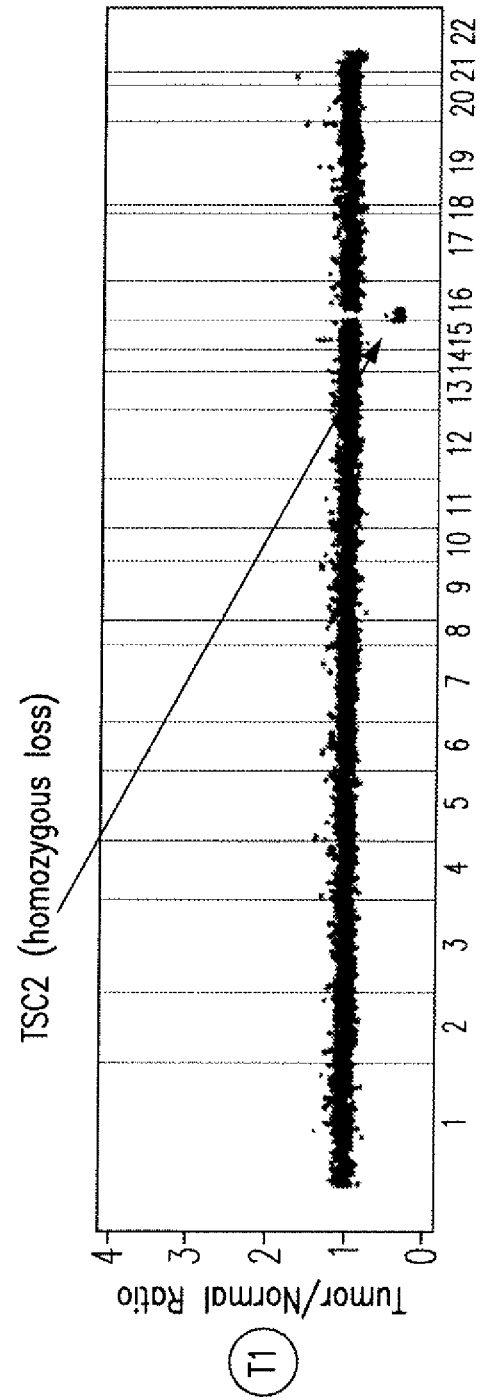
Figures 9C, 9D:
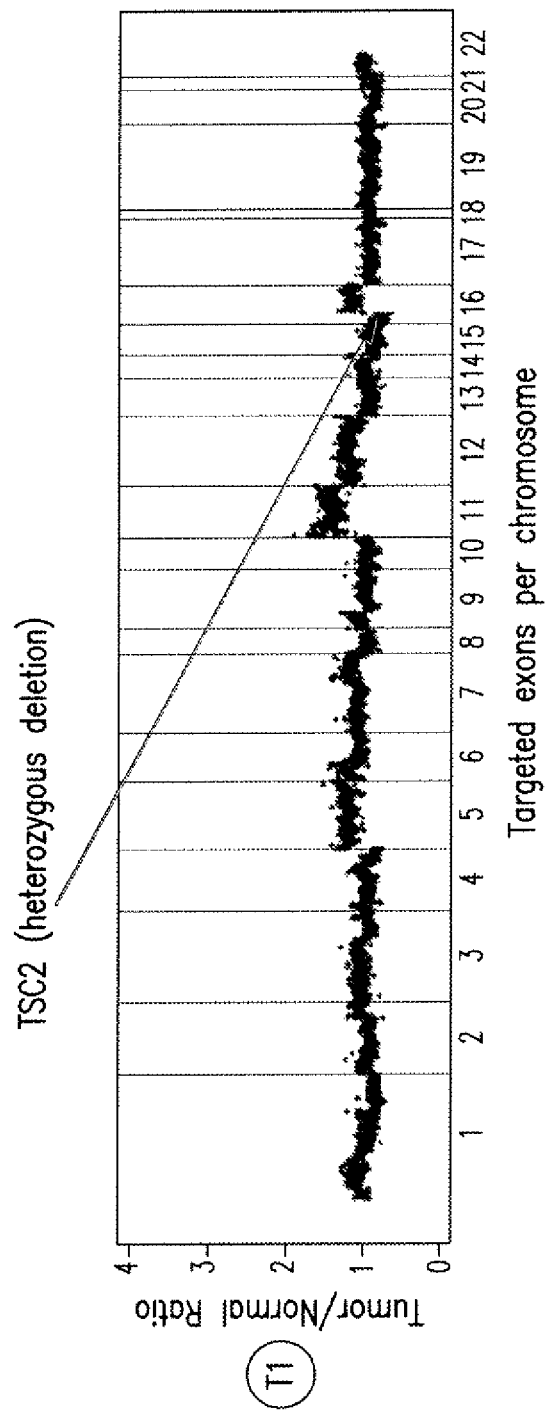

As shown in FIG. 9A-D, two tumor sites (FIG. 9A) were studied in patient 4, who was diagnosed with unclassified RCC and had a long-term response to everolimus. While no mutations were found, site 1 manifested homozygous loss of TSC2. At site 2, a heterozygous deletion, mutation Q794*, was observed (FIG. 9D).

FIG. 10 shows a summary of the mutations found and their functional consequences in the various long-term responder patients. As shown in FIG. 11, there were some mTOR relevant mutations identified in several poor responder patients but the mutations were missense mutations without apparent functional effect.

The foregoing data provides plausible oncogenomic causes for the exceptional treatment responses observed in some, but not all patients. It suggests that identification of mutations alone may not be sufficient without consideration of their biologic effects. It also illustrates that despite of intratumoral heterogeneity, targeted therapy can be successful due to clonal convergence within the pathway.

The foregoing study was advanced further and the results are presented below in Section 7.

7. EXAMPLE: PATHWAY CONVERGENT EVOLUTION IS A MAJOR DETERMINANT OF TREATMENT RESPONSE TO MTOR INHIBITORS IN KIDNEY CANCER 7.1 Materials and Methods Patients.

Six RCC cases were retrospectively identified from an institutional database of RCC patients treated with rapalogs at Memorial Sloan-Kettering Cancer Center (MSKCC). All had received either temsirolimus or everolimus as single-agent therapy. Six were selected based on extended therapeutic benefit, evident by treatment duration of ≥20 months. We felt this cut-off to be representative of long-term benefit, as the registration trials reported <10% or 0% of patients to be alive and progression-free at 20 months, respectively. As part of our analysis all scans obtained between commencement and discontinuation of rapalogs were retrospectively reviewed by a research radiologist. This protocol was approved by our institutional review board, and all patients had previously provided written consents on an institutional tissue procurement protocol. The access and utilization of the kidney cancer TCGA database for publication were approved by the TCGA Program Office.

Samples.

All 6 patients underwent nephrectomy prior to the initiation of rapalog therapy and have frozen specimens. Adjacent normal kidney tissue (n=5) or peripheral blood (n=1) were used for reference. To interrogate intratumor heterogeneity, DNA was extracted from FFPE materials of additional regions within the primary tumors (regions marked as R). Regions were chosen by a dedicated genitourinary pathologist based on interregional differences in histopathologic appearance. Furthermore, fresh frozen specimens of metastasis (marked as M1; patient #2) and a contralateral primary kidney tumor (2 separate tumors marked as T1 and T2, patient #4) were obtained to determine inter-tumor heterogeneity. Previously archived operative specimens were reviewed by an expert genitourinary pathologist to confirm the diagnosis and to identify separate areas of ≥70% tumor content and healthy kidney tissues. Macrodissection was performed for each area of interest, and DNA was extracted using the DNeasy tissue kit (Qiagen). DNA was quantified using the Thermo Scientific NanoDrop™ 1000 Spectrophotometer and samples with an A260/A280 ratio of 1.8-2.0 and concentration of 135 ng/µL or greater were considered acceptable for further analysis.

Next-Generation Sequencing.

DNA from tumors and matched normal was subjected to an analysis by two next-generation sequencing platforms. The IMPACT assay (Integrated Mutation Profiling of Actionable Cancer Targets) is a customized targeted-exome capture assay of 230 cancer-associated genes with ultra-deep sequencing coverage (>500×) using Illumina HiSeq 2000. Target-specific probes for hybrid selection were designed as previously described to capture all protein-coding exons of a list of oncogenes, tumor suppressor genes, and components of pathways deemed actionable by targeted therapies. The whole-exome capture assay with standard sequencing coverage (~85×) using the Agilent SureSelect XT HumanAllExon 50 Mb was performed. Single-nucleotide variants, small insertions and deletions, and copy number alterations (CNA) were interrogated.

The IMPACT Assay.

Ultra-deep targeted sequencing of key cancer-associated genes was performed using the IMPACT assay (Integrated Mutation Profiling of Actionable Cancer Targets). We designed target-specific probes to capture all protein-coding exons of 230 genes of interest for hybrid selection (Agilent SureSelect or Nimblegen SeqCap) as previously described (21). This list included commonly implicated oncogenes, tumor suppressor genes, and components of pathways deemed actionable by current targeted therapies (Table 2). Two protocols were followed during the course of the study. For 10 samples, barcoded sequence libraries (Illumina TruSeq) were prepared using 500 rig of input tumor or matched normal DNA according to the manufacturer's instructions. Libraries were pooled at equimolar concentrations (100 ng per library) for a single exon capture reaction (Agilent SureSelect) as previously described (31). For 12 samples, barcoded sequence libraries were prepared using 250 rig of input DNA using a hybrid protocol based on the NEBNext DNA Library Prep Kit (New England Biolabs). Manufacturer's instructions were followed with two substitutions: we used NEXTflex barcoded adapters (Bin Scientific) and HiFi DNA polymerase (Kapa Biosystems). Libraries were pooled at 100 ng per tumor library and 50 ng per normal library for a single exon capture reaction (Nimblegen SeqCap). To prevent off-target hybridization in all capture reactions, we spiked in a pool of blocker oligonucleotides complementary to the full sequences of all barcoded adaptors (to a final total concentration of 10 µM). Hybridized DNA was sequenced on an Illumina HiSeq 2000 to generate paired-end 75-bp reads. Data were demultiplexed using CASAVA, and reads were aligned to the reference human genome (hg19) using the Burrows-Wheeler Alignment tool (32). Local realignment and quality score recalibration were performed using the Genome Analysis Toolkit (GATK) according to GATK best practices (33). We achieved mean exon sequence coverage of 590× (625× for all tumor samples). Deep sequencing ensured sensitivity for detecting mutations in multiclonal and stroma-admixed samples and enabled accurate determination of mutation allele frequencies.

Sequence Data were Analyzed to Identify Three Classes of Somatic Alterations;

single-nucleotide variants, small insertions/deletions (indels), and copy number alterations. Single-nucleotide variants were called using muTect and retained if the variant allele frequency in the tumor was >5 times that in the matched normal. Indels were called using the SomaticIndelDetector tool in GATK. All candidate mutations and indels were reviewed manually using the Integrative Genomics Viewer34. The mean sequence coverage was calculated using the DepthOfCoverage tool in GATK and was used to compute copy number as described previously (22).

Whole-Exome Capture Sequencing.

Between 1.9 and 3 µg of high quality genomic DNA was captured by hybridization using the SureSelect XT HumanAllExon 50 Mb (Agilent). Samples were prepared according to the manufacturer instructions. PCR amplification of the libraries was carried out for 6 cycles in the pre-capture step and for 10 cycles post capture. Samples were bar-coded and run on a Hiseq 2000 in a 75 bp/75 bp Paired end run, using the TruSeq SBS Kit v3 (Illumina). Two samples were pooled in a lane, the average number of read pairs per sample was 69 million. All reads were aligned to the reference human genome (NCBI build 37.1 hg19). Exome reads were aligned with BWA 32 which does a gaped alignment for the detection of small indels, as described in below. Samples mapping to the reference genome which mapped uniquely (MAPQ>0) were retained and then converted to SAM format 31 for subsequent analyses and for visualization in the Integrative Genomics Viewer 34. Single nucleotide variants were determined in regions of sufficient coverage. We first removed duplicate reads (using Picard MarkDuplicates) from further analysis, defined here as any read chromosome, start position, strand, and color-space sequence matched another aligned read. Indel realignment, base quality recalibration, variant detection, and variant annotation were performed with the GATK framework (33, 35). Specifically, after base quality recalibration for color-space reads, variant detection in exome data was performed with the UnifiedGenotyper. For high-coverage exome experiments, variants were excluded if their variant quality was <30, genotype quality <5, or if they were associated with either homopolymer runs or excessive strand bias. Novel variants, those not previously identified in either dbSNP ver. 132, were required to be derived from basespace reads not duplicated from non-duplicate color-space reads, were not resident exclusively in higher-error base positions (positions 38-50) and had evidence of the variant allele in reads mapping to both strands. Candidate somatic mutations were those with a variant genotype in the tumor and reference genotype in the normal sample with minimum coverage of ≥10 and 6 reads respectively. Additionally, we required that the tumor variant frequency was ≥10%, and each variant was detected in 4 or more tumor reads. Our pipeline for small insertion and deletion (indel) detection was as follows. Gapped alignment of exome sequencing reads was performed with BWA. The alignment output was sorted and duplicate reads removed with the Picard pipeline and BAM files created and indexed with Samtools. Interval detection, local realignment, indel genotyping, and post-processing were performed with the GATK framework after base quality recalibration, as described above. Retained indels were those with sufficient quality and coverage and not associated with homopolymer runs of 5 bp or greater.

Sanger Sequencing.

Bidirectional Sanger sequencing for validation was performed for all mTOR pathway mutations using standard techniques with primers provided by the Geoffrey Beene Translational Oncology Core.

Plasmids.

Plasmids containing cDNA encoding myc-epitope-tagged S6K (pcDNA3-myc-S6K) and Flag-epitope-tagged Wild-type mTOR (pcDNA3-Flag mTOR) were obtained from Addgene (#26610 and #26603). To generate individual mTOR mutations, a corresponding nucleotide change was introduced via QuikChange site-directed mutagenesis (Stratagene), producing pcDNA3-Flag mTOR mutants. The primers used are shown in Table 7.

Cell Culture, Transfection, and Immunoblots.

HEK293T cells were cultured in DMEM with 10% fetal bovine serum, glutamine, non-essential amino acids, and antibiotics. To assay mTOR activity, pcDNA3-Flag mTOR was transfected alone or with Myc-S6K into HEK293T cells using Lipofectamine 2000, according to manufacturer instructions (Invitrogen). Twenty-four hours after transfection, cells were treated as indicated. Lysates were measured for protein concentration (Pierce BCA assay), and equal amounts of protein were resolved by PAGE and subjected to immunoblotting using the following antibodies against phospho-S6K1(T389), total S6K, phospho-S6 (S235/236), phospho-AKT (S473) (Cell Signaling #9205, #9202, #4858, 49270, β-Actin (Sigma, AC-15), Flag (Sigma, M2), and c-Myc (Santa Cruz, SC-40).

Computational Modeling of mTOR Kinase Domain.

The model was built by HMMHMM (hidden markov-model) comparison, using the HHpred server (http://toolkit.tuebingen.mpg.de) and the x-ray crystal structure of PIK3C3 (pdb: 31s8) as a template.

7.2 Results

Long-Term Rapalog Treatment Responders Identified in the MSKCC Kidney Cancer Database.

To probe into the genomic determinants underlying long-term rapalog therapeutic benefits, we searched the Memorial Sloan-Kettering Cancer Center (MSKCC) kidney cancer database and identified patients who (1) underwent nephrectomy prior to receiving systemic therapy for metastatic diseases (n=305) with archived fresh frozen tumors available for analysis, (2) were treated with single agent temsirolimus or everolimus, (3) displayed exceptional disease control (partial response or stable disease >20 months) on rapalogs, and (4) had received sunitinib previously, yet obtained greater clinical benefit with rapalogs. With such criteria, 6 patients were identified who were on average treated with single agent sunitinib for 9 months followed by rapalogs for 29+ months (Table 1).

An Integrated Next-Generation Sequencing Approach Identified Genetic Mutations Involving Three Core Components of the mTORC1 Signaling Pathway.

DNA from primary kidney tumors and matched normal kidney tissues or peripheral blood mononuclear cells was subjected to an integrated next-generation sequencing analysis employing two platforms: the IMPACT (Integrated Mutation Profiling of Actionable Cancer Targets; 19,21,22), and WEC (whole-exome capture) assays (FIGS. 17 and 18). With standard sequencing coverage (~100×), WEC enables us to survey mutational landscapes encompassing all coding exons. On the other hand, the IMPACT assay, a customized targeted-exome capture assay of 230 cancer-associated genes (Table 2) with an ultra-deep sequencing coverage (>500×) provides (5) opportunity to (1) capture genomic events potentially missed by WEC due to tumor impurity and/or heterogeneity, (2) effectively analyze DNA from formalin-fixed paraffin embedded (FFPE) samples, (3) compute copy number alterations (CNA), and (4) establish a platform which, by means of cost and efficiency, shows promise for future adaptation to a clinical test.

Single-nucleotide variants, small insertions and deletions, and copy number alterations (CNA) were first interrogated with IMPACT on all 6 patients (Table 3) and then with WEC on patients #5 and #6 (Table 4). Pertinent genomic findings are summarized (Table 5) and mutations relevant to our research question were confirmed by orthogonal bidirectional Sanger sequencing (FIG. 19). Interestingly, this approach identified genetic mutations involving three core components of the mTORC1 pathway, i.e., TSC1, TSC2, and mTOR, through distinct mechanisms, in 4 of 6 (67%) patients.

Complete Functional Loss of TSC1 or TSC2.

Figures 12A, 12B:
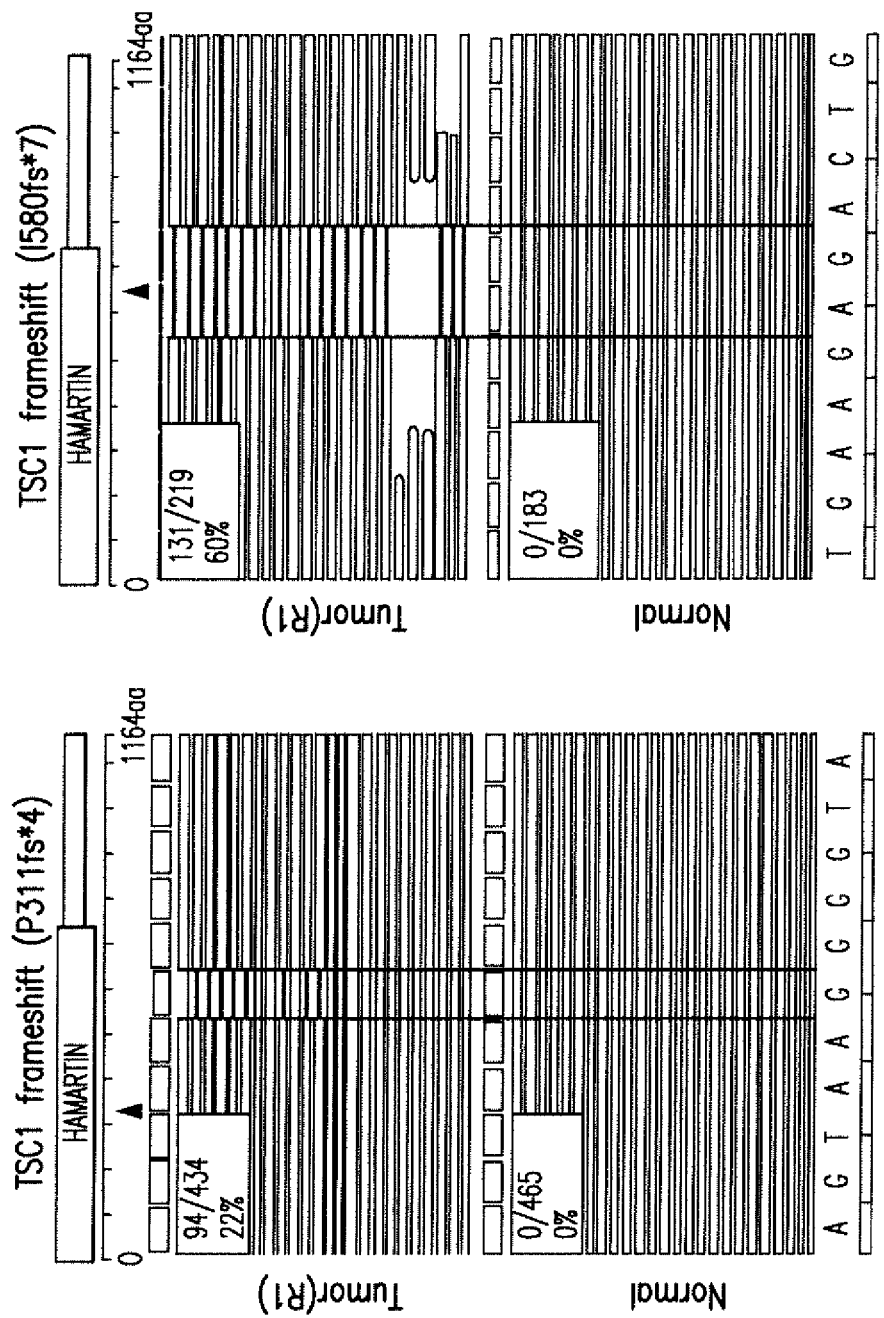

For patient #1, a 58 year-old female, the IMPACT analysis of the primary tumor at region 1 (R1) revealed a novel somatic TSC1 single nucleotide deletion (P311fs*4) (FIG. 12A, FIG. 19 and Table 5). Copy number analysis of the tumor revealed a single copy of chromosome 9 where the TSC1 gene resides (FIG. 12E). The frameshift mutation with LOH (loss of heterozygosity) would result in a complete functional impairment of TSC1 in the tumor. For patient #2, a 73 year-old female, the IMPACT analysis of R1 identified another novel somatic TSC1 frameshift mutation (I580fs*7) (FIG. 12B). Again a concurrent LOH was observed in this patient (FIG. 12E), indicating a complete functional abrogation of TSC1. For patient #4, a 16 year-old tuberous sclerosis complex 2 male who presented with metastatic disease and multiple (6) primaries of both kidneys, copy number analysis of germline (from peripheral blood) and tumor DNA revealed heterozygous loss of TSC2 in the germline and a bi-allelic TSC2 loss in primary kidney tumor 1 (T1) (FIG. 12C and FIG. 20). Complete functional abrogation of either TSC1 or TSC2 would hyperactivate the mTORC1 signaling.

An mTOR Kinase Domain Mutation Identified in the Tumor of Patient #3.

Figure 12D:
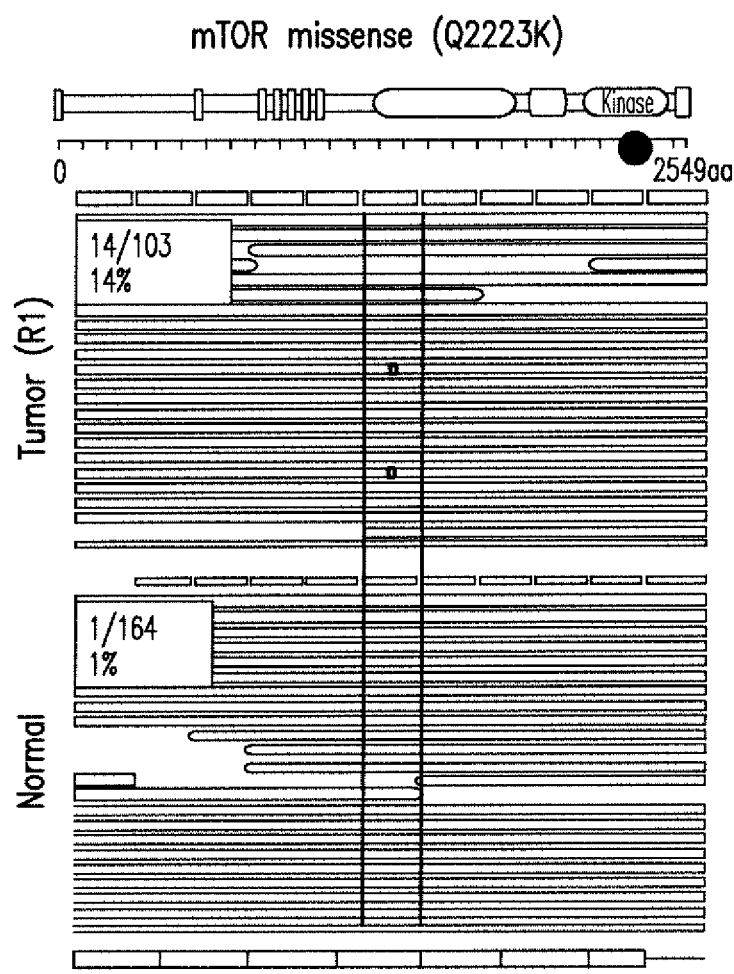
Figure 12C:
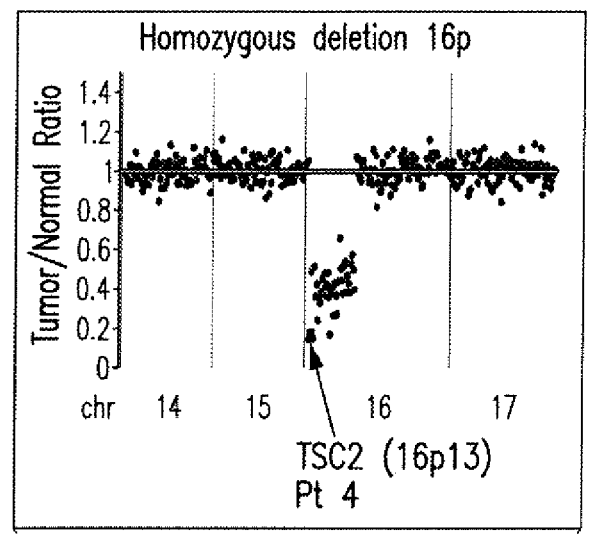
Figure 12E:
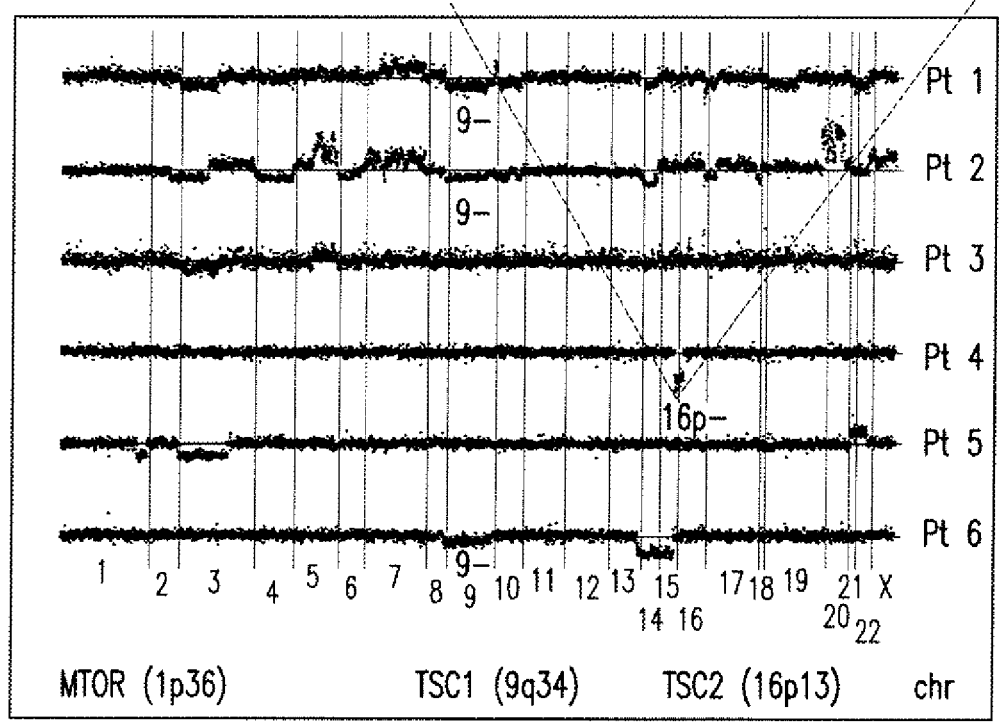
Figure 12F:
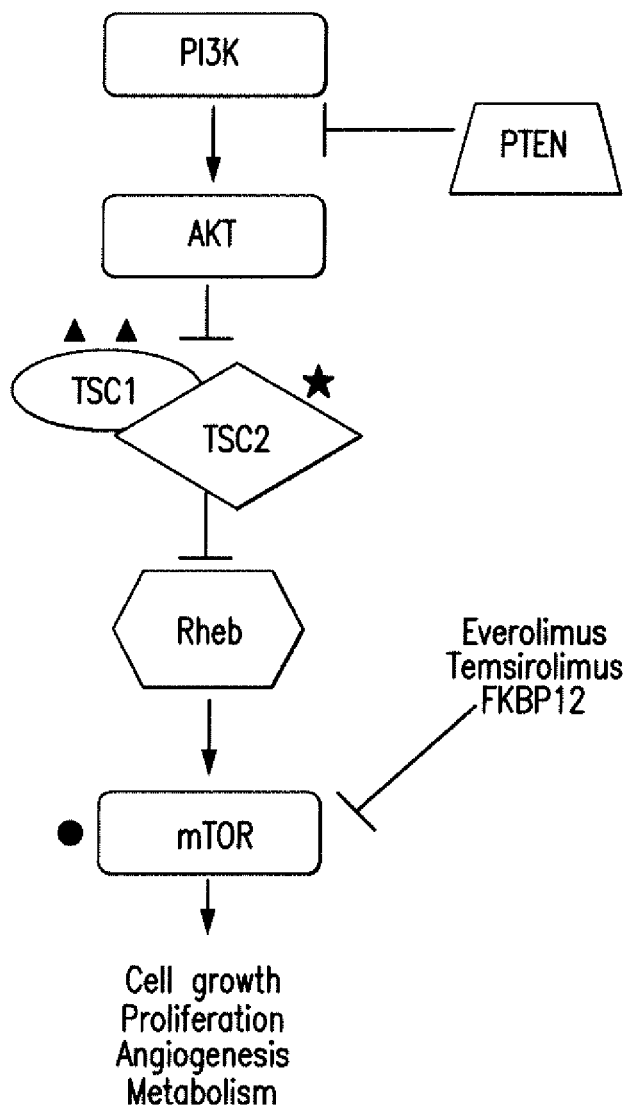

For patient #3, a 66 year-old male, the IMPACT analysis identified a novel somatic missense mutation of mTOR (Q2223K) at region 1 (R1) of the primary tumor (FIG. 12D). Amino acid glutamine at position 2,223 resides in the PI3K-related kinase domain of mTOR. The presence of a Q2223K mutation in a long-term rapalog responder raises a possibility that missense mutations of mTOR in the kinase domain might induce hyperactivity and yet remain sensitive to rapalogs which bind FKBP12 and then target the regulatory FRB domain. For patients #5 and #6, 60 and 50 year-old females, the IMPACT assay did not detect apparent causative oncogenomics events (Table 3). Furthermore, despite capturing a greater number of mutations, WEC (Table 4) also offered no apparent genetic clues concerning the therapeutic benefit of patients #5 and #6 to temsirolimus. Overall, IMPACT assays alone may be sufficient to evaluate the genetic signature of response to rapalogs.

The mTOR (Q2223K) Mutant Aberrantly Activates mTORC1 Yet Remains Sensitive to Rapamycin.

Figure 13A:
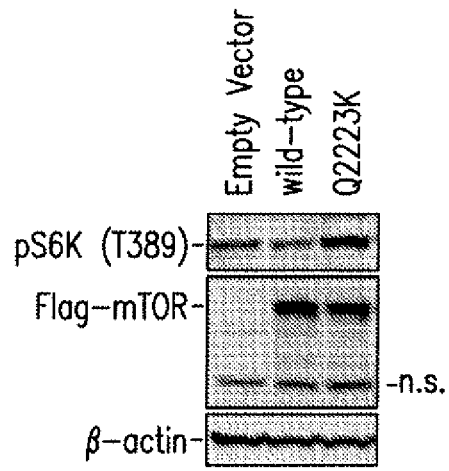
Figure 13B:
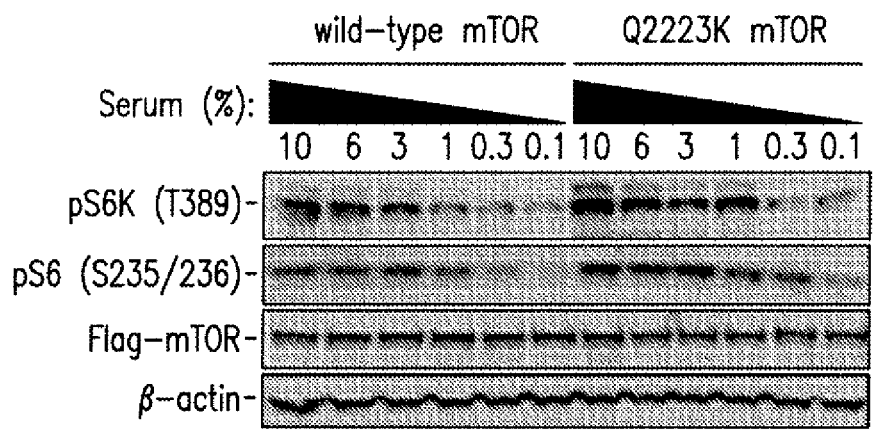
Figure 13C:
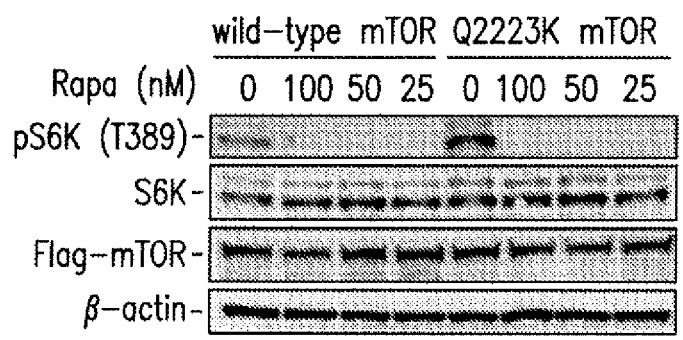
Figure 13E:
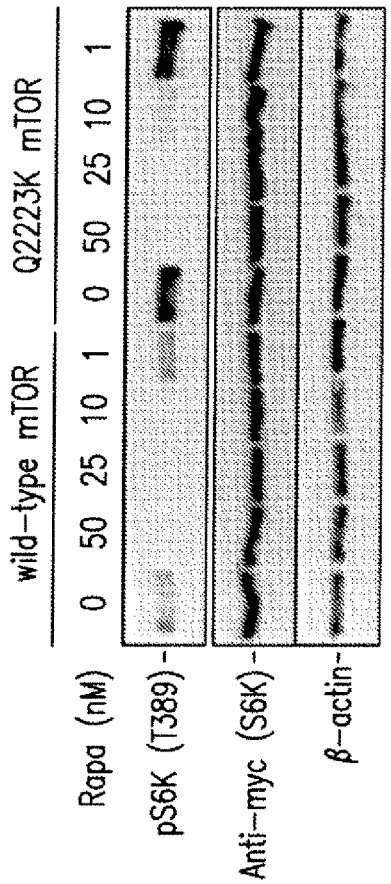
Figure 13F:
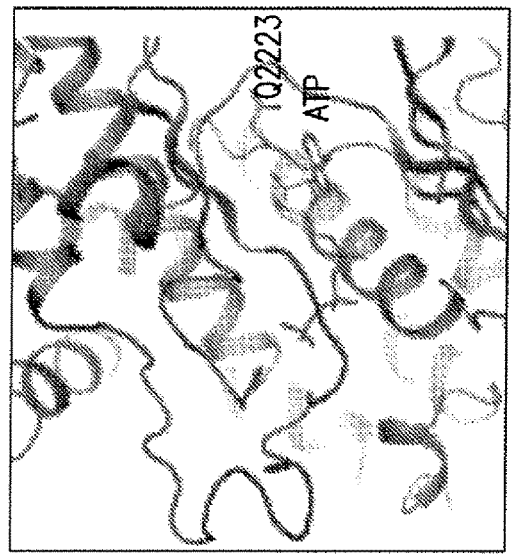
Figure 13D:
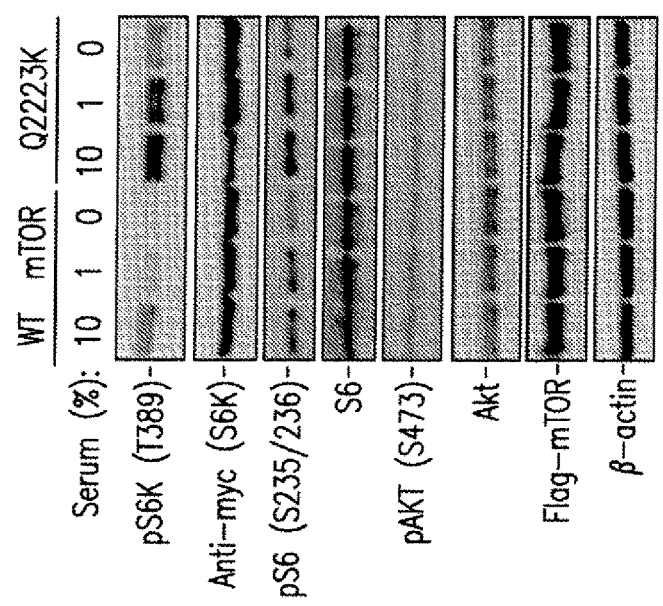

The discovery of an mTOR (Q2223K) mutant in the kidney tumor of patient #3 suggests that this mTOR kinase mutant may aberrantly activate mTORC1 yet remain sensitive to (7) rapalogs. To examine whether mTOR (Q2223K) affects the mTORC1 signaling, we examined its effect on the threonine 389 phosphorylation of S6K (p70S6 kinase, one of the key substrates of mTORC1). Cells expressing mTOR (Q2223K) displayed stronger S6K phosphorylation than those expressing wild-type mTOR (FIG. 13A). The observed hyperactivation by mTOR (Q2223K) mutant persisted over lower serum concentrations (FIG. 13B). Importantly, the mTOR (Q2223K) mutant was sensitive to rapamycin as wildtype mTOR (FIG. 13C). This contrasts with the hypersensitivity of EGFR activating mutants to small molecule ERFR inhibitors such as gefitinib and erlotinib (23), likely reflecting the intrinsic differences between EGFR tyrosine and PI3K/PI3K-like kinases. When exogenous S6K was co-transfected, a process known to augment mTORC1 signaling, we further demonstrated the hyperactivity of the mTOR (Q2223K) mutant at low serum and affirmed its sensitivity to rapamycin (FIG. 13D,E). Of note, the serine 473 phosphorylation of AKT, a key post-translational modification mediated by mTORC2, was not enhanced by mTOR (Q2223K), indicating that such mutant has no strong effect on mTORC2 (FIG. 13D). The lysine substitution of glutamine 2223 of the mTOR kinase domain has created an mTOR that only activates mTORC1 but not mTORC2. Modeling of the mTOR (Q2223K) mutation based on the solved PI3K kinase domain structure suggests that the 2,223 glutamine residue locates right next to the ATP binding site of the catalytic domain (FIG. 13F).

Clustered, Evolutionarily Preserved Activating Mutations of mTOR in Kidney Cancer.

Our discovery of a hyperactive mTOR (Q2223K) mutant in a long-term rapalog-treated patient suggests that activating mTOR mutations in tumors could be implicative of treatment response to rapalogs. Analysis of the clear cell kidney cancer TCGA database (8) through the cBio Genomics Portal revealed mTOR mutations in 5.4% of examined cases (23/424) (Table 6). Importantly, all of these are missense mutations, and the majority clusters on either the FAT or kinase domain (FIG. 14A). Accordingly, we performed functional assessment on most of mTOR mutants identified in TCGA, COSMIC, and MSKCC kidney cancer databases (FIG. 14A-C). Remarkably, nearly all mutations clustered on FAT or kinase domains exhibited hyperactive mTORC1 activity (FIG. 14B and FIG. 16) and were sensitive to rapamycin (FIG. 14C). The scattered uncommon mutations near the HEAT domains appear to be neutral and likely represent passenger mutations due to the inherent large size of mTOR. Our discovery and subsequent functional validation of clustered hyperactive mTOR mutations in the kidney cancer TCGA database suggests that these are recurrent events in ccRCC. It is highly noteworthy that clusters of activating mTOR mutations around the FAT and kinase domains identified in kidney cancer recapitulate a pattern reported in fission yeast (FIG. 14A; 24). Using random mutagenesis screens, they identified and functionally validated a large number of similarly clustered activating mutations in TOR2, the yeast equivalent of mTOR (FIG. 14A). Together, we unveiled a preserved structural/functional evolution/selection of mTOR/TOR in human cancer pathology and unicellular biology.

Thus far, our cancer genomics based on single biopsies of therapeutic outliers was able to successfully provide logical genetic explanations for observed exceptional response to rapalogs in 4 of 6 (67%) patients. All of these mutations would have led to hyperactive mTORC1 signaling. Our findings are in line with the exceptional therapeutic response of imatinib, an Abelson kinase inhibitor, in treating CML bearing the BCR-ABL fusion gene (25), and erlotinib, an EGFR inhibitor, in treating EGFR mutant lung cancer (23). However, recent reports on the complexity of intra-tumor heterogeneity and the branched clonal evolution of RCC raise concerns about the feasibility of single-biopsy genomics in formulating personalized cancer medicine (26,27). To resolve this conundrum, multiregional IMPACT assays were performed on all available additional specimens (spatially separated regions within the primary kidney tumors and metastatic sites whenever are available; and mainly are formalin-fixed paraffin embedded samples) of patients #1 to #4.

Additional 9 regions were chosen based on interregional histopathologic differences. Genomic findings are summarized (FIG. 15A-D and Table 5).

Intra-Tumor Heterogeneity with TSC1 Intra-Genic mTOR Pathway Convergent Evolution.

Figure 15A:
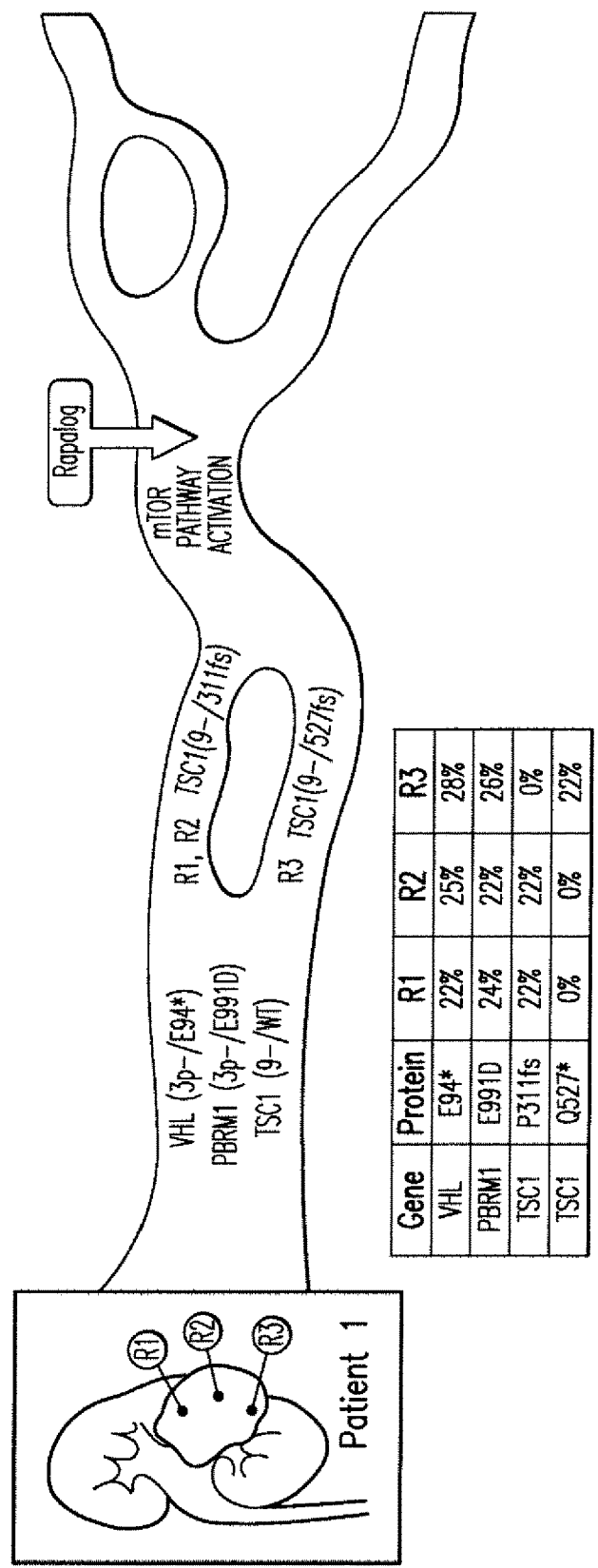
Figure 15B:
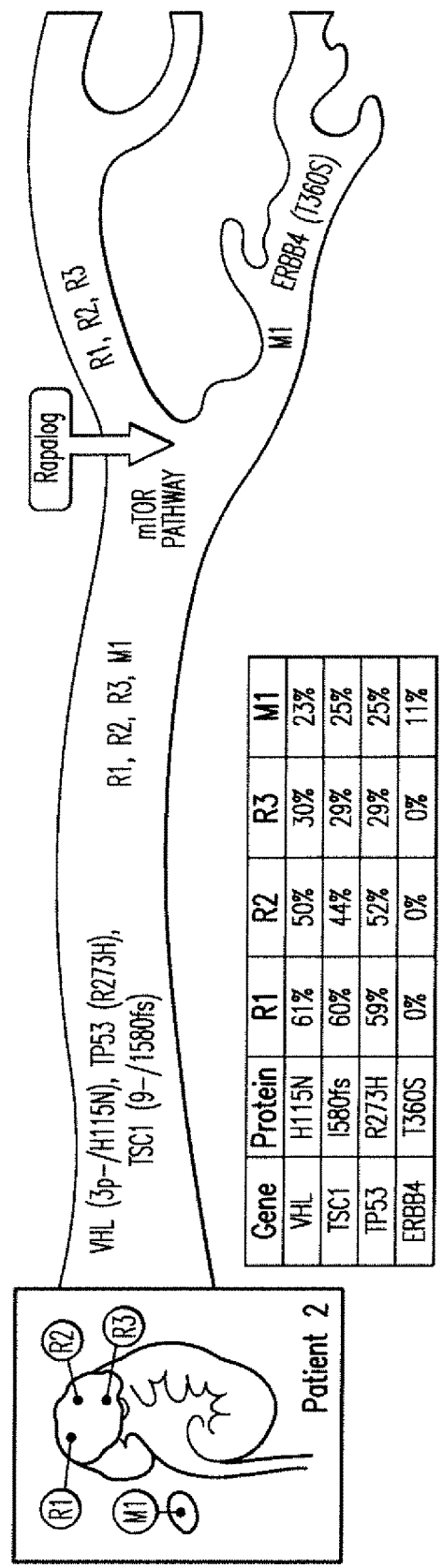

For patient #1, two additional regions (R2, R3) within the primary tumor were examined. Identical to R1 described above, R2 carried a TSC1 (P311fs*4) deletion and a heterozygous loss of chromosome 9 (9-) (FIG. 15A). Interestingly, analysis of R3 revealed a different nonsense TSC1 (Q527*) mutation with a concurrent heterozygous loss of chromosome 9 (FIG. 15A and FIG. 21). Hence, two distinct TSC1 loss-of-function mutations were discovered in spatially separated areas within the same primary tumor. This would simultaneously trigger aberrant mTORC1 activation at different regions of the same tumor, exemplifying an intra-genic (TSC1) clonal convergent evolution of kidney cancer cells in the same patient. For patient #2, the analysis included 2 additional regions within the primary tumor (R2, R3) and one distant metastasis (M1). R2, R3, and M1 all harbored the same TSC1 (I580fs*7) mutation and a concurrent LOH through one copy loss of chromosome 9, which are identical to what discovered in R1 (FIG. 15B). Matching results across all analyzed specimens support a notion that all examined sites originated from one dominant clone which has a complete functional loss of TSC1.

Inter-Tumor Heterogeneity with TSC2 Intra-Genic mTOR Pathway Convergent Evolution.

For the tuberous sclerosis patient #4, primary tumors of both kidneys (T1, T2) were analyzed. In addition to the germline heterozygous, chromosomal loss of TSC2 (16p+/−), T1 and T2 harbored distinct genomic events, yet converged on a complete loss of TSC2 function: a large deletion with loss of the 2nd allele of TSC2 in T1 (FIG. 12C), and a nonsense mutation of TSC2 (Q794*) in T2 (FIG. 15D and FIG. 21), exemplifying an inter-tumor (T1 vs. T2), intra-genic (TSC2) convergent evolution of kidney cancers in the same patient.

Intra-Tumor Heterogeneity with mTOR Gain-of-Function and TSC1 Loss-of-Function Inter-Genic mTOR Pathway Convergent Evolution.

Figure 15C:
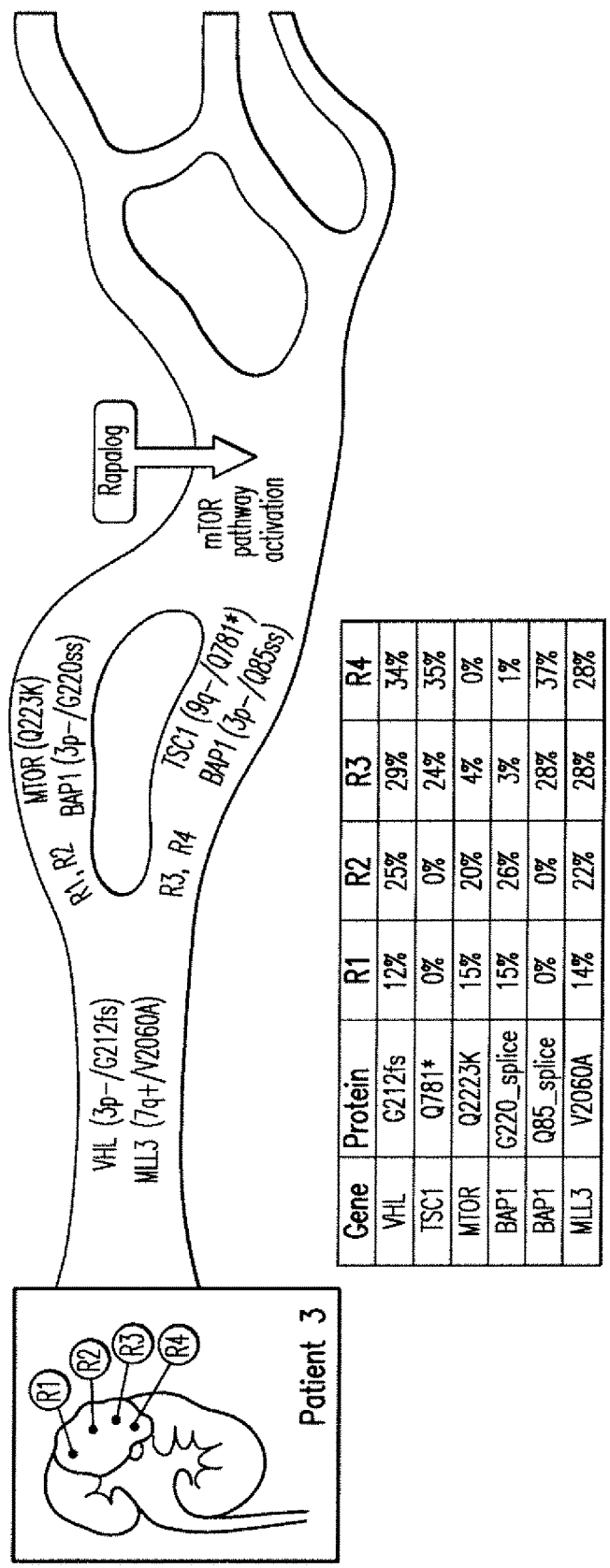
Figure 15D:
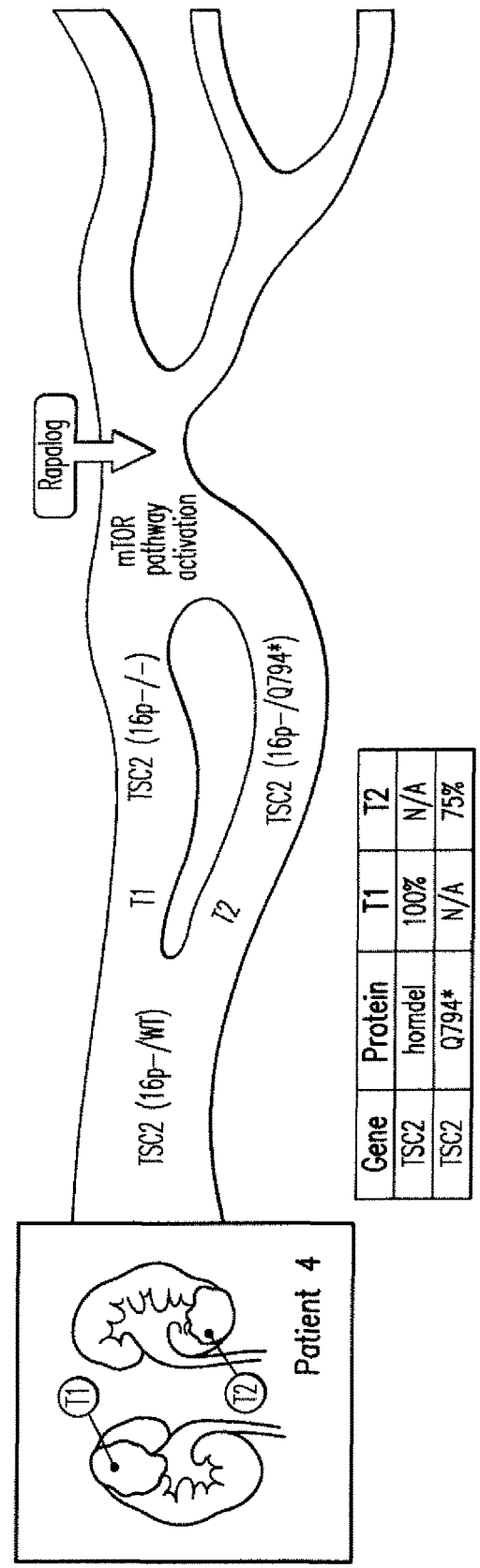

For patient #3 whose kidney tumor region 1 (R1) carries an mTOR kinase domain activating mutation, three additional sites (R2, R3, R4) within the nephrectomy specimen were analyzed. R2 carries the same mTOR (Q2223K) mutation as R1 (FIG. 15C). Strikingly, although R3 and R4 carried the same VHL and MLL3 mutations as R1 and R2, consistent with a shared ancestral clone, R3 and R4 tumors contained a loss-of-function TSC1 (Q781*) mutation and a concurrent LOH through chromosome 9-, resulting in a complete functional impairment of TSC1 ((FIG. 15C and FIGS. 21 and 22). Hence, three distinct mechanisms, including a missense gain-of-function mutation of growth promoting gene (mTOR), a nonsense loss-of-function mutation of tumor suppressor (TSC1), and another loss-of-function of TSC1 through LOH (9-), were employed by spatially separated cancer clones within the same primary tumor to concurrently activate mTORC1. The presence of different BAP1 splice site mutations between R1/R2 and R3/R4 not only exemplifies their convergent evolution on BAP1 but also supports observed clonal bifurcation (FIG. 1 SC). To our knowledge, this represents the first concurrent inter-genic (mTOR and TSC1) pathway convergent evolution (mTORC1 activation) discovered in human cancer.

7.3 Discussion

Our multiregional IMPACT study revealed complete loss-of-function of either TSC1 or TSC2 in all tumors tested for patients #1, #2, and #4, and the coexistence of complete functional loss of TSC1 and gain-of-function of mTOR (Q2223K) in spatially separated regions of the same primary tumor in patient #3. Additionally, we discovered that a significant number of clustered activating mutations of mTOR exist in kidney albeit to a lesser extent in other cancers (FIG. 23). Importantly, mTOR (Q2223K) also occurs in colon cancer (CRC TCGA) and thus represents a recurrent mutation. Altogether, our study not only suggests uncontrolled mTORC1 signaling as an important contributor to the pathogenesis of kidney cancer but also discovers logical predictive genomic biomarkers for exceptional rapalog response in kidney cancer. Of note, the mTORC1 pathway convergent evolution, through complete functional loss of TSC1 or TSC2, or clustered activating mutations of mTOR discovered in our study, was not present in 5 MSKCC kidney cancer patients whose metastatic cancers progressed within two months despite rapalog treatment (non-responders) (data not shown). Intriguingly, we noticed a heterozygous TSC1 loss in one of the non-responders, suggesting that haploid inactivation of TSC1 alone likely has limited predictive value in kidney cancer. This contrasts with a recent report on bladder cancer where haploid inactivation of TSC1 was reported to correlate with response to everolimus in a 14 patient cohort with a median treatment time of 2.6 (1.8-4.1) months, when a long-term responder (33+ months) carrying an additional NF2 mutation was excluded (19). Since mTOR activating mutations are also present in cancers for which rapalogs are not standard of care (FIG. 23), it might be prudent to conduct a clinical trial administering rapalogs on selected patients whose tumors carry these pathway convergent mutations.

The accumulation of diverged mutations during individual cancer evolution underscores the propensity of given tumors in achieving higher intra-tumor heterogeneity for the greater robustness of cancer cells (28). Our data are in agreement with recent demonstrations of the existence of a significant number of private mutations in separated regions of primary and metastatic kidney tumors, demonstrating the highly heterogeneous nature in genomics of individual kidney cancers (20). Branching evolution of cancers supports a central tenet that in order to achieve sustainable therapeutic benefit with targeted therapy one must identify and interfere with the earliest mutation events. Under such premises, ensuing genetic ramifications would mitigate the applicability of targeted therapeutic agents. Importantly, despite such an inherent predicament, our data based on kidney cancers suggest that specific tumor types might be prone to evolve around cancer type-specific central pathways (29,30) that contain regulatory circuits consisting of multiple genetic constituents. In our case, multiple distinct mechanisms, including various nonsense mutations, LOH through chromosomal loss, and activating mutations, can all be usurped by kidney cancer cells to activate mTORC1, for example the complete loss of TSC1 or TSC2, and the activating mutation of mTOR. Such pathway convergence in turns signals out converged vulnerability of cancers that can be effectively intervened with pathway inhibitors. On a cautionary note, one kidney cancer patient, reported in a recent article, harbored an activating mTOR (L2431P) mutation in the primary tumor but not
metastatic sites (20). This patient progressed after ~7 months of everolimus treatment, explaining the lack of exceptional therapeutic response. Hence, multiple biopsies of tumors at different sites could be advised to discover those converging "Achilles' Heels".

To visualize this concept for treatment planning, we designate "a braided cancer river" to model cancer of a given patient, which branches to illustrate tumor heterogeneity generated by genetic mutations and merges to depict functional convergence through pathway integration. Lastly, it is tempting to speculate that other cancers may also channel through several key tumor type-specific converging pathways that prevalently operate in given cancer types for their robustness, which at the same time provides unique therapeutic vantage points.

TABLE 1

Patient characteristics of long-term rapalog responders.

| | Sex | Age | Histologic subtype | MSKCC risk score | Number of prior regimens | Duration prior treatment with VEGF targeted therapy [months] (agent) | # of metastatic sites | Rapalog | Duration treatment with rapalog [months] |
|---|---|---|---|---|---|---|---|---|---|
| 1 | F | 58 | clear | Int | 1 | 14 (sunitinib) | ≥3 | temsirolimus | 27 |
| 2 | F | 73 | unclassified | Int | 1 | 3 (sunitinib) | 1 | temsirolimus | 34 |
| 3 | M | 16 | unclassified | Int | 3 | 19 (sunitinib) | 1 | everolimus | 36+ |
| 4 | M | 66 | clear | Int | 2 | 5 (sunitinib) | ≥3 | everolimus | 20 |
| 5 | F | 60 | clear | Fav | 3 | 11 (sunitinib) | ≥3 | temsirolimus | 28 |
| 6 | F | 50 | unclassified | Fav | 1 | 2 (sunitinib) | ≥3 | temsirolimus | 33+ |

MSKCC: Memorial Sloan-Kettering Cancer Center
Int: intermediate;
Fav: favorable;
N/A: not applicable;
VEGF: vascular endothelial growth factor;
TTP: time to progession by RECIST 1.1

TABLE 2

IMPACT gene list and positions.

| Gene Symbol | RefSeq ID | Chromosome |
|---|---|---|
| ABL1 | NM_005157 | 9q34.1 |
| ABL2 | NM_005158 | 1q25.2 |
| AKT1 | NM_005163 | 14q32.32-q32.33 |
| AKT2 | NM_001626 | 19q13.1-q13.2 |
| AKT3 | NM_005465 | 1q44 |
| ALK | NM_004304 | 2p23 |
| ALOX12B | NM_001139 | 17p13.1 |
| APC | NM_000038 | 5q21-q22 |
| AR | NM_000044 | Xq12 |
| ARAF | NM_001654 | Xp11.3-p11.23 |
| ARHGAP26 | NM_015071 | 5q31 |
| ARID1A | NM_006015 | 1p36.1-p35 |
| ASXL1 | NM_015338 | 20q11 |
| ATM | NM_000051 | 11q22-q23 |
| ATRX | NM_000489 | Xq21.1 |
| AURKA | NM_003600 | 20q13 |
| BAP1 | NM_004656 | 3p21.31-p21.2 |
| BCL2L1 | NM_001191 | 20q11.21 |

TABLE 2-continued

IMPACT gene list and positions.

| Gene Symbol | RefSeq ID | Chromosome |
|---|---|---|
| BCL6 | NM_001706 | 3q27 |
| BIRC2 | NM_001166 | 11q22 |
| BRAF | NM_004333 | 7q34 |
| BRCA1 | NM_007294 | 17q21-q24 |
| BRCA2 | NM_000059 | 13q12-q13 |
| CARD11 | NM_032415 | 7p22 |
| CBL | NM_005188 | 11q23.3-qter |
| CBLB | NM_170662 | 3q |
| CBLC | NM_012116 | 19q13.2 |
| CCND1 | NM_053056 | 11g13 |
| CCNE1 | NM_001238 | 19q12 |
| CD79B | NM_000626 | 17q23 |
| CDC42EP2 | NM_006779 | 11q13 |
| CDC73 | NM_024529 | 1q25 |
| CDH1 | NM_004360 | 16q22.1 |
| CDK4 | NM_000075 | 12q13 |
| CDK6 | NM_001259 | 7q21-q22 |
| CDK8 | NM_001260 | 13q12 |
| CDKN2A | NM_000077 | 9p21 |
| CDKN2B | NM_004936 | 9p21 |
| CDKN2C | NM_001262 | 1p32.3 |
| CEBPA | NM_004364 | 19q13.1 |
| CHEK1 | NM_001274 | 11q24.2 |
| CHEK2 | NM_007194 | 22q12.1 |
| CREBBP | NM_004380 | 16p13.3 |
| CRKL | NM_005207 | 22q11.21 |
| CRLF2 | NM_022148 | Xp22.3 and Yp11.3 |
| CSF1R | NM_005211 | 5q32 |
| CTNNB1 | NM_001904 | 3p21 |
| CYLD | NM_015247 | 16q12-q13 |
| DAXX | NM_001350 | 6p21.3 |
| DDR2 | NM_006182 | 1q12-q23 |
| DICER1 | NM_030621 | 14q2.2 |
| DIS3 | NM_014953 | 13q21.32 |
| DNMT1 | NM_001379 | 19p13.2 |
| DNMT3A | NM_022552 | 2p23 |
| DNMT3B | NM_006892 | 20q11.2 |
| EGFR | NM_005228 | 7p12 |
| EIF4EBP1 | NM_004095 | 8p12 |
| EP300 | NM_001429 | 22q13.2 |
| EPHA3 | NM_005233 | 3p11.2 |
| EPHA5 | NM_004439 | 4q13.1 |
| EPHA6 | NM_173655 | 3q12.1 |
| EPHA7 | NM_004440 | 6q16.3 |
| EPHA8 | NM_020526 | 1p36.13 |
| EPHB1 | NM_004441 | 3q21-q23 |
| EPHB4 | NM_004444 | 7q22 |
| EPHB6 | NM_004445 | 7q33-q35 |
| ERBB2 | NM_004448 | 17q11.2-q12 |
| ERBB3 | NM_001982 | 12q13 |
| ERBB4 | NM_005235 | 2q33.3-q34 |
| ERG | NM_004449 | 21q22.3 |
| ESR1 | NM_000125 | 6q24-q27 |
| ETV1 | NM_004956 | 7p22 |
| ETV6 | NM_001987 | 12p13 |
| EZH2 | NM_004456 | 7q35-q36 |
| FAM123B | NM_152424 | Xq11.1 |
| FAM46C | NM_017709 | 1p12 |
| FAS | NM_000043 | 10q24.1 |
| FBXW7 | NM_018315 | 4q31.23 |
| FGFR1 | NM_015850 | 8p12 |
| FGFR2 | NM_000141 | 10q25.3-q26 |
| FGFR3 | NM_000142 | 4p16.3 |
| FGFR4 | NM_002011 | 5q33-qter |
| FH | NM_000143 | 1q42.1 |
| FLCN | NM_144606 | 17p11.2 |
| FLT1 | NM_002019 | 13q12 |
| FLT3 | NM_004119 | 13q12 |
| FOXL2 | NM_023067 | 3q23 |
| GATA1 | NM_002049 | Xp11.23 |
| GATA2 | NM_032638 | 3q21 |
| GATA3 | NM_002051 | 10p15 |
| GNA11 | NM_002067 | 19p13.3 |
| GNAQ | NM_002072 | 9q21 |
| GNAS | NM_000516 | 20q13.2-q13.3 |
| GOLPH3 | NM_022130 | 5p13.2 |
| GRIN2A | NM_000833 | 16p13.2 |
| GSK3B | NM_002093 | 3q13.3 |
| HDAC2 | NM_001527 | 6q21 |
| HIF1A | NM_001530 | 14q23.2 |
| HMGA2 | NM_003483 | 12q15 |
| HNF1A | NM_000545 | 12q24.31 |
| HRAS | NM_005343 | 11p15.5 |
| HSP90AA1 | NM_005348 | 14q32.33 |
| IDH1 | NM_005896 | 2q32-qter |
| IDH2 | NM_002168 | 15q21-qter |
| IGF1R | NM_000875 | 15q26.3 |
| IGFBP7 | NM_001553 | 4q12 |
| IKBKE | NM_014002 | 1q31 |
| IKZF1 | NM_006060 | 7pter-7qter |
| IN6R | NW_000208 | 19p13.3-p13.2 |
| IRS1 | NM_005544 | 2q36 |
| IRS2 | NM_003749 | 13q34 |
| JAK1 | NM_002227 | 1p32.3-p31.3 |
| JAK2 | NM_004972 | 9p24 |
| JAK3 | NM_000215 | 19p13-p12 |
| JUN | NM_002228 | 1p32-p31 |
| KDM5C | NM_004187 | Xp11.22-p11.21 |
| KDM6A | NM_021140 | Xp11.2 |
| KDR | NM_002253 | 4q11-q12 |
| KEAP1 | NM_012289 | 19p13.2 |
| KIT | NM_000222 | 4q11-q12 |
| KLF6 | NM_001300 | 10p15 |
| KRAS | NM_004985 | 12p12.1 |
| LDHA | NM_005566 | 11p15.1 |
| LGR6 | NM_021636 | 1q32.1 |
| MAGI2 | NM_012301 | 7q21 |
| MAP2K1 | NM_002755 | 15q22.1-q22.33 |
| MAP2K2 | NM_030662 | 19p13.3 |
| MAP2K4 | NM_003010 | 17p11.2 |
| MAP3K8 | NM_005204 | 10p11.2 |
| MCL1 | NM_021960 | 1q21 |
| MDM2 | NM_002392 | 12q13-q14 |
| MDM4 | NM_002393 | 1q32 |
| MEN1 | NM_000244 | 11q13 |
| MET | NM_000245 | 7q31 |
| MITF | NM_000248 | 3p14.1-p12.3 |
| MLH1 | NM_000249 | 3p22.3 |
| MLL | NM_005933 | 11q23 |
| MLL2 | NM_003482 | 12q12-q13 |
| MLL3 | NM_170606 | 7q36 |
| MLST8 | NM_022372 | 16p13.3 |
| MPL | NM_005373 | 1p34 |
| MSH2 | NM_000251 | 2p21 |
| MSH6 | NM_000179 | 2p16 |
| mTOR | NM_004958 | 1p36 |
| MYB | NM_005375 | 6q22-q23 |
| MYC | NM_002467 | 8g24 |
| MYCL1 | NM_005376 | 1p34.3 |
| MYCN | NM_005378 | 2p24.3 |
| NCOA2 | NM_006540 | 8q13 |
| NF1 | NM_000267 | 17q11.2 |
| NF2 | NM_000268 | 22q12.2 |
| NFE2L2 | NM_006164 | 2q31 |
| NFKB1 | NM_003998 | 4g24 |
| NFKB2 | NM_002502 | 10q24 |
| NKX2-1 | NM_003317 | 14q13.3 |
| NOTCH1 | NM_017617 | 9q34.3 |
| NOTCH2 | NM_024408 | 1p13-p11 |
| NOTCH3 | NM_000435 | 19p13.2-p13.1 |
| NOTCH4 | NM_004557 | 6p21.3 |
| NPM1 | NM_002520 | 5q35.1 |
| NRAS | NM_002524 | 1p13.2 |
| NTRK1 | NM_002529 | 1q21-q22 |
| NTRK2 | NM_006180 | 9q22.1 |
| NTRK3 | NM_002530 | 15q24-q25 |
| PAK7 | NM_020341 | 20p12 |
| PARK2 | NM_004562 | 6q25.2-q27 |
| PARP1 | NM_001618 | 1q41-q42 |
| PAX5 | NM_016734 | 9p13.2 |
| PBRM1 | NM_018165 | 3p21 |

TABLE 2-continued

IMPACT gene list and positions.

| Gene Symbol | RefSeq ID | Chromosome |
|---|---|---|
| PDGFRA | NM_006206 | 4q12 |
| PDGFRB | NM_002609 | 5q33.1 |
| PHOX2B | NM_003924 | 4p13 |
| PIK3C2G | NM_004570 | 12p12 |
| PIK3CA | NM_006218 | 3q26.3 |
| PIK3CB | NM_006219 | 3q21-qter |
| PIK3CD | NM_005026 | 1p36.2 |
| PIK3CG | NM_002649 | 7q22 |
| PIK3R1 | NM_181504 | 5q13.1 |
| PIK3R2 | NM_005027 | 19q13.2-q13.4 |
| PIK3R3 | NM_003629 | 1p34.1 |
| PKM2 | NM_002654 | 15g22-qter |
| PLK2 | NM_006622 | 5q12.1-q13.2 |
| PNRC1 | NM_006813 | 6q16.1 |
| PREX2 | NM_024870 | 8q13.1 |
| PRKAR1A | NM_002734 | 17q23-q24 |
| PRKCI | NM_002740 | 3q26.3 |
| PTCH1 | NM_000264 | 9q22.1-q31 |
| PTEN | NM_000314 | 10q23 |
| PTPN11 | NM_002834 | 12q24.1 |
| PTPRD | NM_002839 | 9p24.1-p23 |
| PTPRS | NM_002850 | 19p13.3 |
| RAF1 | NM_002880 | 3p25 |
| RARA | NM_000964 | 17q21.1 |
| RB1 | NM_000321 | 13q14.2 |
| REL | NM_002908 | 2p13-p12 |
| RET | NM_020630 | 10q11.2 |
| RICTOR | NM_152756 | 5p13.1 |
| RPTOR | NM_020761 | 17q25.3 |
| RUNX1 | NM_001754 | 21q22.3 |
| SDHB | NM_003000 | 1p36.1-p35 |
| SETD2 | NM_014159 | 3p21.31 |
| SHQ1 | NM_018130 | 3p13 |
| SMAD4 | NM_005359 | 18q21.1 |
| SMARCA4 | NM_003072 | 19p13.3 |
| SMARCB1 | NM_003073 | 22q11.23 |
| SMO | NM_005631 | 7q32.1 |
| SOCS1 | NM_003745 | 16p13.13 |
| SOX2 | NM_003106 | 3q26.3-q27 |
| SPOP | NM_003563 | 17q21.33 |
| SRC | NM_005417 | 20q12-q13 |
| STK11 | NM_000455 | 19p13.3 |
| SUFU | NM_016169 | 10q24.32 |
| TBK1 | NM_013254 | 12q14.2 |
| TEK | NM_000456 | 9p21 |
| TERT | NM_198253 | 5p15.33 |
| TET1 | NM_030625 | 10q21 |
| TET2 | NM_017628 | 4q24 |
| TGFBR2 | NM_003242 | 3p22 |
| TMPRSS2 | NM_005656 | 21q22.3 |
| TNFAIP3 | NM_006290 | 6q23-q25 |
| TOP1 | NM_003286 | 20q12-q13.1 |
| TP53 | NM_000546 | 17p13.1 |
| TP63 | NM_003722 | 3q27-q29 |
| TSC1 | NM_000368 | 9q34 |
| TSC2 | NM_000548 | 16p13.3 |
| TSHR | NM_000369 | 14q24-q31 |
| VHL | NM_000551 | 3p25.3 |
| WT1 | NM_000378 | 11p13 |
| YAP1 | NM_006106 | 11q13 |
| YES1 | NM_005433 | 18p11.31-p11.21 |

TABLE 3

List of all mutations detected by IMPACT assays in individual patient samples.

| Gene | Pt | Chr | Genomic Coordinates (GRCh37) | REF | ALT | AA Change | Effect | Transcript ID | Allele Freq % |
|---|---|---|---|---|---|---|---|---|---|
| VHL | Pt 1 | 3 | 10183811 | G | T | E94* | Nonsense | NM_000551 | 22 |
| PBRM1 | Pt 1 | 3 | 52621444 | T | A | E991D | Missense | NM_018165 | 24 |
| PHOX2B | Pt 1 | 4 | 41750569 | C | A | G20V | Missense | NM_003924 | 13 |
| NFKB1 | Pt 1 | 4 | 103527732 | T | C | L611P | Missense | NM_003998 | 16 |
| NFKB1 | Pt 1 | 4 | 103527768 | C | T | A623V | Missense | NM_003998 | 17 |
| TSC1 | Pt 1 | 9 | 135786937 | G | — | P311fs | Frameshift | NM_000368 | 22 |
| VHL | Pt 2 | 3 | 10188200 | C | A | H115N | Missense | NM_000551 | 61 |
| TP53 | Pt 2 | 17 | 7577120 | C | T | R273H | Missense | NM_000546 | 59 |
| JAK1 | Pt 2 | 1 | 65344709 | C | — | R110fs | Frameshift | NM_002227 | 24 |
| IGF1R | Pt 2 | 15 | 99467158 | — | C | S847fs | Frameshift | NM_000875 | 37 |
| BAP1 | Pt 3 | 3 | 52440393 | C | A | Splice e9-1 | Splice Site | NM_004656 | 15 |
| VHL | Pt 3 | 3 | 10191641 | GA | — | G212 | Frameshift | NM_000551 | 12 |
| mTOR | Pt 3 | 1 | 11182179 | G | T | Q2223K | Missense | NM_004958 | 15 |
| MLL3 | Pt 3 | 7 | 151878766 | A | G | V2060A | Missense | NM_170606 | 14 |
| VHL | Pt 5 | 3 | 10188210 | T | C | L118P | Missense | NM_000551 | 34 |
| PBRM1 | Pt 5 | 3 | 52595895 | TCACTGCTGAA | — | E1360fs | Frameshift | NM_018165 | 22 |
| ATM | Pt 5 | 11 | 108143312 | T | — | N1044fs | Frameshift | NM_000051 | 23 |
| DAXX | Pt 6 | 6 | 33286886 | G | A | T684M | Missense | NM_001350 | 40 |
| KEAP1 | Pt 6 | 19 | 10610405 | G | A | S102L | Missense | NM_012289 | 41 |

TABLE 4

WEC sequencing for patients #5 and #6. (a) WEC run statistics. (b) WEC mutation detection statistics. (c) List of all mutations identified by WEC.

(a)

| SAMPLE | TOTAL READS | PF UQ BASES ALIGNED | PCT SELECTED BASES | MEAN TARGET COVERAGE | PCT USABLE BASES ON TARGET | PCT TARGET BASES 2X | PCT TARGET BASES 10X | PCT TARGET BASES 20X | PCT TARGET BASES 30X |
|---|---|---|---|---|---|---|---|---|---|
| Pt 5 (N) | 70,182,339 | 5,123,974,440 | 99.14% | 81.62 | 80.41% | 96.54% | 91.96% | 86.08% | 79.47% |
| Pt 5 (T) | 54,314,779 | 3,920,678,104 | 99.18% | 63.22 | 81.17% | 95.86% | 89.77% | 81.73% | 72.13% |
| Pt 6 (N) | 77,253,432 | 5,659,907,427 | 99.20% | 89.00 | 79.34% | 96.39% | 91.70% | 86.10% | 80.08% |
| Pt 6 (T) | 93,018,700 | 6,812,455,829 | 99.21% | 107.21 | 79.48% | 96.67% | 92.90% | 88.33% | 83.49% |

(b)

| | Sample | |
|---|---|---|
| | Pt 5 | Pt 6 |
| DOWNSTREAM | 5333 | 7000 |
| INTERGENIC | 2449 | 2853 |
| INTRON | 34314 | 42840 |
| NON_SYNONYMOUS_CODING | 14711 | 17479 |
| NON_SYNONYMOUS_START | 0 | 0 |
| SPLICE_SITE_ACCEPTOR | 48 | 49 |
| SPLICE_SITE_DONOR | 65 | 80 |
| START_GAINED | 185 | 237 |
| START_LOST | 18 | 17 |
| STOP_GAINED | 265 | 300 |
| STOP_LOST | 167 | 207 |
| SYNONYMOUS_CODING | 6262 | 7901 |
| SYNONYMOUS_START | 0 | 1 |
| SYNONYMOUS_STOP | 12 | 15 |
| UPSTREAM | 816 | 1135 |
| UTR_3_PRIME | 3044 | 4090 |
| UTR_5_PRIME | 790 | 1050 |
| Raw SNP Count | 65926 | 81611 |
| dbSNP | 62134 | 75714 |

(c)

| Gene | Pt ID | Chr | Genomic Coordinates (GRCh37) | REF | ALT | AA Change | Effect | Transcript.ID | Allele Freq % |
|---|---|---|---|---|---|---|---|---|---|
| AKR7A3 | Pt 5 | 1 | 19611604 | A | T | M/K | Missense | NM_012067 | 27 |
| SLC35A3 | Pt 5 | 1 | 100487952 | C | T | L/F | Missense | NM_012243 | 21 |
| TROVE2 | Pt 5 | 1 | 193053996 | GA | G | — | Frameshift | NR_033393 | 20 |
| CAD | Pt 5 | 2 | 27455316 | C | G | S/R | Missense | NM_004341 | 31 |
| OXER1 | Pt 5 | 2 | 42990229 | T | A | H/L | Missense | NM_148962 | 38 |
| RANBP2 | Pt 5 | 2 | 109381202 | A | T | N/Y | Missense | NM_006267 | 17 |
| ZNF717 | Pt 5 | 3 | 75786760 | TC | T | — | Frameshift | NM_001128223 | 18 |
| ATP6V1G2-DDX39B | Pt 5 | 6 | 3023942 | T | C | K/E | Missense | NR_037853 | 25 |
| ABCF1 | Pt 5 | 6 | 30553045 | T | C | F/S | Missense | NM_001025091 | 26 |
| ALDH8A1 | Pt 5 | 6 | 135250302 | T | C | S/G | Missense | NM_001193480 | 24 |
| JARID2 | Pt 5 | 6 | 15501569 | GA | G | — | Frameshift | NM_004973 | 23 |
| NEUROD6 | Pt 5 | 7 | 31378243 | G | A | P/S | Missense | NM_022728 | 24 |
| TOPORS | Pt 5 | 9 | 32542010 | T | C | N/S | Missense | NM_001195622 | 27 |
| HABP4 | Pt 5 | 9 | 99250524 | G | A | A/T | Missense | NM_014282 | 28 |
| PBLD | Pt 5 | 10 | 70044010 | A | T | I/N | Missense | NM_022129 | 24 |
| FAM171A1 | Pt 5 | 10 | 15256214 | TG | T | — | Frameshift | NM_001010924 | 22 |
| ATM | Pt 5 | 11 | 108143312 | AT | A | — | Frameshift | NM_000051 | 32 |
| KLF5 | Pt 5 | 13 | 73649685 | G | T | W/L | Missense | NM_001730 | 30 |
| ANKRD20A9P | Pt 5 | 13 | 19415894 | C | CA | — | Frameshift | NR_027995 | 17 |
| MIR1197 | Pt 5 | 14 | 101491918 | GA | G | — | Frameshift | NR_031713 | 29 |
| PLA2G15 | Pt 5 | 16 | 68293469 | T | G | L/W | Missense | NM_012320 | 22 |
| ITGA3 | Pt 5 | 17 | 48156815 | C | A | P/Q | Missense | NM_002204 | 31 |
| TMX4 | Pt 5 | 20 | 7963023 | G | A | R/W | Missense | NM_021156 | 31 |
| C20orf118 | Pt 5 | 20 | 35515885 | T | A | F/I | Missense | NM_080628 | 21 |
| TSHZ2 | Pt 5 | 20 | 51871927 | A | T | K/* | Nonsense | NM_001193421 | 25 |
| KIF17 | Pt 6 | 1 | 21014104 | C | A | R/M | Missense | NM_001122819 | 33 |
| AGL | Pt 6 | 1 | 100379220 | A | G | K/E | Missense | NM_000028 | 36 |
| IGSF8 | Pt 6 | 1 | 160063808 | G | T | A/E | Missense | NM_001206665 | 37 |
| PRG4 | Pt 6 | 1 | 186278230 | A | T | R/* | Nonsense | NM_001127708 | 33 |
| FBXO2 | Pt 6 | 1 | 11710779 | C | CGCG | A/AP | Frameshift | NM_012168 | 50 |
| WDR54 | Pt 6 | 2 | 74650637 | A | G | S/G | Missense | NM_032118 | 40 |
| STAMBP | Pt 6 | 2 | 74087188 | CT | C | — | Frameshift | NM_006463 | 36 |

TABLE 4-continued

WEC sequencing for patients #5 and #6. (a) WEC run statistics. (b) WEC mutation detection statistics. (c) List of all mutations identified by WEC.

| | | | | | | | | | |
|---|---|---|---|---|---|---|---|---|---|
| PVRL3 | Pt 6 | 3 | 110830925 | G | A | W/* | Nonsense | NM_001243286 | 41 |
| ISY1 | Pt 6 | 3 | 128853674 | C | G | — | Splice Site | NM_020701 | 25 |
| ISY1-RAB43 | Pt 6 | 3 | 128853675 | G | T | L/I | Missense | NM_001204890 | 24 |
| C3orf25 | Pt 6 | 3 | 129121412 | T | C | K/E | Missense | NM_207307 | 38 |
| SI | Pt 6 | 3 | 164697187 | A | C | V/G | Missense | NM_001041 | 33 |
| COL7A1 | Pt 6 | 3 | 48618050 | CT | C | — | Frameshift | NM_000094 | 37 |
| DCP1A | Pt 6 | 3 | 53326687 | TA | T | — | Frameshift | NM_018403 | 42 |
| PARP14 | Pt 6 | 3 | 122419572 | T | TAC | — | Frameshift | NM_017554 | 34 |
| PPEF2 | Pt 6 | 4 | 76797687 | G | T | P/H | Missense | NM_006239 | 34 |
| DAB2 | Pt 6 | 5 | 39388912 | T | C | K/E | Missense | NM_001244871 | 37 |
| SSBP2 | Pt 6 | 5 | 80756906 | T | C | R/G | Missense | NM_012446 | 42 |
| NMUR2 | Pt 6 | 5 | 151784319 | C | T | C/Y | Missense | NM_020167 | 41 |
| TAP1 | Pt 6 | 6 | 32821452 | G | A | P/S | Missense | NM_000593 | 29 |
| DAXX | Pt 6 | 6 | 33286886 | G | A | R/* | Nonsense | NR_024517 | 44 |
| FTSJD2 | Pt 6 | 6 | 37419624 | G | A | E/K | Missense | NM_015050 | 41 |
| STL | Pt 6 | 6 | 125231574 | A | T | Y/N | Missense | NR_026876 | 32 |
| GTPBP10 | Pt 6 | 7 | 90012289 | A | C | E/A | Missense | NM_001042717 | 34 |
| SSPO | Pt 6 | 7 | 149487383 | GC | G | — | Frameshift | NM_198455 | 47 |
| VCPIP1 | Pt 6 | 8 | 67577332 | T | A | N/I | Missense | NM_025054 | 35 |
| TJP2 | Pt 6 | 9 | 71827506 | A | T | T/S | Missense | NM_001170414 | 42 |
| ODF2 | Pt 6 | 9 | 131256871 | A | G | E/G | Missense | NM_001242352 | 47 |
| NOXA1 | Pt 6 | 9 | 140327502 | G | C | G/R | Missense | NM_006647 | 32 |
| GAD2 | Pt 6 | 10 | 26505757 | G | A | G/S | Missense | NM_000818 | 39 |
| ZNF33A | Pt 6 | 10 | 38345237 | A | G | I/V | Missense | NM_006954 | 36 |
| MCU | Pt 6 | 10 | 74644033 | T | C | Y/H | Missense | NM_138357 | 34 |
| P4HA1 | Pt 6 | 10 | 74828612 | T | C | N/S | Missense | NM_000917 | 40 |
| KIAA0913 | Pt 6 | 10 | 75554386 | T | C | V/A | Missense | NM_001242487 | 38 |
| ECHS1 | Pt 6 | 10 | 135179536 | T | G | K/T | Missense | NM_004092 | 40 |
| AGAP4 | Pt 6 | 10 | 46342676 | CA | C | — | Frameshift | NM_133446 | 33 |
| IFIT5 | Pt 6 | 10 | 91178337 | G | GT | — | Frameshift | NM_012420 | 32 |
| NAP1L4 | Pt 6 | 11 | 2972543 | T | G | E/D | Missense | NM_005969 | 41 |
| SPON1 | Pt 6 | 11 | 14276269 | C | G | P/R | Missense | NM_006108 | 25 |
| SLC22A24 | Pt 6 | 11 | 62886396 | A | G | F/S | Missense | NM_001136506 | 43 |
| MALAT1 | Pt 6 | 11 | 65271721 | A | T | K/N | Missense | NR_002819 | 37 |
| MALAT1 | Pt 6 | 11 | 65271722 | A | T | I/F | Missense | NR_002819 | 37 |
| FAM138D | Pt 6 | 12 | 147968 | GT | G | — | Frameshift | NR_026823 | 100 |
| ATP8A2 | Pt 6 | 13 | 26594101 | A | G | K/R | Missense | NM_016529 | 24 |
| ANKRD20A9P | Pt 6 | 13 | 19415894 | C | CA | — | Frameshift | NR_027995 | 11 |
| MIS18BP1 | Pt 6 | 14 | 45711551 | C | G | D/H | Missense | NM_018353 | 55 |
| NEMF | Pt 6 | 14 | 50292663 | G | T | S/* | Nonsense | NM_004713 | 62 |
| TDP1 | Pt 6 | 14 | 90456086 | G | A | R/Q | Missense | NM_001008744 | 42 |
| SAV1 | Pt 6 | 14 | 51132213 | GA | G | — | Frameshift | NM_021818 | 53 |
| SPATA5L1 | Pt 6 | 15 | 45713319 | A | G | T/A | Missense | NM_024063 | 64 |
| SMYD4 | Pt 6 | 17 | 1715384 | T | A | R/* | Nonsense | NM_052928 | 38 |
| FLJ90757 | Pt 6 | 17 | 79005261 | C | A | R/M | Missense | NR_026857 | 29 |
| C19orf28 | Pt 6 | 19 | 3557268 | A | G | L/P | Missense | NM_001042680 | 37 |
| KEAP1 | Pt 6 | 19 | 10610405 | G | A | S/L | Missense | NM_012289 | 36 |
| KLK9 | Pt 6 | 19 | 51509963 | G | A | L/F | Missense | NM_012315 | 33 |
| NLRP12 | Pt 6 | 19 | 54313633 | G | C | T/R | Missense | NM_144687 | 44 |
| SLC9A8 | Pt 6 | 20 | 48461621 | C | A | P/T | Missense | NM_015266 | 31 |
| SON | Pt 6 | 21 | 34927665 | G | A | R/Q | Missense | NM_032195 | 41 |
| PI4KA | Pt 6 | 22 | 21119924 | G | A | R/* | Nonsense | NM_058004 | 35 |
| POM121L8P | Pt 6 | 22 | 21649094 | AC | A | — | Frameshift | NR_024583 | 25 |
| TLR8 | Pt 6 | X | 12938246 | T | G | F/V | Missense | NM_138636 | 38 |
| CYBB | Pt 6 | X | 37665639 | G | T | — | Splice Site | NM_000397 | 32 |

TABLE 5

Summary of oncogenomic findings in patients #1 to #6.

| Patient | | Oncongenomic Findings | | R1 | R2 | R3 | Proposed Mechanism for repalog-sensitivity |
|---|---|---|---|---|---|---|---|
| 1 | P13K/Akt/MTOR pathway alterations: | Somatic mutations: TSCI frameshift (P311fs*4) TSCI nonsense (Q527*) CNA: Heterozygous loss of Chr 9 | | X<br><br><br>X | X<br><br><br>X | <br>X<br><br>X | Functional loss of Tscl |

TABLE 5-continued

Summary of oncogenomic findings in patients #1 to #6.

| Patient | | Oncongenomic Findings | | | | | Proposed Mechanism for repalog-sensitivity |
|---|---|---|---|---|---|---|---|
| | Other pertinent genomic alterations: | Somatic mutations: VHL Nonsense (E94*) PBRMI Missense (E991D) CNA: Heterozygous loss of Chr 3p | X X X | X X X | X X X | | |
| 2 | P13K/Akt/MTOR pathway alterations | Somatic mutations: TSCI Frameshift (1580fs*7) CNA: Heterozygous loss of Chr 9 | R1 X X | R2 X X | R3 X X | M1 X X | Functional loss of Tscl |
| | Other pertinent genomic alterations: | Somatic mutations: VHL Misssense (H115N) TP53 Missense (R273H) CNA: | X X | X X | X X | X X | |
| 3 | P13K/Akt/MTOR pathway alterations: | Somatic mutations: MTOR missense (Q2223K) TSCI nonsense (Q781*) CNA: Heterozygous loss of Chr 9 | R1 x | R2 x | R3 x x x | R4 x x x | Hyperactive MTOR/ Functional loss of Tscl |
| | Other pertinent genomic alterations: | Somatic mutations: VHL frameshift (G212fs) BAPI splice (g220_splice) BAPI splice (Q85_splice) CNA: Heterozygous loss of Chr 3p | x | x | x x | x | |
| 4 | P13K/Akt/MTOR pathway alterations: | Somatic mutations: TSC2 frameshift (Q794*) CNA: Homozygous loss of TSC2 Heterozygous loss of TSC2 | T1 X | T2 X X | | | Functional loss Tsc2 |
| | Other pertinent genomic alterations. | Somatic mutations: none CNA: None | | | | | |
| 5 | P13K/Akt/MTOR pathway alterations: | Somatic mutations: none CNA: None | R1 | M1 | | | Unclear |
| | Other pertinent genomic alterations: | Somatic mutations: VHL missense (L118P) PBRMI frameshift (E1360fs) CNA: Heterozygous loss of Chr 3p | X X X | X X X | | | |
| 6 | P13K/Akt/MTOR pathway alterations: | Somatic mutations: none CNA: None | R1 | | | | Unclear |
| | Other pertinent genomic alterations: | Somatic mutations: none CNA: None | | | | | |
| 7 | P13K/Akt/MTOR pathway alterations: | Somatic mutations: none CNA: Heterozygous loss of Chr 9 | R1 X | | | | N/A |
| | Other pertinent genomic alterations: | Somatic mutations: none CNA: Heterozygous loss of Chr 9 | X | | | | |
| 8 | P13K/Akt/MTOR pathway alterations: | Somatic mutations MTOR missense (E919V) CNA: Heterozygous loss of Chr 9q | R1 X X | | | | N/A |

TABLE 5-continued

Summary of oncogenomic findings in patients #1 to #6.

| Patient | | Oncongenomic Findings | | Proposed Mechanism for repalog-sensitivity |
|---|---|---|---|---|
| | Other pertinent genomic alterations: | Somatic mutations: VHL missense (S65L) BAP1 splice (e6-1) PBRM1 splice (e5-2) SETD2 frameshift (E2477fs) CNA: Heterozygous loss of Chr 3p | X X X X X | |
| 9 | | | R1 | N/A |
| | P13K/Akt/MTOR pathway alterations: | Somatic mutations: TSC2 missense (1475F) CNA: | x | |
| | Other pertinent genomic alterations: | Somatic mutations: None CNA: MAP2K1 amplification | X | |
| 10 | | | R1 | N/A |
| | P13K/Akt/MTOR pathway alterations: | Somatic mutations: PTEN missense (F2001) CNA: None | X | |
| | Other pertinent genomic alterations: | Somatic mutations: None CNA: PDGFRA, KIT amplification | X | |

CNA: copy number alteration;
Chr: chromosome

TABLE 6 mTOR mutations in clear cell renal cell carcinoma from the TCGA.

| ID | Amino Acid | Nucleotide | Genome Start GRCh37 | Genome End GRCh37 | Source/PUBMED ID |
|---|---|---|---|---|---|
| TCGA-AK-3429 | G5R | c.13G > C | 11319454 | 11319454 | TCGA |
| TCGA-B0-5119 | K860N | c.2580G > C | 11291426 | 11291426 | TCGA |
| TCGA-BP-5001 | L1433S | c.4298T > C | 11227530 | 11227530 | TCGA |
| TCGA-CZ-5987 | K1452N | c.4356A > C | 11217322 | 11217322 | TCGA |
| TCGA-BP-5176 | A1459P | c.4375G > C | 11217303 | 11217303 | TCGA |
| TCGA-B0-5701 | L1460P | c.4376T > C | 11217299 | 11217299 | TCGA |
| TCGA-BP-5175 | L1460P | c.4376T > C | 11217299 | 11217299 | TCGA |
| TCGA-B0-5697 | Y1463S | c.4388A > C | 11217290 | 11217290 | TCGA |
| TCGA-B0-5696 | C1483Y | c.4448G > A | 11217230 | 11217230 | TCGA |
| TCGA-CJ-6027 | A1519T | c.4555G > A | 11210198 | 11210198 | TCGA |
| TCGA-B0-4846 | F1888I | c.5662T > A | 11189847 | 11189847 | TCGA |
| TCGA-CZ-4857 | F1888L | c.5662T > C | 11189847 | 11189847 | TCGA |
| TCGA-CZ-4866 | F1888L | c.5662T > C | 11189847 | 11189847 | TCGA |
| TCGA-B0-5100 | I1973F | c.5917A > T | 11188177 | 11188177 | TCGA |
| TCGA-B0-4827 | T1977K | c.5919C > A | 11188164 | 11188164 | TCGA |
| TCGA-CJ-4644 | V2006L | c.6016G > C | 11188078 | 11188078 | TCGA |
| TCGA-B0-4852 | E2033V | c.6098A > T | 11187799 | 11187799 | TCGA |

TABLE 6-continued mTOR mutations in clear cell renal cell carcinoma from the TCGA.

| ID | Amino Acid | Nucleotide | Genome Start GRCh37 | Genome End GRCh37 | Source/PUBMED ID |
|---|---|---|---|---|---|
| TCGA-B0-4810 | A2210P | c.6628G > C | 11184589 | 11184589 | TCGA |
| TCGA-CJ-5679 | S2215F | c.6644C > A | 11184573 | 11184573 | TCGA |
| TCGA-CJ-4887 | L2230V | c.6688T > G | 11182158 | 11182158 | TCGA |
| TCGA-A3-3347 | M2327I | c.6981G > A | 11177096 | 11177096 | TCGA |
| TCGA-B0-5691 | L2334V | c.7000T > G | 11177077 | 11177077 | TCGA |
| TCGA-CW-5580 | I2500M | c.7500T > G | 11169375 | 11169375 | TCGA |

TABLE 7

Primers. Primers for PCR-mutagenesis are:

| Mutation | Primer Sequence |
|---|---|
| K860N | GAG CCC TAC AGG AAT TAC CCT ACT TTG C |
| E919V | GTC AGC CTG TCA GTA TCC AAG TCA AGT C |
| A1105P | CCA GCT GTT TGG CCC CAA CCT GGA TGA C |
| L1443S | GCG GCC GGA GTG TCA GAA TAT GCC ATG AAA C |
| A1459P | CAC GAG TGG GAG GAT CCC CTT GTG GCC TAT G |
| L1460P | GTG GGA GGA TGC CCC TGT GGC CTA GAA CAA G |
| C1483F | GGG CCG CAT GCG CTT CCT CGA GGC CTT GGG |
| E1799K | GCA GTG ATG AAC TTC AAA GCT GTG CTA CAC |
| F1888I | CTG CCG TCC AGG GCA TCT TCC GTT CCA TCT C |
| F1888L | GCC GTC CAG GGC TTG TTC CGT TCC ATC TCC |
| F1888V | CTG CCG TCC AGG GCG TCT TCC GTT CCA TCT C |
| I1973F | CCC CCA GGC CCT CTT CTA CCC ACT GAC AG |
| T1977K | CAT CTA CCC ACT GAA AGT GGC TTC TAA GTC |
| V2006L | CAC AGC AAC ACC CTG CTC CAG CAG GCC ATG |
| S2215F | CCA ATG ACC CAA CAT TTC TTC GGA AAA ACC |
| L2220F | CAT CTC TTC GGA AAA ACT TCA GCA TCC AGA G |
| Q2223K | GGA AAA ACC TCA GCA TCA AGA GAT ACG CTG TC |
| I2228T | GAG ATA CGC TGT CAC CCC TTT ATC GAC C |
| L2230V | CGC TGT CAT CCC TGT ATC GAC CAA CTC GG |
| M2327I | GTT CTT TAG CGG TCA TAT CAA TGG TTG GG |
| V2406A | CAC AGT GAT GGA GGC GCT GCG AGA GCA C |
| L2431P | GCT GAA CTG GAG GCC GAT GGA CAC AAA TAC C |

TABLE 7-continued

Primers. Primers for PCR-mutagenesis are:

| Mutation | Primer Sequence |
|---|---|
| R2505P | GAT TAT TAA CAG GGT TCC AGA TAA GCT CAC TGG |

8. EXAMPLE: PROPERTIES OF MTOR MUTANTS ASSOCIATED WITH THERAPEUTIC RESPONSE TO RAPALOGS

Various experiments were performed to explore the properties of identified mTOR mutants.

To test the ability of cells carrying mTOR mutations to grow in serum-depleted conditions, Hela cells, transfected with Flag-mTOR constructs bearing various mutations, were cultured either without serum (−) or in the presence of 10% serum (+) for 1 hour. Cellular lysates were then subjected to immunoblot analysis to assess phosphorylation of S6K as a measure of mTOR activity. As shown in FIG. 24, mTOR mutants associated with therapeutic response to rapalogs were found to be more resistant to serum than wild-type mTOR.

Experiments were then performed to test the effect of an AKT inhibitor on the activity of mTOR mutants. Hela cells, transfected with Flag-mTOR constructs carrying various mTOR mutations, were cultured in medium with (+) or without (−) 1 μM MK2206, an AKT inhibitor for 2 hours. Cellular lysates were then subjected to immunoblot analysis analysis to assess phosphorylation of S6K as a measure of mTOR activity. As shown in FIG. 25, mTOR mutants associated with therapeutic response to rapalogs were found to be more resistant to AKT inhibitor than wild-type mTOR.

The ability of rapamycin and INK128 to inhibit activity of the mTOR mutants was also tested. Transfected Hela cells expressing various mTOR mutants were cultured in medium with (+) or without (−) 25 nM rapamycin or 100 nM INK128 for 2 hours. Cellular lysates were then subjected to immunoblot analysis analysis to assess phosphorylation of S6K as a measure of mTOR activity. As shown in FIG. 26, mTOR mutants associated with therapeutic response to rapalogs were found to be sensitive to rapamycin or to INK128, an ATP-competitive inhibitor of mTORC1 and mTORC2.

9. EXAMPLE: SYNERGISTIC EFFECT OF DOUBLE MUTATION

Figure 27A:
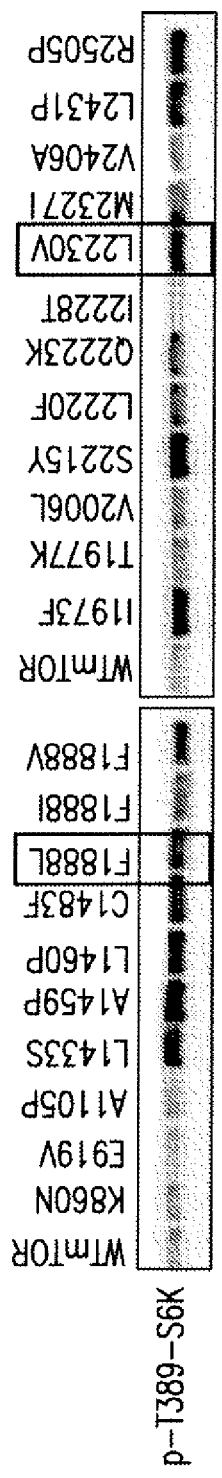
Figure 27B:
Figure 27C:
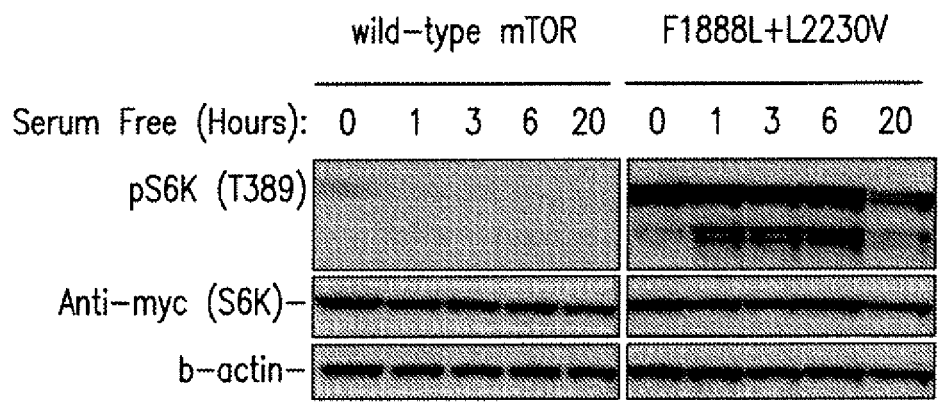
Figure 27D:
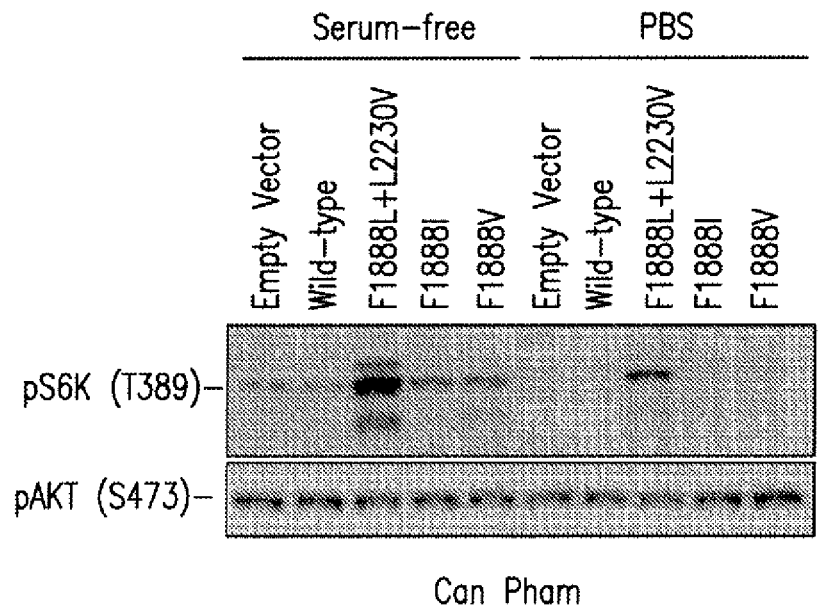

The effect of concurrent mutations F188L and L2230V on mTOR activity, as reflected by phosphorylation of S6K, was evaluated. In experiments analogous to those described in the preceding section, cells expressing single or double mTOR mutants were prepared. FIG. 27A depicts the level of phosphorylation of S6K in the presence of single F1881L and L2230V mutations. FIG. 27B depicts phosphorylation of S6K where both mutations are present (other single mutants shown for comparison), where phosphorylation levels were substantially higher in the double-mutant mTOR expressing cells. This higher level of mTOR activity was further demonstrated by resistance to serum depletion (FIG. 27C) and was even observed when cells were cultured in phosphate buffered saline (FIG. 27D), indicative of a high level of activity.

10. REFERENCES

1. Molina, A. M. & Motzer, R. J. Clinical practice guidelines for the treatment of metastatic renal cell carcinoma: today and tomorrow. The oncologist 16 Suppl 2, 45-50 (2011).
2. Linehan, W. M., Srinivasan, R. & Schmidt, L. S. The genetic basis of kidney cancer: a metabolic disease. Nature reviews. Urology 7, 277-285 (2010).
3. Kaelin, W. G., Jr. The von Hippel-Lindau tumour suppressor protein: 02 sensing and cancer. Nature reviews. Cancer 8, 865-873 (2008).
4. Kaelin, W. G., Jr. Treatment of kidney cancer: insights provided by the VHL tumor-suppressor protein. Cancer 115, 2262-2272 (2009).
5. Brugarolas, J. Renal-cell carcinoma—molecular pathways and therapies. The New England journal of medicine 356, 185-187 (2007),
6. Laplante, M. & Sabatini, D. M. mTOR signaling in growth control and disease. Cell 149, 274-293 (2012).
7. Dazert, E. & Hall, M. N. mTOR signaling in disease. Current opinion in cell biology 23, 744-755 (2011).
8. Hudes, G., et al. Temsirolirnus, interferon alfa, or both for advanced renal-cell carcinoma. The New England journal of medicine 356, 2271-2281 (2007).
9. Motzer, R. J., et al. Efficacy of everolimus in advanced renal cell carcinoma: a double-blind, randomised, placebo-controlled phase III trial. Lancet 372, 449-456 (2008).
10. Molina, A. M., Ginsberg, M. S. & Motzer, R. J. Long-term response with everolimus for metastatic renal cell carcinoma refractory to sunitinib. Med Oncol 28, 1527-1529 (2011).
11. Dutcher, J. P., et al. Effect of temsirolimus versus interferon-alpha on outcome of patients with advanced renal cell carcinoma of different tumor histologies. Med Oncol 26, 202-209 (2009).
12. Atkins, M. B., et al. Randomized phase II study of multiple dose levels of CCI-779, a novel mammalian target of rapamycin kinase inhibitor, in patients with advanced refractory renal cell carcinoma. Journal of clinical oncology: official journal of the American Society of Clinical Oncology 22, 909-918 (2004).
13. Amato, R. J., Jac, J., Giessinger, S., Saxena, S. & Willis, J. P. A phase 2 study with a daily regimen of the oral mTOR inhibitor RAD001 (everolimus) in patients with metastatic clear cell renal cell cancer. Cancer 115, 2438-2446 (2009).
14. Vivanco, I. & Sawyers, C. L. The phosphatidylinositol 3-Kinase AKT pathway in human cancer. Nature reviews. Cancer 2, 489-501 (2002).
15. Kwiatkowski, D. J. Animal models of lymphangioleiomyomatosis (LAM) and tuberous sclerosis complex (TSC), Lymphatic research and biology 8, 51-57 (2010).
16. Krueger, D. A., et al. Everolimus for subependymal giant-cell astrocytomas in tuberous sclerosis. The New England journal of medicine 363, 1801-1811 (2010).
17. Qin, W., et al. Angiomyolipoma have common mutations in TSC2 but no other common genetic events. PLoS One 6, e24919 (2011).
18 Kucejova, B., et al. Interplay between pVHL and mTORC1 pathways in clear-cell renal cell carcinoma. Molecular cancer research: MCR 9, 1255-1265 (2011).
19. Iyer, G., et al. Genome sequencing identifies a basis for everolimus sensitivity. Science 338, 221 (2012).
20. Gerlinger, M., et al. Intratumor heterogeneity and branched evolution revealed by multiregion sequencing. The New England journal of medicine 366, 883-892 (2012).
21. Gnirke, A., et al. Solution hybrid selection with ultra-long oligonucleotides for massively parallel targeted sequencing. Nat Biotechnol 27, 182-189 (2009).
22. Wagle, N., et al. High-throughput detection of actionable genomic alterations in clinical tumor samples by targeted, massively parallel sequencing. Cancer discovery 2, 82-93 (2012).
23. Paez, J. G., et al. EGFR mutations in lung cancer: correlation with clinical response to gefitinib therapy. Science 304, 1497-1500 (2004).
24. Urano, J., et al. Point mutations in TOR confer Rheb-independent growth in fission yeast and nutrient-independent mammalian TOR signaling in mammalian cells. Proceedings of the National Academy of Sciences of the United States of America 104, 3514-3519 (2007).
25. Sawyers, C. L. The cancer biomarker problem. Nature 452, 548-552 (2008). 26. Longo, D. L. Tumor heterogeneity and personalized medicine. The New England journal of medicine 366, 956-957 (2012).
27. Yap, T. A., Gerlinger, M., Futreal, P. A., Pusztai, L. & Swanton, C. Intratumor heterogeneity: seeing the wood for the trees. Science translational medicine 4, 127ps110 (2012).
28. Nowell, P. C. The clonal evolution of tumor cell populations. Science 194, 23-28 (1976).
29. Vogelstein, B. & Kinzler, K. W. Cancer genes and the pathways they control. Nat Med 10, 789-799 (2004).
30. Hanahan, D. & Weinberg, R. A. Hallmarks of cancer: the next generation. Cell 144, 646-674 (2011).
31. Li, H., et al. The Sequence Alignment/Map format and SAMtools. Bioinformatics 25, 2078-2079 (2009).
32. Li, H. & Durbin, R. Fast and accurate short read alignment with Burrows-Wheeler transform. Bioinformatics 25, 1754-1760 (2009).
33. DePristo, M. A., et al. A framework for variation discovery and genotyping using next-generation DNA sequencing data. Nat Genet 43, 491-498 (2011).
34. Robinson, J. T., et al. Integrative genomics viewer. Nature biotechnology 29, 24-26 (2011).
35. McKenna, A., et al. The Genome Analysis Toolkit: a MapReduce framework for analyzing next-generation DNA sequencing data. Genome research 20, 1297-1303 (2010).
36. Wagle, Berger et al., Cancer Discovery 2:82-93 (2012).

Various publications and nucleic acid and amino acid sequence accession numbers are cited herein, the contents and full sequences of which are hereby incorporated by reference herein in their entireties.

What is claimed is:

1. A method of producing an anti-cancer effect in a cancer, comprising:
  administering a therapeutically effective amount of a rapamycin analog to the cancer to produce an anti-cancer effect,
  wherein cells of the cancer have been determined to contain a biomarker selected from the group consisting of:
    a TSC1 biomarker, which is a TSC1 Q781* biomarker, TSC1 P311fs*4 biomarker, TSC1 I580fs*7 biomarker, TSC1 Q527* biomarker, TSC1 S334* biomarker or a combination thereof;
    a TSC2 biomarker, which is a TSC2 Q794* biomarker, TSC2 R611W biomarker, TSC2 S1498N biomarker or a combination thereof;
    a mTOR biomarker, which is:
      a mTOR mutation selected from the group consisting of Q2223K, R2505P, L2431P, S2215F, V2406A, M2327I, L2230V, I2228T, L2220F, V2006L, T1977K, I1973F, F1888V, F1888I, F1888L, F1888L in combination with L2230V, C1483F, C1483Y, L1460P, A1459P, L1433S, A1105P, K860N and a combination thereof; and
    a combination thereof,
  wherein the cancer is renal cell carcinoma.

2. The method of claim 1, where the presence of a TSC1 biomarker, a TSC2 biomarker, and/or a mTOR biomarker is determined by nucleic acid sequencing.

3. The method of claim 2, where nucleic acid complementary to a TSC1 gene, a TSC2 gene, and/or a gene encoding a mTOR biomarker is amplified and the amplified nucleic acid is subjected to nucleic acid sequencing.

4. The method of claim 1, where the biomarker is a mTOR biomarker.

5. The method of claim 4, where the mTOR biomarker is Q2223K.

6. The method of claim 1, where the biomarker is a TSC1 biomarker.

7. The method of claim 1, where the biomarker is a TSC2 biomarker.

8. The method of claim 4, where the mTOR biomarker is selected from the group of mutations consisting of Q2223K, R2505P, L2431P, S2215F, V2406A, M2327I, L2230V, I2228T, L2220F, V2006L, T1977K, I1973F, F1888V, F1888I, F1888L, F1888L in combination with L2230V, C1483F, C1483Y, L1460P, A1459P, L1433S, A1105P and K860N.

9. A method of treating a subject suffering from a cancer, comprising:
  treating the subject with a therapeutically effective amount of a rapamycin analog,
  wherein cells of the cancer have been determined to contain a biomarker selected from the group consisting of:
    a TSC1 biomarker, which is a TSC1 Q781* biomarker, TSC1 P311fs*4 biomarker, TSC1 I580fs*7 biomarker, TSC1 Q527* biomarker, TSC1 S334* biomarker or a combination thereof;
    a TSC2 biomarker, which is a TSC2 Q794* biomarker, TSC2 R611W biomarker, TSC2 S1498N biomarker or a combination thereof;
    a mTOR biomarker, which is:
      a mTOR mutation selected from the group consisting of Q2223K, R2505P, L2431P, S2215F, V2406A, M2327I, L2230V, I2228T, L2220F, V2006L, T1977K, I1973F, F1888V, F1888I, F1888L, F1888L in combination with L2230V, C1483F, C1483Y, L1460P, A1459P, L1433S, A1105P, K860N and a combination thereof; and
    a combination thereof,
  where the cancer is renal cell carcinoma.

10. The method of claim 9, where the presence of a TSC1 biomarker, a TSC2 biomarker, and/or a mTOR biomarker is determined by nucleic acid sequencing.

11. The method of claim 10, where nucleic acid complementary to a TSC1 gene, a TSC2 gene, and/or a gene encoding a mTOR biomarker is amplified and the amplified nucleic acid is subjected to nucleic acid sequencing.

12. The method of claim 9, where the biomarker is a mTOR biomarker.

13. The method of claim 12, where the mTOR biomarker is Q2223K.

14. The method of claim 9, where the biomarker is a TSC1 biomarker.

15. The method of claim 9, where the biomarker is a TSC2 biomarker.

16. The method of claim 12, where the mTOR biomarker is selected from the group of mutations consisting of Q2223K, R2505P, L2431P, S2215F, V2406A, M2327I, L2230V, I2228T, L2220F, V2006L, T1977K, I1973F, F1888V, F1888I, F1888L, F1888L in combination with L2230V, C1483F, C1483Y, L1460P, A1459P, L1433S, A1105P and K860N.

17. A method of producing an anti-cancer effect in a renal cell carcinoma wherein cells of the renal cell carcinoma have been determined to contain cell a mTOR biomarker selected from the group consisting of Q2223K, R2505P, L2431P, S2215F, V2406A, M2327I, L2230V, I2228T, L2220F, V2006L, T1977K, I1973F, F1888V, F1888I, F1888L, F1888L in combination with L2230V, C1483F, C1483Y, L1460P, A1459P, L1433S, A1105P, K860N and a combination thereof, comprising:
  administering, to a subject having the renal cell carcinoma an effective amount of a rapamycin analog.

* * * * *